(12) United States Patent
Baker

(10) Patent No.: US 11,389,536 B2
(45) Date of Patent: Jul. 19, 2022

(54) TREATMENT OF CANCER WITH A COMBINATION OF RADIATION, CERIUM OXIDE NANOPARTICLES, AND A CHEMOTHERAPEUTIC AGENT

(71) Applicant: BioCurity Pharmaceuticals Inc., Jupiter, FL (US)

(72) Inventor: Cheryl Baker, New Smyrna Beach, FL (US)

(73) Assignee: BioCurity Pharmaceuticals Inc., Jupiter, FL (US)

( * ) Notice: Subject to any disclaimer, the term of this patent is extended or adjusted under 35 U.S.C. 154(b) by 0 days.

(21) Appl. No.: 15/326,208

(22) PCT Filed: Jul. 17, 2015

(86) PCT No.: PCT/US2015/040869
§ 371 (c)(1),
(2) Date: Jan. 13, 2017

(87) PCT Pub. No.: WO2016/011328
PCT Pub. Date: Jan. 21, 2016

(65) Prior Publication Data
US 2017/0202965 A1 Jul. 20, 2017

(51) Int. Cl.
| | |
|---|---|
| A61K 9/51 | (2006.01) |
| A61K 41/00 | (2020.01) |
| A61K 33/24 | (2019.01) |
| A61K 45/06 | (2006.01) |
| A61K 9/00 | (2006.01) |
| A61N 5/10 | (2006.01) |
| A61K 9/06 | (2006.01) |
| A61K 9/08 | (2006.01) |
| A61K 47/32 | (2006.01) |
| A61K 47/02 | (2006.01) |
| A61K 31/7068 | (2006.01) |
| A61K 31/337 | (2006.01) |
| A61K 33/244 | (2019.01) |
| A61K 33/243 | (2019.01) |
| A61K 33/242 | (2019.01) |

(52) U.S. Cl.
CPC ........ *A61K 41/0038* (2013.01); *A61K 9/0014* (2013.01); *A61K 9/0019* (2013.01); *A61K 9/06* (2013.01); *A61K 9/08* (2013.01); *A61K 31/337* (2013.01); *A61K 31/7068* (2013.01); *A61K 33/24* (2013.01); *A61K 33/243* (2019.01); *A61K 33/244* (2019.01); *A61K 45/06* (2013.01); *A61K 47/02* (2013.01); *A61K 47/32* (2013.01); *A61N 5/10* (2013.01); *A61K 33/242* (2019.01)

(58) Field of Classification Search
CPC ...... A61K 9/51; A61K 9/5107; A61K 9/5115; A61K 9/5192
See application file for complete search history.

(56) References Cited

U.S. PATENT DOCUMENTS

| | | |
|---|---|---|
| 6,669,823 B1 | 12/2003 | Sarkas et al. |
| 6,955,639 B2 | 10/2005 | Hainfeld et al. |
| 7,347,987 B2 | 3/2008 | McGinnis et al. |
| 7,504,356 B1 | 3/2009 | Self et al. |
| 7,534,453 B1 | 5/2009 | Rzigalinski et al. |
| 7,727,559 B2 | 6/2010 | McGinnis et al. |
| 7,767,630 B2 | 8/2010 | Gupta et al. |
| 8,048,523 B2 | 11/2011 | Kambe et al. |
| 8,333,933 B2 | 12/2012 | Oshiro et al. |
| 8,333,993 B1 | 12/2012 | Perez et al. |
| 8,616,104 B2 | 12/2013 | Frolov et al. |
| 8,703,200 B2 | 4/2014 | McGinnis et al. |
| 8,747,907 B2 | 6/2014 | Rzigalinski et al. |
| 8,883,519 B1 | 11/2014 | Perez et al. |
| 8,951,539 B1 | 2/2015 | Das et al. |
| 9,119,391 B1 | 9/2015 | Perez et al. |
| 9,161,950 B2 | 10/2015 | Self et al. |
| 9,393,439 B2 | 7/2016 | Goer |
| 9,415,065 B2 * | 8/2016 | Vujaskovic .......... A61K 33/244 |
| 9,463,437 B2 | 10/2016 | Self et al. |
| 9,524,800 B2 | 12/2016 | Griffin et al. |
| 9,585,840 B1 | 3/2017 | Brenneisen et al. |

(Continued)

FOREIGN PATENT DOCUMENTS

| | | |
|---|---|---|
| EP | 2130553 A | 12/2009 |
| WO | 2007002662 A2 | 1/2007 |

(Continued)

OTHER PUBLICATIONS

Kong FM, et al (Radiation dose effective in locally advanced non-small cell lung cancer, J. Thorac Dis 2014; 6 (4): 336-347) (Year: 2014).*
Sevil et al (Effects of Gamma irradiation on cell cycle, apoptosis and telomerase activity in p53 wild-type and deficient BCT116 colon cancer cell lines; Oncology Letters, 6, 807-810, 2013) (Year: 2013).*
European Patent Office, Supplementary European Search Report issued in EP15822181., dated Nov. 17, 2017.
Gao, Y., et al. "Cerium oxide nanoparticles in cancer", OncoTargets and Therapy, May 1, 2014, vol. 7, pp. 835-840, Dovepress.
Sack, M., et al. "Combination of Conventional Chemotherapeutics with Redox-Active Cerium Oxide Nanoparticles—A Novel Aspect in Cancer Therapy", Molecular Cancer Therapeutics, May 13, 2014, vol. 13(7), pp. 1740-1749, American Association for Cancer Research.

(Continued)

*Primary Examiner* — Micah Paul Young
(74) *Attorney, Agent, or Firm* — Taft Stettinius & Hollister LLP; Joseph M. Bennett-Paris

(57) ABSTRACT

The present invention is directed to methods for the treatment of cancer with a combination of radiation, cerium oxide nanoparticles and at least one chemotherapeutic agent. Cerium oxide nanoparticles (CONPs) are nanometer-sized crystals of cerium oxide, typically ranging between about one nanometer to about 20 nanometers in longest dimension. The present methods use cerium oxide nanoparticles to enhance radiation-induced and chemotherapy-induced cancer cell death and also reduce the toxicity associated with radiation therapy and chemotherapy.

20 Claims, 30 Drawing Sheets

(56) References Cited

U.S. PATENT DOCUMENTS

| | | | |
|---|---|---|---|
| 9,649,337 | B2 | 5/2017 | Rzigalinski et al. |
| 2006/0194057 | A1 | 8/2006 | Pfluecker et al. |
| 2007/0251786 | A1 | 11/2007 | Wegner |
| 2008/0003483 | A1 | 1/2008 | Guo |
| 2008/0159980 | A1 | 7/2008 | Xu et al. |
| 2009/0092671 | A1 | 4/2009 | Rzigalinski et al. |
| 2010/0015042 | A1 | 1/2010 | Keisari et al. |
| 2011/0111007 | A1 | 5/2011 | McGinnis et al. |
| 2011/0213192 | A1* | 9/2011 | Levy .............. A61K 41/0038 600/1 |
| 2012/0251496 | A1 | 10/2012 | Wick |
| 2012/0282185 | A1 | 11/2012 | Dobson et al. |
| 2013/0195927 | A1 | 8/2013 | Seal et al. |
| 2013/0337070 | A1 | 12/2013 | Brenneisen et al. |
| 2014/0273215 | A1* | 9/2014 | Guo ................ A61K 41/0042 435/375 |
| 2014/0335015 | A1* | 11/2014 | Pottier ............. A61K 9/5115 424/1.29 |
| 2015/0335744 | A1* | 11/2015 | Petty ................ B01J 35/006 252/600 |
| 2016/0074434 | A1 | 3/2016 | Perez et al. |

FOREIGN PATENT DOCUMENTS

| | | |
|---|---|---|
| WO | 2013151698 A1 | 10/2013 |
| WO | 2013187980 A1 | 12/2013 |
| WO | 2014088920 A1 | 6/2014 |
| WO | 2015164780 A1 | 10/2015 |
| WO | 2016166550 A1 | 10/2016 |

OTHER PUBLICATIONS

Zhang, L., et al., "Selective Cytotoxicity Effect of Cerium Oxide Nanoparticles Under UV Irradiation", Journal of Biomedical Nanotechnology, Feb. 1, 2014, vol. 10(2), pp. 278-286, American Scientific Publishers.

Grundmann, et al., Sensitivity of Salivary Glands to Radiation: from Animal Models to Therapies, Journal of Dental Research, 2009, pp. 894-903, vol. 88 (1), International & American Association for Dental Research.

Jones, et al., Simple Method for Quantifying Pulmonary Metastases in a Murine Fibrosarcoma, Cancer Research, Dec. 1983, pp. 5657-5661, vol. 43, American Association for Cancer Research.

Mehta, Radiation Pneumonitis and Pulmonary Fibrosis in Non-Small-Cell Lung Cancer: Pulmonary Function, Prediction, and Prevention, International Journal of Radiation Oncology, Sep. 1, 2003, pp. 5-24, vol. 83(1), Elsevier.

Clark, A., et al. "Neuroscience 2003 Abstract." Society for Neuroscience. 2003. New Orleans, LA. Retrieved from: http://www.sfn.org/annual-meeting/past-and-future-annual-meetings.

Hu, K., et al.; Rationale for Integrating High-Dose Rate Intraoperative Radiation (HDR-IORT) and Postoperative External Beam Radiation with Subcutaneous Amifostine for the Management of Stage III/IV Head and Neck Cancer; Semin. Oncol.; 2003; (6 Suppl. 18); 40-48.

Korsvik, C. et al.; Superoxide Dismutase Mimetic Properties Exhibited by Vacancy Engineering Ceria Nanoparticles; ChemComm. 2007, 1-4.

Lin, W., et al.; Toxicity of Cerium Oxide Nanoparticles in Human Lung Cancer Cells; Intl. J. Toxicol., 2006; (6); 451-7.

Naito, Y., et al.; Oxidative Stress-Related Molecules as a Therapeutic Target for Inflammatory and Allergic Diseases; Cur. Drug Targets Inflamm. Allergy; 2005; 4; 511-515.

Niu, J., et al. Cardioprotective Effects of Cerium Oxide Nanoparticles in a Transgenic Murine Model of Cardiomyopathy; Cardiovasc. Res., 2007; 73(3); 549-559. Eup8b, Nov. 30, 2006.

Smijs, T., et al.; Titanium dioxide and zinc oxide nanoparticles in sunscreens: focus on their safety and effectiveness; Nanotechnology, Science and Applications; Oct. 12, 2011; pp. 95-112; vol. 4; Dove Medical Press Ltd.

Tarnuzzer, R. W., et al.; Vacancy Engineered Ceria Nanostructures for Protection from Radiation-Induced Cellular Damage; Nano Lett., 2005; (12); 2573-2577.

U.S. Patent and Trademark Office. International Search Report and Written Opinion of the International Searching Authority issued in PCT/US2015/040869, dated Oct. 23, 2015. 21 Pages. Alexandria, Virginia.

U.S. Patent and Trademark Office. Office Action issued in U.S. Appl. No. 14/860,044, dated Oct. 21, 2016. 8 Pages. Alexandria, Virginia.

The International Bureau of WIPO. International Preliminary Report on Patentability issued in PCT/US2015/040869, dated Jan. 17, 2017. 19 Pages. Geneva, Switzerland.

Cancer Nanotechnology: The impact of passive and active targeting in the era of modern cancer biology; Nicolas Bertrand et al.; Dept. of Health and Human Services; Adv. Drug Delivery. Author Manuscript; available in PMC Feb. 1, 2015.

"The Science Behind Radiation Therapy" published by the American Cancer Society in 2016 ("ACS").

Colon et al. (Protection from radiation-induced pheumonitis using cerium oxide nanoparticles; Nanomedicine; Nanotechnology, Biology, and Medicine 5, 2009, 225-231) (Year 2009).

Sensitization of pancreatic cancer cells to radiation by cerium oxide nanoparticle-induced ROS production; Wason et al.; Nanomedicine: Nanotechnology, Biology, and Medicine 9 (2013) 558-569.

Harnessing Nanoparticles to Improve Toxicity After Head and Neck Radiation; Madero-Visbal et al.; Nanomedicine: Nanotechnology, Biology, and Medicine vol. 8 (2012); 1223-1231.

Nanomaterials Based on Cerium Dioxide: Properties and Use Perspectives in Biology and Medicine; A. B. Shcherbakov et al.; Zabolotny Institute of Microbiology and Virology of National Academy of Sciences of Ukraine, Kyiv 2Kurnakov Institute of General and Inorganic Chemistry of Academy of Sciences of Russia, Moscow, Russian Federation 3Moscow State University M. Lomonosov, Moscow, Russian Federation; 2011, pp. 9-28 (English translation also enclosed).

Clark et al., (2011) Cerium oxide and platinum nanoparticles protect cells from oxidant-mediated apoptosis. Journal of Nanoparticle Research 13: 5547-5555 (pp. 1-15).

* cited by examiner (Radiation alone)

(Radiation + $CeO_2$)

T = Tumor
N = Normal

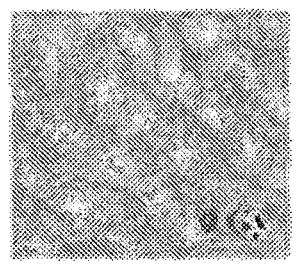 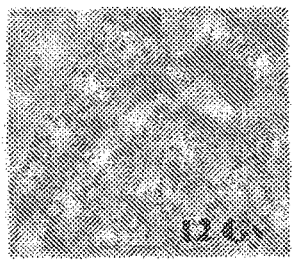
FIG. 22A  FIG. 22B
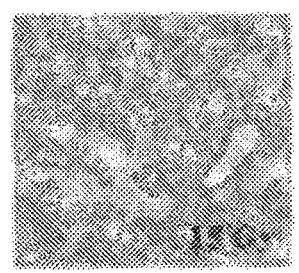 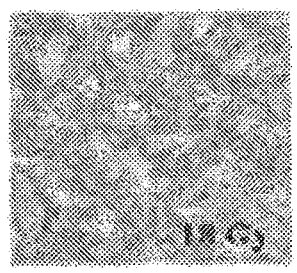
FIG. 22C  FIG. 22D
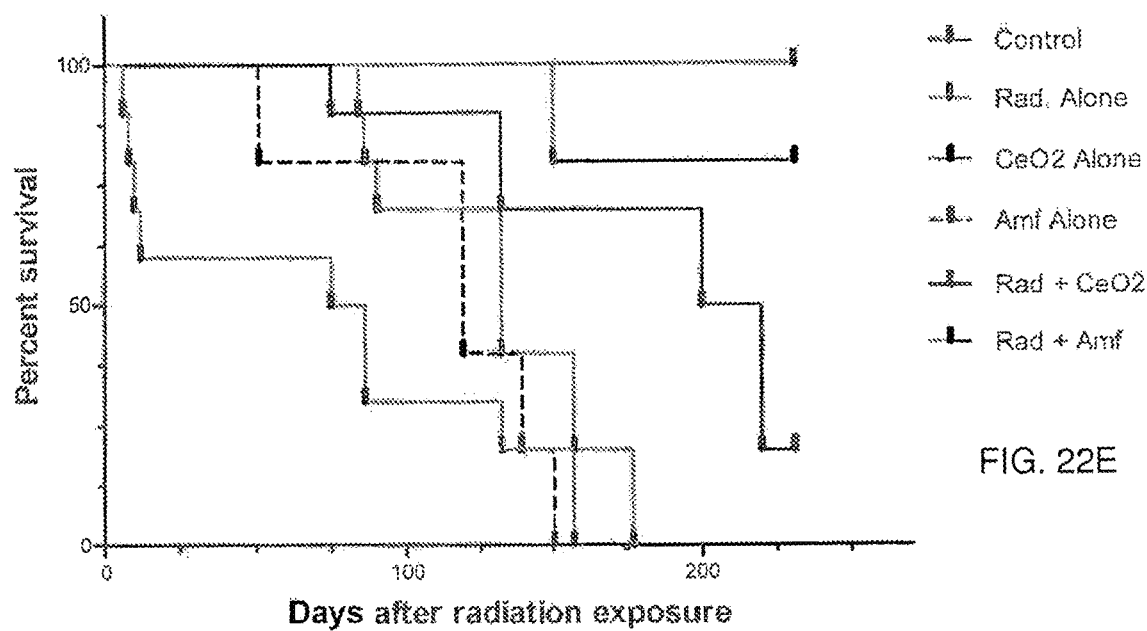
FIG. 22E FIG. 23A Control  FIG. 23B Radiation  FIG. 23C Radiation + CeO2  FIG. 24D Radiation + Amifostine

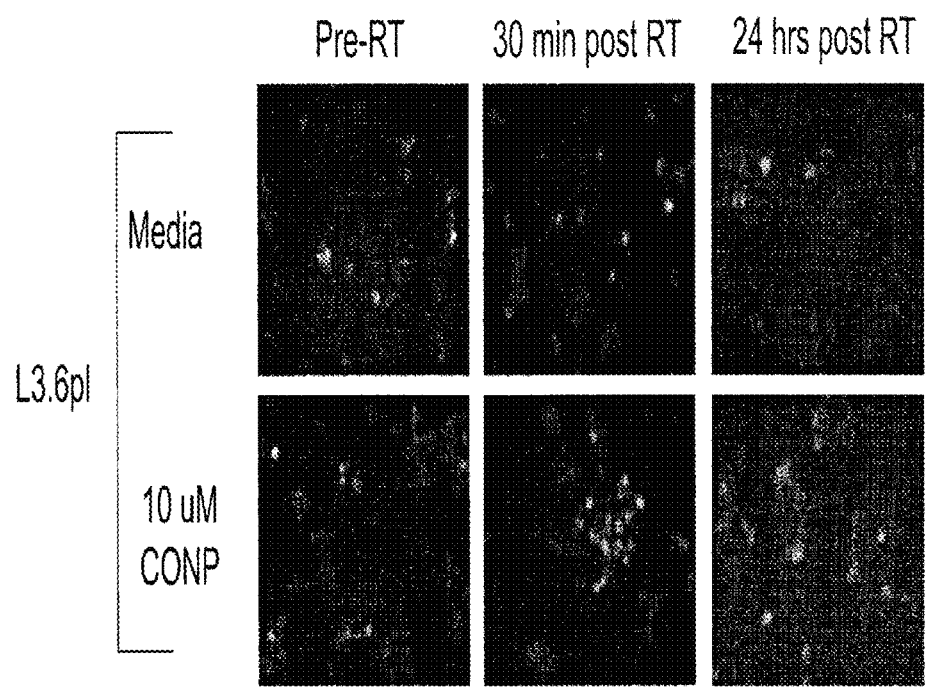
FIG. 25A(i)
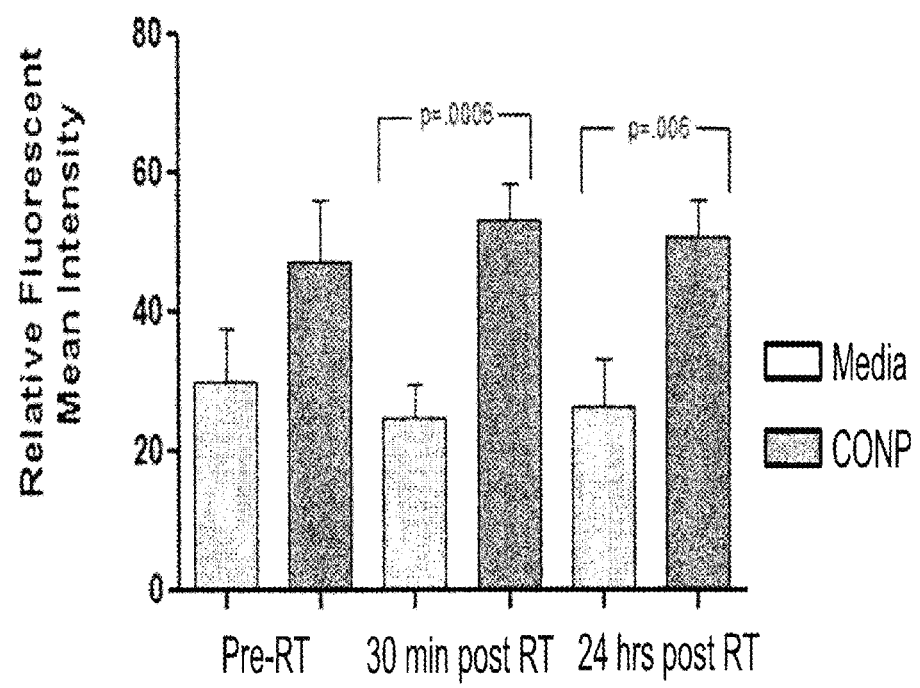

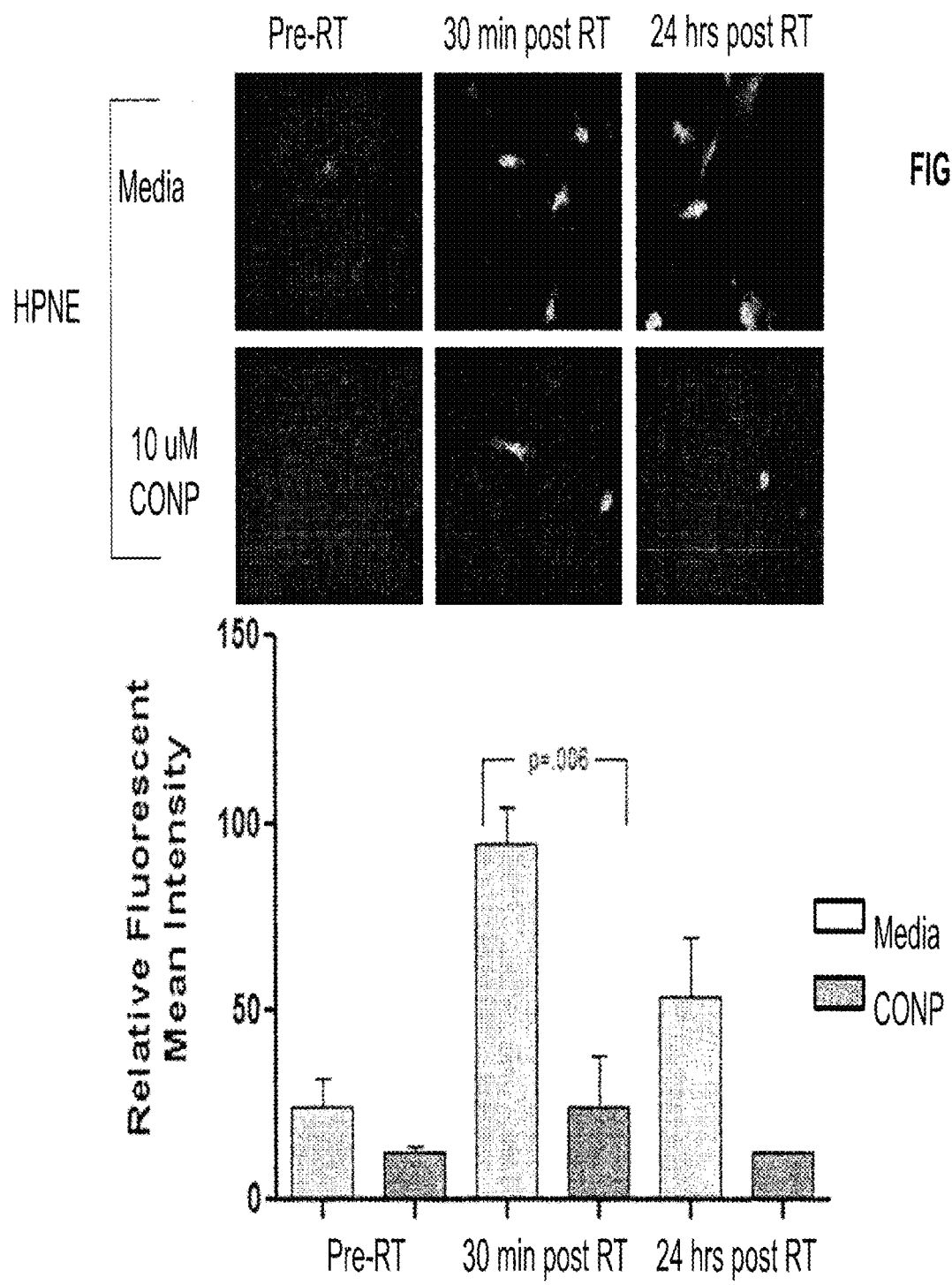
FIG. 25A(ii)

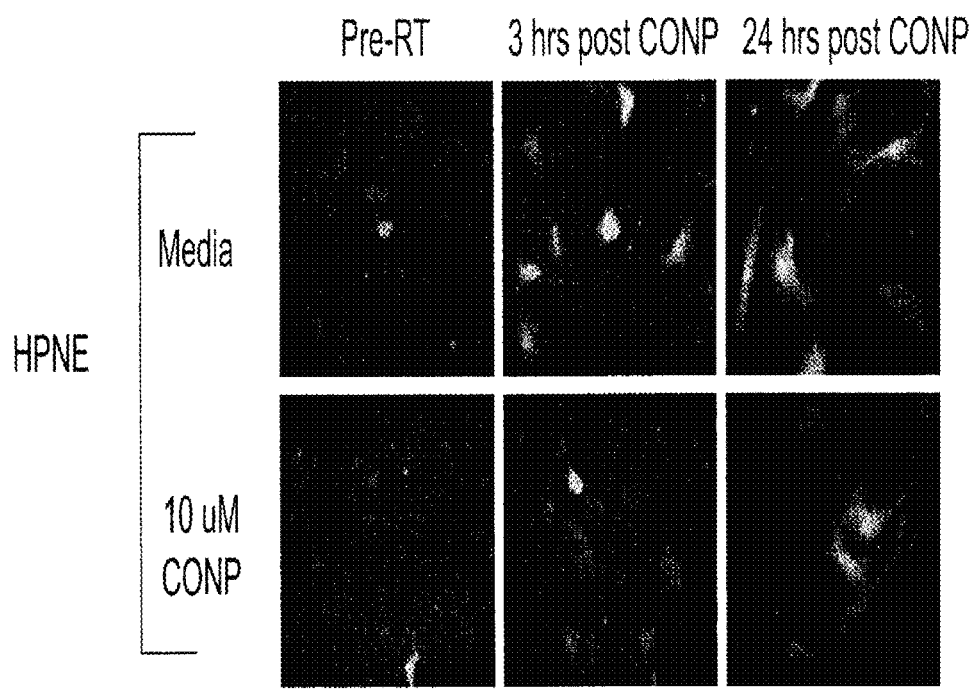
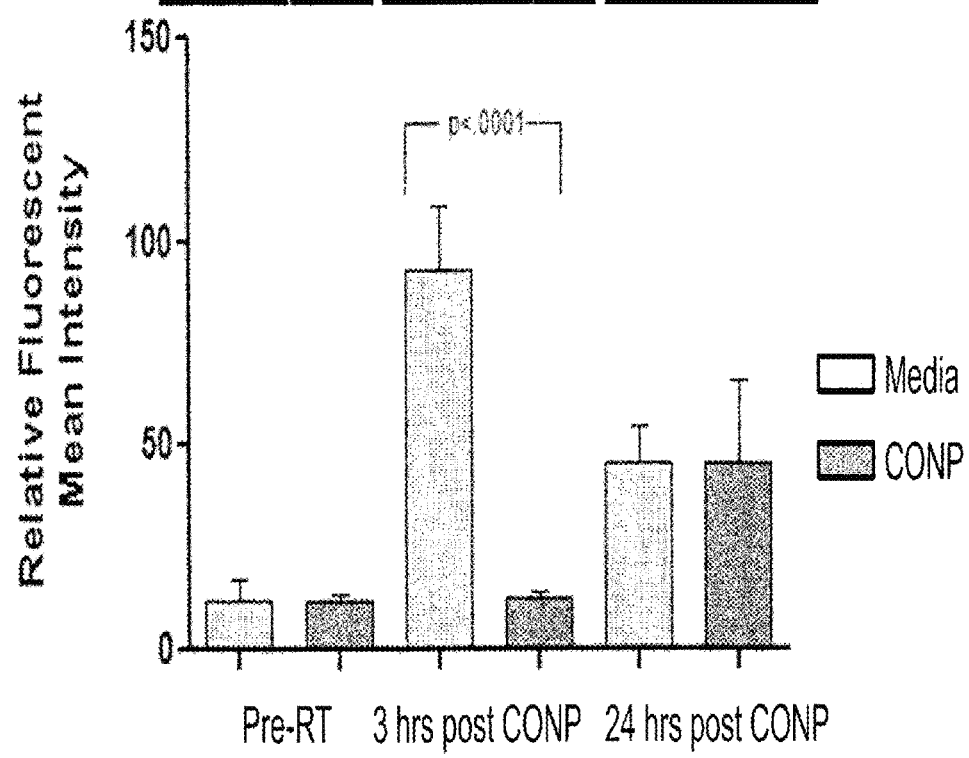
FIG. 25B (ii)

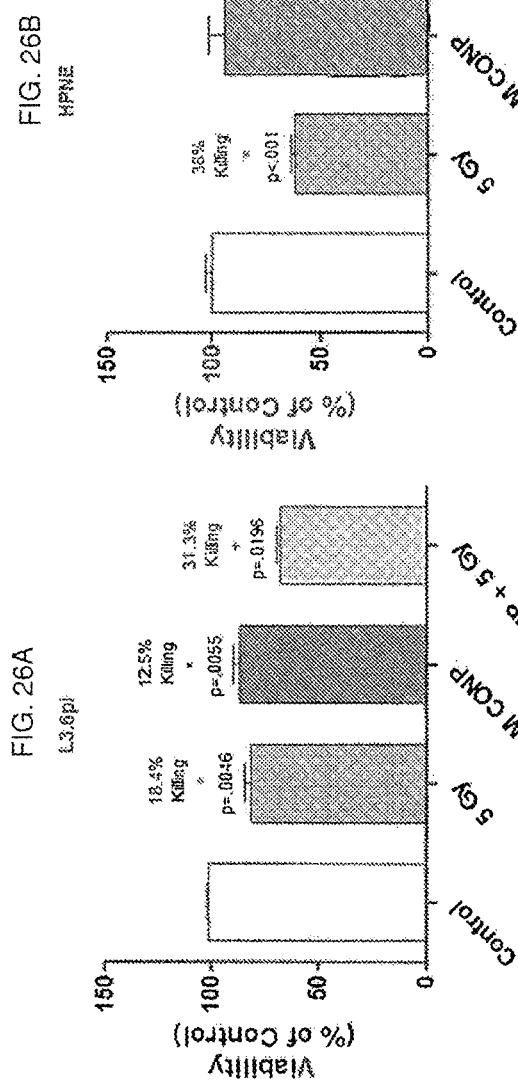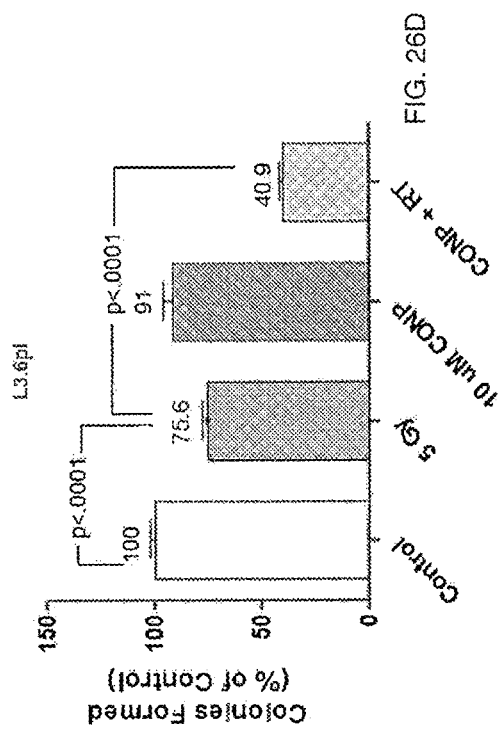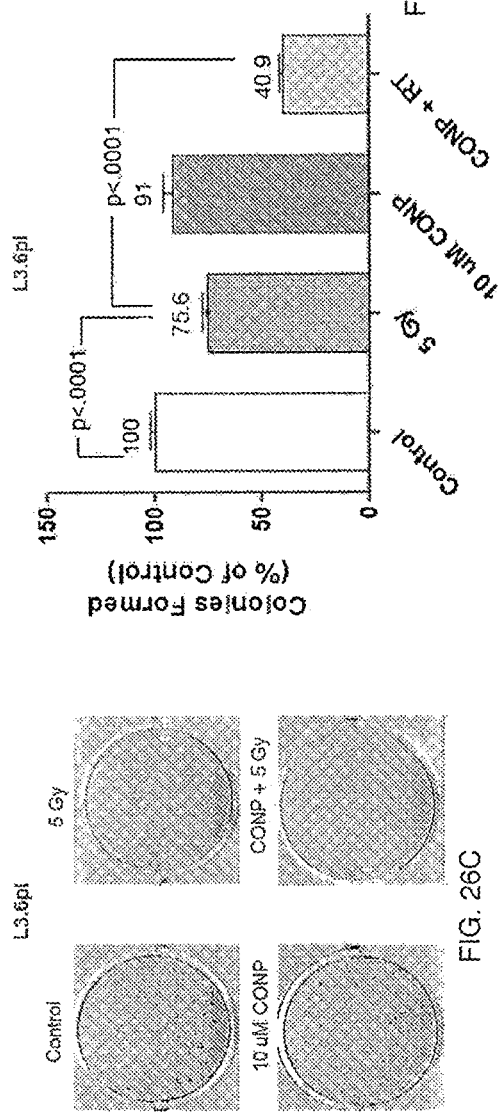

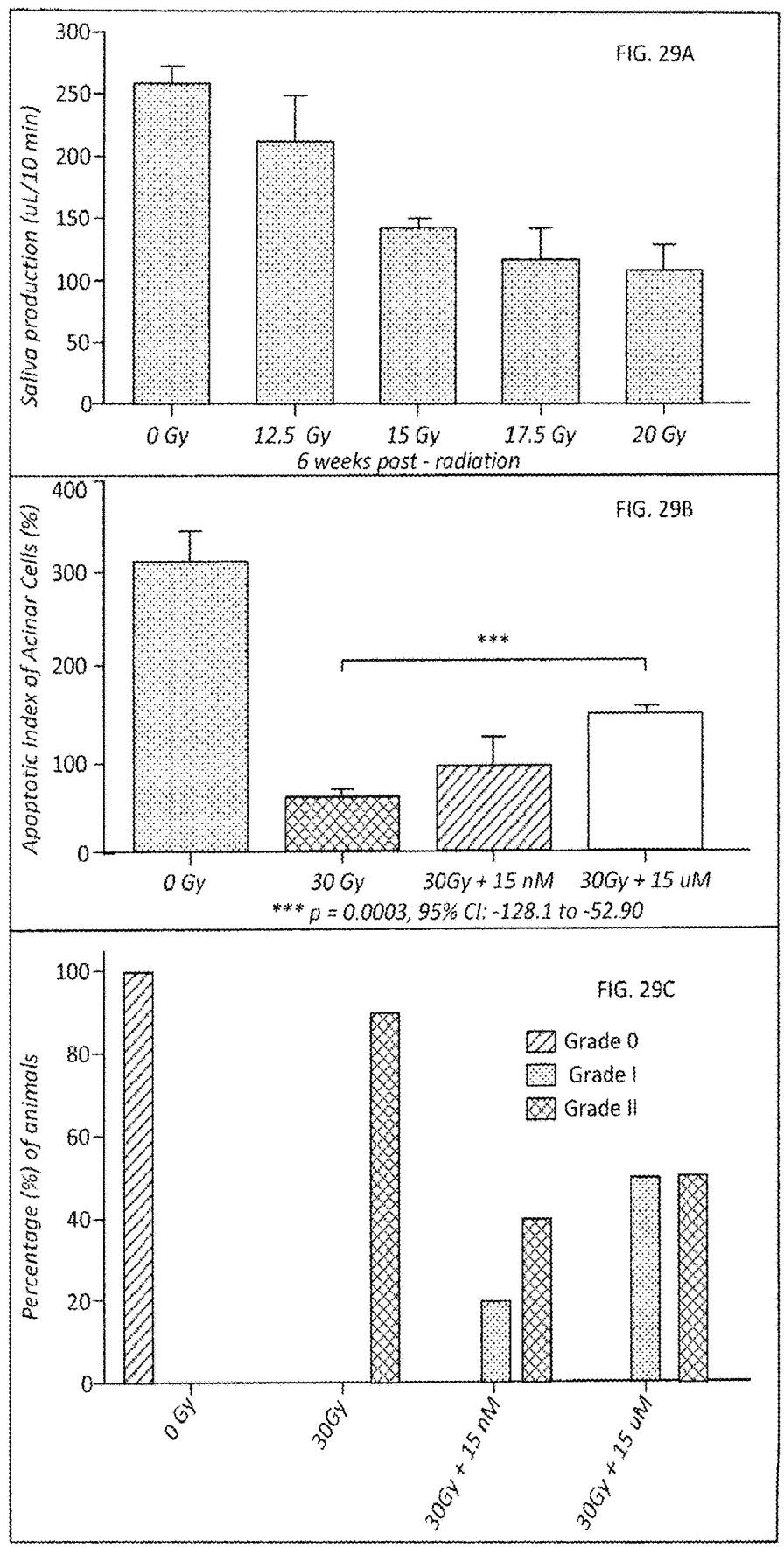

Effect of CeO2 nanoparticles in combination with radiation + paclitaxel on lung cancer cell viability over a course of 96 hours

TREATMENT OF CANCER WITH A COMBINATION OF RADIATION, CERIUM OXIDE NANOPARTICLES, AND A CHEMOTHERAPEUTIC AGENT

CROSS REFERENCE TO RELATED APPLICATIONS

This application is a U.S. national stage application under 35 U.S.C. § 371 of PCT International Application Serial No PCT/US2015/040869, which has an international filing date of Jul. 17, 2015. The disclosures of each of these prior applications are hereby expressly incorporated by reference in their entirety.

FIELD OF THE INVENTION

The present invention relates to methods for a treatment of a cancer in a patient. More specifically, the present invention relates to methods for the treatment of cancer with a combination of radiation, cerium oxide nanoparticles and a chemotherapeutic agent.

BACKGROUND OF THE INVENTION

Radiation is a well-known therapy for killing cancer cells and shrinking cancer tumors in a patient. Radiation is used to produce ionizing reactions that form free radicals, which react with DNA, and RNA triggering programmed cell death (apoptosis) in cancer cells. Free radical generation from radiation is also damaging to normal cells and the physiology of organs in the path of the radiation therapy treating the cancer tumor of the patient.

One of the most visible side-effects of radiation therapy in cancer patients is a radiation-induced dermatitis (inflammation of the skin) in the radiation path during radiation treatment of a cancer patient's tumor. The severity of the skin damage is directly proportional to number of doses and frequency of the radiation treatment.

The field of radiation oncology has worked diligently over the last decade to improve radiation delivery techniques in order to spare sensitive structures from the effects of ionizing radiation. These techniques have resulted in improved functional outcomes compared to prior, more rudimentary, radiation techniques. However, the need to attain adequate tumor coverage and the exquisite radio-sensitivity of certain normal structures in the head and neck are intrinsic limitations to the magnitude of function and quality of life that can be preserved with these techniques. Under even the best of circumstances, many cancer patients, after radiation therapy to treat their cancer tumor, experience significant toxicity from the radiation treatment.

Chemotherapy is another approach used to treat cancer tumors in a patient. Chemotherapy is a practice whereby anticancer drugs are administered to a patient to interfere with the viability of the cancer cells in the tumor. Certain chemotherapy drugs may be given in a specific order depending on the type of cancer under treatment. While chemotherapy can be quite effective in treating certain cancers, chemotherapy drugs can reach all parts of the body, not just the cancer cells. Because of this distribution, there can be widespread side effects during systemic chemotherapy treatment. A combination of chemotherapies is frequently tried to improve cancer treatment of a patient, however, combination chemotherapy does not necessarily lessen the toxicity of the therapy.

Cancer cells are unlike normal tissue cells in that regular cellular mechanisms and behaviors are absent making choice of therapy and resulting efficacy less predictable. Living cells have numerous complex parallel and series cellular signaling pathways and genetic pathways. One difficulty is that cancer cells are very dysfunctional, poorly regulated, and possess a genetic variability so that it is difficult to be able to identify the key genetic mutations making the cancer successful. Cancer drug discovery and testing is actively being pursued to target the key alterations in cancer cells that most critically impact the spread, aggressiveness, formation, and viability of cancer tumors. If cancer biology could be so simplified, then in theory, a selective chemotherapy mixture might be very effective in killing a cancer tumor. However, cancer cells in a tumor are comprised of different mutation clones with each subpopulation of cancer cells having different genotypes and perhaps different phenotypes. Drug resistance is an issue and some cancer cells may survive chemotherapy because they are more resistant to the cancer drug. Cancer drug resistance may be due to increased cancer drug metabolism by the cancer cell or by an increased rate of cancer drug transport out of the cancer cell by a cancer drug membrane transporter, so that the intracellular cancer drug concentration remains sub-toxic to the cancer cell.

Furthermore, tissue mechanisms can impact efficacy of treatment and later recurrence. Cancer cells multiply without normal cell contact inhibition regulating their multicellular growth, and generally grow beyond their existing blood supply. The tumor remains hypoxic to some extent and metabolically reliant more so on glycolysis than normal cells. Cancer cells depend less on aerobic metabolism than normal cells as a rule. To compensate for the growth limiting effects of hypoxia, cancer tumors have genetically evolved means for growing an additional blood vascular bed as needed. This additional blood circulation is termed a hyper-vascular circulation because it has a markedly abnormal vascularity and it is a useful marker for detecting evolving cancer tumors using contrast agent blood flow imaging. Histology of the hyper-vascular blood vessel walls shows the walls comprise a mixture of apparently normal vascular endothelial cells and dysfunctional cancer cells. Functionally the hyper-vascular circulation is so leaky that Gibbs-Donnan regulation fails. Parts of the growing tumor remain hypoxic. This creates a selection pressure such that a subgroup of cells in the tumor becomes more hypoxia tolerant. The blood supply for cancer tumors will never be adequate.

Radiation and/or chemotherapy treatments are known to be very aggressive anti-cancer cell therapies that have an unpredictable efficacy. It is possible that radiation and chemotherapy may alert some cancer cells that they are under attack. Such cancer cells which may be embedded in the vascular endothelium of new blood vessels in a cancer tumor, may then be shed from the tumor and escape into the blood circulation to migrate away from a cancer tumor. Such shed cancer cells may seed a new tumor, which may also have an increased tolerance of hypoxia, and cancer drugs.

In addition, radiation and chemotherapy may allow the most hardy cancer cell subpopulations to survive. It is common to hear that a patient seemed to survive an initial challenge from cancer only to rapidly succumb when the cancer returned very aggressively. This is thought to be due to the survival of a virulent cancer subpopulation that needed time to grow to a lethal tumor burden mass for the patient.

It is against this background of difficulties and complexities in the treatment of cancer that the present invention is concerned.

SUMMARY OF THE INVENTION

In general, the present invention is directed to methods for the treatment of cancer by administering a combination of radiation, cerium oxide nanoparticles (CONPs) and a chemotherapeutic agent.

In a first aspect the invention is a method of treating a cancer in a patient in need thereof, comprising:
administering an effective dose of cerium oxide nanoparticles to the patient;
administering a therapeutically effective dose of radiation to the patient; and
administering a therapeutically effective dose of a chemotherapeutic agent to the patient, thereby treating the cancer.

In one embodiment, the therapeutically effective dose of radiation is a dose which kills cancer cells.

In one embodiment, the therapeutically effective dose of the chemotherapeutic agent is a dose which kills cancer cells.

In one embodiment, the effective dose of cerium oxide nanoparticles is a dose that lowers the therapeutically effective dose of radiation and/or the chemotherapeutic agent compared to the therapeutically effective dose of radiation and/or the chemotherapeutic agent in the absence of the nanoparticles.

In various embodiments, the dose of radiation and/or the chemotherapeutic agent is between about 1% and 90%, or between about 1% and 80%, or between about or 1% and 70%, or between about 1% and 60%, or between about 1% and 50%, or between about 1% and 40%, or between about 1% and 30%, or between about 1% and 20%, or between about 1% and 10% of either (i) the dose used in the current treatment standard in the absence of CONPs or (ii) the effective amount to treat the tumor in the absence of CONPs.

In one embodiment, the radiation is administered after the cerium oxide nanoparticles are administered.

In another embodiment, the radiation is administered before the cerium oxide nanoparticles are administered.

In one embodiment, the chemotherapeutic agent is administered before the cerium oxide nanoparticles and/or radiation.

In another embodiment, the chemotherapeutic agent is administered at the same time as the cerium oxide nanoparticles and/or radiation.

In another embodiment, the chemotherapeutic agent is administered after the cerium oxide nanoparticles and/or radiation.

In another embodiment, the cerium oxide nanoparticles have a particle size between about 1 nanometers to about 20 nanometers.

In another embodiment, the cerium oxide nanoparticles have a particle size between about 3 nanometers to about 15 nanometers.

In another embodiment, the cerium oxide nanoparticles have a particle size between about 3 nanometers to about 10 nanometers.

In another embodiment, the cerium oxide nanoparticles have a particle size between about 3 nanometers to about 5 nanometers.

In another embodiment, the effective dose of the cerium oxide nanoparticles is between about 1 nanogram per kilogram patient body weight to about 50 milligrams per kilogram patient body weight; or between about 1 nanogram per kilogram patient body weight to about 5 milligrams per kilogram patient body weight; or between about 1 nanogram per kilogram patient body weight to about 0.5 milligrams per kilogram patient body weight; or between about 10 nanogram per kilogram patient body weight to about 0.5 milligrams per kilogram patient body weight; or between about 20 nanogram per kilogram patient body weight to about 100 micrograms per kilogram patient body weight; or between about 10 nanogram per kilogram patient body weight to about 10 micrograms per kilogram patient body weight.

In one embodiment, the cerium oxide nanoparticles are provided in the form of a composition comprising cerium oxide nanoparticles and a pharmaceutical carrier. The cerium oxide nanoparticle composition may be administered, for example, by topical, oral, parenteral (e.g., intravenous), buccal, sublingual, nasal, rectal, patch, pump or transdermal administration and the composition formulated accordingly.

In exemplary embodiments, the cerium oxide nanoparticle composition is a topical composition. In one embodiment, the topical composition comprises CONPs, a surfactant, an oil and water. In exemplary embodiments, the cerium oxide nanoparticle composition is a micro-emulsion. In exemplary embodiments, the cerium oxide nanoparticle composition is administered by application to a skin area of the patient.

In another embodiment, the total concentration of cerium oxide nanoparticles in the blood plasma of the patient following administration is between about 5 nanomolar to about 200 micromolar; or between about 10 nanomolar to about 100 micromolar; or between about 20 nanomolar to about 10 micromolar.

The patient may be diagnosed with a pancreatic cancer, a lung cancer, a breast cancer, a colon cancer, a liver cancer, a skin cancer, a brain cancer, a bone cancer, a kidney cancer, an ovarian cancer, a uterine cancer, a prostate cancer, or a head cancer and a neck cancer.

In one embodiment, chemotherapeutic agent is selected from the group consisting of sorafenb, regorafenib, imatinib, eribulin, gemcitabine, capecitabine, pazopani, lapatinib, dabrafenib, sutinib malate, crizotinib, everolimus, torisirolimus, sirolimus, axitinib, gefitinib, anastrole, bicalutamide, fulvestrant, ralitrexed, pemetrexed, goserilin acetate, erlotininb, vemurafenib, visiodegib, tamoxifen citrate, paclitaxel, docetaxel, cabazitaxel, oxaliplatin, ziv-aflibercept, bevacizumab, trastuzumab, pertuzumab, pantiumumab, taxane, bleomycin, melphalen, plumbagin, camptosar, mitomycin-C, mitoxantrone, SMANCS, doxorubicin, pegylated doxorubicin, Folfori, 5-fluorouracil, temozolomide, pasireotide, tegafur, gimeracil, oteraci, itraconazole, bortezomib, lenalidomide, irintotecan, epirubicin, and romidepsin. Preferred chemotherapeutic agents are Carboplatin, Fluorouracil, Vinblastine, Gemcitabine, Cyclophosphamide, Doxorubicin, Methotrexate, Paclitaxel, Topotecan, Etoposide, Methotrexate, Sorafenib, Irinotecan, Tarceva or a combination thereof.

In one embodiment, any chemotherapeutic agent or additional agent that would increase the activity or effectiveness of a chemotherapeutic agent is useful in the methods provided herein.

In one embodiment, the method of practicing the invention involves administering to a patient with a prodrug chemotherapeutic agent selected from the group consisting of a hypoxia activated prodrug, evofosfamide, TH-302, AQN4, banoxatrone, a nitrogen mustard prodrug, PR-104, apaziquone, EO-9, CB1954, 5-(aziridin-1-yl)-4-hydroxylamino-2-nitrobenzamide, canofosfamide, TLK286, TER286, JS-K, and Boc-KAc-Puro.

In one embodiment, the method of practicing the invention involves administering to a patient with a peptidomimetic inhibitor of GSH or GHT-π, for example, a peptidomimetic inhibitor selected from the group consisting of γ-glutamyl-S-(benzyl)cysteinyl-R-phenylglycine diethyl ether, TLK199, Telintra, and NOV-002. The peptidomimetic inhibitor of GSH or GHT-π lowers cancer cell levels of GSH (glutathione) or the activity of GHT-π (glutathione-S-transferase-π) and this can potentiate the toxicity of an administered anticancer drug by preventing its metabolism. Also the treatment of a cancer patient with TLK-199 which is also an inhibitor of the multidrug resistant-associated protein known to be a multidrug efflux transporter, can be used to increase cancer cell levels of a chemotherapeutic agent.

In one embodiment, the cancer chemotherapeutic agent is a prodrug that is activated by GSH. In one embodiment, the method of practicing the invention involves administering to a patient a GSH-activated prodrug selected from the group consisting of cis-6-(2-acetylvinylthio)purine (cis-AVTP), and trans-6-(2-acetylvinylthio)guanine (trans-AVTP). This method of practicing the invention can involve treatment of a cancer patient with a GST-activated prodrug, the GST-activated prodrug selected from the group consisting of γ-glutamyl-α-amino-β(2-ethyl-N,N,N',N'-tetrakis (2-chloroethyl)phosphodiamidate)-sulfonyl)-propionyl-(R)-phenylglycine (TLK286) and $O^2$-[2,4-dinitro-5-(N-methyl-N-4-carboxyphenylamino) phenyl] 1-N,N-dimethylamino) diazen-1-ium-1,2-diolate (PABA/NO).

In another aspect, the invention provides a method of reducing toxicity of radiation and/or at least one chemotherapeutic agent administered to a patient undergoing cancer treatment, comprising
(i) administering an effective dose of CONPs to the patient,
(ii) administering a dose of radiation and/or at least one chemotherapeutic agent
wherein administering an effective dose of CONPs reduces the toxicity of radiation and/or at least one chemotherapeutic agent administered to the patient.

In a further aspect, the invention provides a method of decreasing a dose of radiation and/or at least one chemotherapeutic agent administered to a patient required to effectively treat a cancer, comprising
(i) administering an effective amount of CONPs to the patient,
(ii) administering a dose of radiation and/or at least one chemotherapeutic agent,
wherein administering an effective dose of CONPs reduces the dose of radiation and/or at least one chemotherapeutic agent required to effectively treat cancer.

The chemotherapeutic agent may be selected based upon its specificity and potency of inhibition of a cellular pathway target to which cancer cells in the patient may be susceptible. In practicing the invention, the chemotherapeutic agent may be selected by its ability to inhibit a cellular pathway target selected from the group consisting of mTORC, RAF kinase, MEK kinase, Phophoinositol kinase 3, Fibroblast growth factor receptor, multiple tyrosine kinase, Human epidermal growth factor receptor, vascular endothelial growth factor, other angiogenesis, heat shock protein; Smo (smooth) receptor, FMS-like tyrosine kinase 3 receptor, Apoptosis protein inhibitor, cyclin dependent kinases, deacetylase, ALK tyrosine kinase receptor, serine/threonine-protein kinase Pim-1, Porcupine acyltransferase, hedgehog pathway, protein kinase C, mDM2, Glypciin3, ChK1, Hepatocyte growth factor MET receptor, Epidermal growth factor domain-like 7, Notch pathway, Src-family kinase, DNA methyltransferase, DNA intercalators, Thymidine synthase, Microtubule function disruptor, DNA cross-linkers, DNA strand breakers, DNA alkylators, JNK-dependent p53 Ser15 phosphorylation inducer, DNA topoisomerase inhibitors, Bcl-2, and free radical generators.

In exemplary embodiments, the method further comprises performing a surgical procedure at the cancer site.

In one embodiment, the surgical procedure is performed at the cancer site before administration of the radiation.

In one embodiment, the surgical procedure is performed at the cancer site after administration of the radiation.

In one embodiment, the surgical procedure is performed at the cancer site before administration of the chemotherapeutic agent.

In one embodiment, the surgical procedure is performed at the cancer site after administration of the chemotherapeutic agent.

BRIEF DESCRIPTION OF THE DRAWINGS

FIGS. 22A to 22E illustrate radiation-induced pneumonitis and tolerance for cerium oxide nanoparticles in mice at different levels of radiation: 0 Gy (FIG. 22A), 12 Gy (FIG. 22B), 15 Gy (FIG. 22C), and 18 Gy (FIG. 22D), and survival under varying conditions with and without radiation, cerium oxide nanoparticles, and Amifostine (FIG. 22E).

FIGS. 23A to 23H illustrate tissue sections under varying conditions with and without radiation, cerium oxide nanoparticles, and Amifostine.

FIGS. 25A and 25B illustrate cerium oxide nanoparticles (CONPs) selectively increase RT induced ROS in pancreatic cancer cells, wherein FIG. 25A illustrates In L3.6pl and hTERT-HPNE cells pre-incubated with CONPs. FIG. 25B illustrates CONPs added after radiation, and FIGS. 25C to 25D illustrate changes in ROS level.

FIGS. 26A to 26D illustrate CONPs selectively sensitize pancreatic cancer cells to radiation in vitro, wherein FIG. 26A illustrates pre-treatment of L3.6pl cells with 10 μM CONPs, FIG. 26B pre-treatment of normal pancreatic cells (HPNE) with 10 μM CONPs, FIG. 26C pre-treatment of L3.6pl cells with 10 μM CONPs, and FIG. 26D illustrates the changes in colony formation.

FIGS. 28A to 28C illustrate physiochemical properties of the synthesized nanoparticles, wherein FIG. 28A illustrates HRTEM image of nanoceria showing nanoparticles size range of 3-5 nm, in the inset high magnification image of the nanoparticle, FIG. 28B illustrates a SEAQ pattern of a the fluorite crystal structure where A, B, C and D corresponds to different lattice pattern 111, 200, 220 and 311, respectively, and FIG. 28C illustrates the hydrodynamic radius of the nanoparticle in the size range of between about 3 nanometers to about 20 nanometers (CONP size distribution mode is about 10 nanometers).

FIGS. 29A to 29C illustrate radiation effects on salivary production in the absence and presence of cerium oxide nanoparticles, wherein FIG. 29A illustrates stimulated sialometry analysis of salivary gland function 6 weeks after single fraction radiation to the head and neck area (12.5 Gy, 15 Gy, 17.5 Gy or 20 Gy), FIG. 29B the effects of nanoceria on salivary flow protection after radiation exposure, and FIG. 29C the effects of nanoceria on skin hyperpigmentation after radiation exposure using the NCI common terminology criteria for adverse events (CTCAE v.3.0).

FIGS. 31A and 31B illustrate effects of CONPs on the apoptotic index of salivary glands parenchymal cells after radiation to the head and neck region, wherein FIG. 31A illustrates radiation induced apoptosis of salivary glands parenchymal cells, and FIG. 31B complementary analysis of the effects of CONPs combined with radiation on all major salivary glands yielded a similar response as that shown in FIG. 31A.

DETAILED DESCRIPTION OF THE INVENTION

Figure 1:
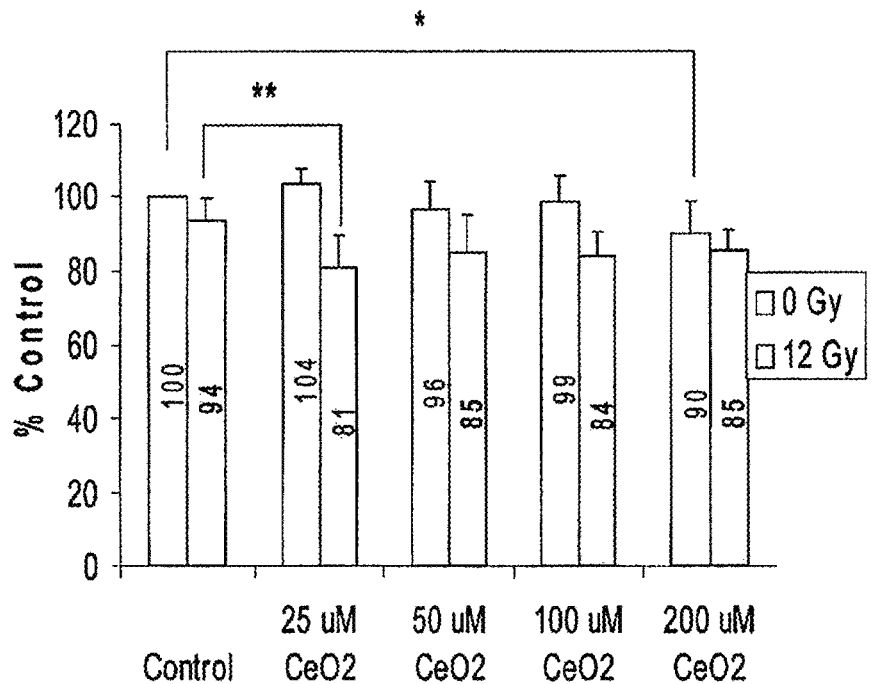
FIGS. 1 and 2 are graphs of the results of 24 h (FIG. 1) and 48 h (FIG. 2) MTT assays to determine the effect of cerium oxide nanoparticles on L3.6pl human pancreatic cancer cells.

The present invention is directed to treatment of cancer in a patient in need thereof with a combination of radiation, cerium oxide nanoparticles (CONPs), and at least one chemotherapeutic agent. The invention is a method of treating a cancer in a patient in need thereof, comprising: administering an effective dose of cerium oxide nanoparticles to the patient; administering a therapeutically effective dose of radiation to the patient and administering a therapeutically effective dose of a chemotherapeutic agent to the patient, thereby treating the cancer. The administration of the CONPs increases efficacy of radiation and/or chemotherapeutic treatment, lowers the therapeutically effective dose of radiation and/or lowers the therapeutically effective dose of the one or more chemotherapeutic agents needed to treat the cancer in the patient. When CONPs are delivered the optimal therapeutic outcome is achieved with even less radiation and chemotherapy than normally used without CONPs. Therefore the administration of CONPs will indirectly or directly lower the toxicity associated with the higher doses of radiation and chemotherapy most often used when administered without the CONPs.

I. Definitions

Where a term is provided in the singular, the inventors also contemplate aspects of the invention described by the plural of that term. As used in this specification and in the appended claims, the singular forms "a", "an" and "the" include plural references unless the context clearly dictates otherwise, e.g., "a tip" includes a plurality of tips. Thus, for example, a reference to "a method" includes one or more methods, and/or steps of the type described herein and/or which will become apparent to those persons skilled in the art upon reading this disclosure.

The term "administer", "administering" or "administered" means refers to the act of giving an agent or therapeutic treatment to a physiological system (e.g., a subject or in vivo, in vitro, or ex vivo cells, tissues, and organs).

The term "diagnosed", "diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein, the terms "treat", "treatment" and "treating" refer to the reduction or amelioration of the progression, severity, and/or duration of cancer, particularly a solid tumor, or one or more symptoms thereof that results from the administration of one or more therapies (e.g., one or more prophylactic and/or therapeutic agents). In exemplary embodiments, treatment of a solid tumor refers to one or more of (i) reducing the number of cancer cells; (ii) increasing tumor cell apoptosis; (iii) reducing tumor size; (iv) reducing tumor volume; (v) inhibiting, retarding, slowing to some extent, and preferably stopping cancer cell infiltration into peripheral organs; (vi) inhibiting (e.g., slowing to some extent and preferably stopping) tumor metastasis; (vii) inhibiting tumor growth; (viii) preventing or delaying occurrence and/or recurrence of a tumor; (ix) reduction of a cancer marker that is associated with the presence of cancer; and/or (ix) relieving to some extent one or more of the symptoms associated with the cancer. "Treatment" can also mean prolonging survival as compared to expected survival if not receiving treatment. In some embodiments, the method of the present invention is sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of cancer cells, or tumor growth rate compared to treatment in the absence of CONPs. Standard methods can be used to measure the magnitude of this effect, such as in vitro assays with purified enzyme, cell-based assays, animal models, or human testing. For example, an immunohistochemical analysis of a cancer tumor of the patient may show a significant increase in tumor cell apoptosis when the present invention is administered to the patient. A chemical analysis of a cancer tumor of the patient may show a significant increase in cancer cell reactive oxygen species levels when CONPs and radiation are administered to the cancer patient.

As used herein, the term "effective amount" refers to the amount of a therapy (e. g. a prophylactic or therapeutic agent) which is sufficient to effect beneficial or desired results, including clinical results. An effective amount can be administered in one or more administrations. When used with reference to cerium oxide nanoparticles, or a composition thereof, "effective amount" refers to the amount necessary to permit a reduction in the therapeutically effective amount of radiation and/or chemotherapeutic agent administered to the patient and/or the amount of reference to the amount of cerium oxide nanoparticles, or a composition thereof, necessary to have a desired therapeutic effect (e.g., treat radiation damage).

As used herein, the term "therapeutically effective amount" refers to that amount of a therapy which is sufficient to destroy, modify, control or remove primary, regional or metastatic cancer tissue, ameliorate cancer or one or more symptoms thereof, or prevent the advancement of cancer, cause regression of cancer, or enhance or improve the therapeutic effect (s) of another therapy (e. g., a prophylactic or therapeutic agent). A therapeutically effective amount can be administered in one or more administrations.

The term "subject" or "patient" or synonym thereto, as used herein includes all members of the animal kingdom, especially mammals, including human. The subject or patient is suitably a human.

The term "pharmaceutically acceptable carrier" refers to any such carriers known to those skilled in the art to be suitable for the particular mode of administration. For example, the term "pharmaceutically acceptable carrier" includes any and all solvents, dispersion media, coatings, antibacterial and antifungal agents, isotonic and absorption delaying agents and the like, that may be used as a media for a pharmaceutically acceptable substance. In addition, the active materials can also be mixed with other active materials that do not impair the desired action, or with materials that supplement the desired action, or have another action.

As used herein, the terms "cancer," "tumor" and "neoplasm" are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient.

As used herein, the terms "metastasis," "metastases," "metastatic," and other grammatical equivalents as used herein refer to cancer cells that spread or transfer from the site of origin (e.g., a primary tumor) to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures. The terms also refer to the process of metastasis, which includes, but is not limited to detachment of cancer cells from a primary tumor, intravasation of the tumor cells to circulation, their survival and migration to a distant site, attachment and extravasation into a new site from the circulation, and microcolonization at the distant site, and tumor growth and development at the distant site.

II. Cerium Oxide Nanoparticles

Cerium oxide nanoparticles (CONPs) are nanometer-sized crystals of cerium oxide, typically ranging between about one nanometer to about 20 nanometers in size in the longest dimension. Cerium oxide crystals have a fluorite-type crystal lattice and the cerium atoms are present in +3 or +4 valence states. The relative prevalence of the +3 or +4 valence states may depend upon the redox conditions and many other factors. In the present invention, CONPs are used to enhance radiation-induced and chemotherapy-induced cancer cell death. CONPs increase free radical levels in cancer cells and increase free radical levels in cancer cells beyond the level caused by the radiation alone. In addition, the combination of cerium oxide nanoparticles with radiation has also been found to control and/or minimize the metastatic index in animal cancer patient studies. The metastatic index is an indicator of severity of the cancer in a patient which assessment includes the number and size of metastases based upon an identification of metastatic foci. Combined with chemotherapy, the combination increases efficacy of treatment.

The dose of CONPs that may be administered to the patient may be tested by measuring blood plasma pharmacokinetics parameters using patient blood plasma sampling. Measured might be patient blood plasma CONP concentration variables such as the peak CONP concentration ($C_{max}$), time to $C_{max}$ ($T_{max}$) through CONP concentration ($C_{min}$), $T_{1/2}$ CONP concentration decline in patient's blood plasma, average CONP concentrations (average based on an integration of the CONP levels over several $T_{1/2}$ of the CONPs or over a week of treatment).

For example, in the practice of the present invention, the dose of CONPs that may be administered to the patient to provide an effective anti-cancer blood plasma concentration of the CONPs in the patient, may be between about 1 nanomolar to about 500 micromolar, or about 5 nanomolar to about 250 micromolar, or about 10 nanomolar to about 100 micromolar, or about 10 nanomolar to about 50 micromolar, or about 10 nanomolar to about 10 micromolar, or about 10 nanomolar to about 1 micromolar, or about 10 nanomolar to about 500 nanomolar, or about 10 nanomolar to about 100 nanomolar.

In terms of the dose of CONPs administered to a patient based on nanograms (ng) CONPs per kilogram patient body weight (CONP ng/kg), the dose of CONPs that may be administered to the patient may range between about 1 nanogram/kg to about 50 milligrams/kg, or about 1 nanogram/kg to about 10 milligrams/kg, or about 1 ng/kg to about 1 mg/kg, or about 1 ng/kg to about 500 micrograms/kg, or about 1 ng/kg to about 100 micrograms/kg, or about 1 ng/kg to about 10 micrograms/kg, or about 10 ng/kg to about 10 micrograms/kg, or about 10 ng/kg to about 1 micrograms/kg, or about 25 ng/kg to about 500 ng/kg, or about 25 ng/kg to about 250 ng/kg, or about 0.01 ng/kg to about 1 micrograms/kg, or about 0.1 ng/kg to about 500 ng/kg, or about 25 ng/kg to about 150 ng/kg.

In one aspect, the method permits a reduced dose of radiation or chemotherapy than either (i) the current standard of care in the absence of CONPs or (ii) the effective amount to treat the tumor in the absence of CONPs. In various embodiments, the dose of radiation or chemotherapeutic agent is between about 1% and 90%, or between about 1% and 80%, or between about 1% and 70%, or between about 1% and 60%, or between about 1% and 50%, or between about 1% and 40%, or between about 1% and 30%, or between about 1% and 20%, or between about 1% and 10% of either (i) the dose used in the current treatment standard in the absence of CONPs or (ii) the effective amount to treat the tumor in the absence of CONPs. In other embodiments, the dose of radiation or chemotherapy is between about 10% and 90%, or between about 20% and 80%, or between about 30% and 70%, or between about 40% and 60%, or between about 10% and 50%, or between about 10% and 30%, or between about 50% and 90%, or between about 70% and 90%.

CONPs are preferably used that have a size dimension that is between about 1 nanometer to about 3 nanometers, or about 1 nanometer to about 10 nanometers, or about 3 nanometers to about 10 nanometers, or about 3 nanometers to about 7 nanometers, or about 3 nanometers to about 5 nanometers, or about 3 nanometers to about 20 nanometers, or about 0.1 nanometers to about 100 nanometers, or about 0.1 nanometers to about 5 nanometers, or about 3 nanometers to about 50 nanometers. The CONP size can be determined by known methods and may include size measurements based upon various microscopic methods, light scattering or x-ray diffraction techniques.

Any known method can be used to make the cerium oxide nanoparticles (CONPs) or they can be purchased from various vendors. The purity and crystallinity of the CONPs can be adjusted by known methods in the art. CONPs may be doped with various ions such as for example cations of gold, silver, titanium, calcium, magnesium, cesium, iron, manganese, copper, zinc, strontium, lanthanum, carbon, selenium, chromium, aluminum, potassium, sodium, lead, organic amines; and for example anions of atoms of nitrogen, sulfur, fluorine, chloride, bromine, iodine, carbon, and for example organic acid anions. The CONPs may be coated with polymers, carbohydrates, proteins, polymers in a passive manner, or through chemical bonding including covalent, ionic, polar covalent, coordination complexes, hydrogen bonding, Van der Waals forces, electrostatic, magnetic, or any combination thereof.

In addition, CONPs may be created chemically under different pH conditions to shift the relative amounts of $Ce^{+3}$ and $Ce^{+4}$ in the CONP crystals. For CONPs that are crystallized or present as crystals of sub-nanometer to multi-micron dimensions, it is contemplated that in the presence of reducing agents, that the CONP $Ce^{+3}$ to $Ce^{+4}$ ratio is increased. Similarly this $Ce^{+3}$ to $Ce^{+4}$ ratio is contemplated to increase at a pH alkaline to pH 6.5. Conversely when CONPs are crystallized or present as crystals of sub-nanometer to multi-micron dimensions, it is contemplated that in the presence of oxidizing agents, that the CONP $Ce^{+3}$ to $Ce^{+4}$ ratio is decreased. Similarly the $Ce^{+3}$ to $Ce^{+4}$ ratio is contemplated to be decreased at a pH acidic to pH 6.5.

CONPs can scavenge free radicals to protect skin from radiation-induced dermatitis and enhance radiation-induced cancer cell death, while at the same time protecting normal tissue from radiation. CONPs protect normal tissue subjected to irradiation from inflammation, and protect cells from reactive oxygen species (ROS). In addition, CONPs can kill cancer cells by increasing free radical levels in cancer cells.

The teachings of the present invention provide a novel method for treating cancer using CONPs combined with chemotherapy and radiation therapy while minimizing damage to normal non-cancer tissue. As such, the use of CONPs with combined chemotherapy/radiation treatment provide more effective treatment, or alternatively equally effective treatment using reduced doses of radiation/chemotherapy than are used in the absence of CONPs. CONPs have been tested for their ability to serve as free radical scavengers to render protection against chemical, biological, and radiological insults that promote the production of free radicals. While not to be bound by a specific mechanism, it is believed that CONPs, with respect to valence and oxygen defects, promotes cell longevity and decreases toxic insults by virtue of its antioxidant properties, prevents the accumulation of reactive oxygen species (ROS), and thereby prevents the activation of the apoptotic response and cell death.

The safety and ability of CONPs to confer radioprotection in a murine model has been tested. CONPs are well tolerated and appear to decrease the incidence of pneumonitis in athymic nude mice. Examples of cerium oxide nanoparticles are described in U.S. Pat. Nos. 8,048,523, and 8,703,200 which are incorporated in their entirety by reference herein.

The cerium oxide nanoparticles may be administered as a composition comprising cerium oxide nanoparticles and a pharmaceutically acceptable carrier, as described in section IV, below.

III. Radiation

Methods of treating cancer with radiation are known to those in the art. Radiation therapy or radiotherapy is the medical use of ionizing radiation, generally as part of cancer treatment to control or kill malignant cells. Radiation therapy may be curative in a number of types of cancer if they are localized to one area of the body. It may also be used as part of adjuvant therapy, to prevent tumor recurrence after surgery to remove a primary malignant tumor (for example, early stages of breast cancer). Radiation therapy is synergistic with chemotherapy, and has been used before, during, and after chemotherapy in susceptible cancers.

The amount of radiation used in photon radiation therapy is measured in gray (Gy), and varies depending on the type and stage of cancer being treated. For curative cases, the typical dose for a solid epithelial tumor ranges from 60 to 80 Gy, while lymphomas are treated with 20 to 40 Gy.

In the present methods, the use of CONPs provides effective treatment with a lower dose of radiation. In another embodiment, the use of CONPs provides an increase in treatment efficacy at the same dose level of radiation currently used in the absence of CONPs. In one embodiment, the use of CONPs provides radioprotection for normal non-cancer cells during treatment and reduces side effects of radiation/chemotherapy treatment.

The total dose of radiation is often fractionated (spread out over time) for several important reasons. Fractionation allows normal cells time to recover, while tumor cells are generally less efficient in repair between fractions. Fractionation also allows tumor cells that were in a relatively radio-resistant phase of the cell cycle during one treatment to cycle into a sensitive phase of the cycle before the next fraction is given. Similarly, tumor cells that were chronically or acutely hypoxic (and therefore more radio-resistant) may re-oxygenate between fractions, improving the tumor cell kill.

Fractionation regimens are individualized between different radiation therapy centers and even between individual doctors. In North America, Australia, and Europe, the typical fractionation schedule for adults is 1.8 to 2 Gy per day, five days a week. In some cancer types, prolongation of the fraction schedule over too long can allow for the tumor to begin repopulating, and for these tumor types, including head-and-neck and cervical squamous cell cancers, radiation treatment is preferably completed within a certain amount of time. For children, a typical fraction size may be 1.5 to 1.8 Gy per day, as smaller fraction sizes are associated with reduced incidence and severity of late-onset side effects in normal tissues.

In some cases, two fractions per day are used near the end of a course of treatment. This schedule, known as a concomitant boost regimen or hyperfractionation, is used on tumors that regenerate more quickly when they are smaller. In particular, tumors in the head-and-neck demonstrate this behavior.

One fractionation schedule that is increasingly being used and continues to be studied is hypofractionation. This is a radiation treatment in which the total dose of radiation is divided into large doses. Typical doses vary significantly by cancer type, from 2.2 Gy/fraction to 20 Gy/fraction. The logic behind hypofractionation is to lessen the possibility of the cancer returning by not giving the cells enough time to reproduce and also to exploit the unique biological radiation sensitivity of some tumors. One commonly treated site where there is very good evidence for such treatment is in breast cancer. Short course hypofractionated treatments over 3-4 weeks e.g. 40Gy in 15 fractions or 42.5Gy in 16 fractions, have been shown to be as effective as more protracted 5-6 week treatments with respect to both cancer control and cosmesis (restoration of patient appearance). Those skilled in the art will appreciate the treatment schedules and how to vary the dosage and treatment schedules in combination with the present methods.

Preventive (adjuvant) doses (meaning therapy applied after initial treatment for the cancer) are typically around 45-60 Gy in 1.8-2 Gy fractions (for breast, head, and neck cancers.) Many other factors are considered by radiation oncologists when selecting a dose, including whether the patient is receiving chemotherapy, patient comorbidities, whether radiation therapy is being administered before or after surgery, and the degree of success of surgery.

Delivery parameters of a prescribed dose are determined during treatment planning (part of dosimetry). Treatment planning is generally performed on dedicated computers using specialized treatment planning software. Depending on the radiation delivery method, several angles or sources may be used to sum to the total necessary dose. The skilled practitioner designs a plan that delivers a uniform prescription dose to the tumor and minimizes dose to surrounding healthy tissues and side effects.

IV. Cancer Chemotherapeutic Agents

For some embodiments of the present invention, it is contemplated that chemotherapeutic drug delivery can be controlled to optimize anti-cancer therapy and to minimize side effects to the cancer patient being treated by the chemotherapeutic agent. A treatment of cancer tumors needs to optimize the kill of the cancer cell population or may cause more harm and stimulate cancer cell proliferation. The drug administration variables include: (a) timing of chemotherapy administration; (b) drug dosages; (c) types of cancer drugs administered; and (d) duration of drug therapy.

It is an important embodiment of the present invention to use a cancer treatment in the patient which is an administration of a dose of cerium oxide nanoparticles (CONPs) alone, or in combination with a dose of a second chemotherapeutic agent, or further includes a radiation treatment of the patient, to treat a cancer or risk of a cancer.

The present invention contemplates combining CONP, radiation anti-cancer therapy and a cancer chemotherapeutic agent as an effective anti-cancer treatment in a patient. In addition, an anti-cancer treatment of a patient who may have cancer, or for prophylactic purposes, or has a diagnosed cancer may comprise in accordance with the present invention, administering CONPs with a chemotherapeutic agent in combination with radiation therapy. Dosing of these agents may be according to separate dose administration schedules. The dose and frequency of dosing for each anti-cancer agent may be tailored based on patient body weight, type of cancer, cellular target inhibited by the agent, or with the intention of achieving a selected plasma blood level of the anti-cancer agent thought needed for an effective anti-cancer treatment of the patient by the anti-cancer agent. Such a dose may be determined using published guidelines on calculating dose of chemotherapeutic agent (See Gurney, H., Br J Cancer. Apr. 22, 2002; 86(8): 1297-1302).

Cancer Drugs and Cancer Chemotherapeutic Agents are general terms with a meaning that includes the terms cancer drug, cancer chemotherapeutic drugs, cancer agent, cancer chemotherapy, chemotherapeutic drug, chemotherapeutic agent, chemotherapy, chemotherapy drug, cancer compound, cancer compound therapy, chemotherapy compound, and cancer drug therapies. Such chemotherapies shall also mean a chemical substances that: may inhibit cancer cellular pathways; that may be used to kill cancer cells in vitro; that may be used to kill cancer cells in vivo, as in cancer tumors; and in some cases may be used to treat a person diagnosed with cancer to protect viability of the cancer patient's normal cells or attack the viability of the cancer patient's cancer cells.

By way of serving only as examples without intending to limit the scope of the present invention, and to more particularly point out the practice of the present invention are the following examples and applications of the chemotherapy agents. A number of cellular pathways that may be targeted by cancer chemotherapeutic drugs will also be described. Generally a cancer chemotherapeutic drug is used in the form of a pharmaceutical composition, for a pharmaceutical use, or in a method of treatment of as patient.

Examples of Cancer Chemotherapeutic Drugs/Agents/Compounds

Table 1 presents examples of common chemotherapy agents used in the treatment of six common types of cancer in a human patient.

TABLE 1

Examples of Possible Chemotherapy Agents Used in a Cancer Treatment

| Cancer Type | Chemotherapy Agent |
| --- | --- |
| Head and Neck | Carboplatin, Fluorouracil, Vinblastine |
| Pancreas | Gemcitabine, Cyclophosphamide, Doxorubicin, Fluorouracil |
| Lung | Methotrexate, Paclitaxel, Topotecan, Carboplatin, Etoposide |
| Breast | Methotrexate, Paclitaxel, Fluorouracil |
| Colon | Irinotecan, Fluorouracil |

Examples of FDA approved cancer drugs (by generic name) which can be used in the present invention include but are not limited to: sorafenb, regorafenib, imatinib, eribulin, gemcitabine, capecitabine, pazopanib), lapatinib, dabrafenib, sutinib malate, crizotinib, everolimus, torisirolimus, sirolimus, axitinib, gefitinib, anastrole, bicalutamide, fulvestrant, ralitrexed, pemetrexed, goserilin acetate, erlotininb, vemurafenib, visiodegib, tamoxifen citrate, paclitaxel, docetaxel, cabazitaxel, oxaliplatin, ziv-aflibercept, bevacizumab, trastuzumab, pertuzumab, pantiumumab, taxane, bleomycin, melphalen, plumbagin, camptosar, mitomycin-C, doxorubicin, pegylated doxorubicin, Folfori, 5-fluorouracil, temozolomide, pasireotide, tegafur, gimeracil, oteraci, itraconazole, bortezomib, lenalidomide, and romidepsin.

Generic names of cancer chemotherapeutic drugs that have been typically used in cancer patients include but are not limited to: doxorubicin, epirubicin; 5-fluorouracil, paclitaxel, docetaxel, cisplatin, bleomycin, melphalen, plumbagin, irinotecan, mitomycin-C, and mitoxantrone. By way of example, some other cancer chemotherapeutic drugs that may be used and may be in stages of clinical trials include: resminostat, tasquinimod, refametinib, lapatinib, Tyverb, Arenegyr, pasireotide, Signifor, ticilimumab, tremelimumab, lansoprazole, PrevOnco, ABT-869, linifanib, tivantinib, Tarceva, erlotinib, Stivarga, regorafenib, fluorosorafenib, brivanib, liposomal doxorubicin, lenvatinib, ramucirumab, peretinoin, Ruchiko, muparfostat, Teysuno, tegafur, gimeracil, oteracil, and orantinib.

Cellular Targets of Chemotherapeutic Drugs/Agents/Compounds

The chemotherapeutic agents may be selected based on the type of cancer suffered by the cancer patient in order to kill that cancer in the patient. Cancer chemotherapy drugs may be selected which inhibit a specific cellular pathway target or multiple targets. A cancer drug for the present invention includes molecules that are small organic molecules, salts, ions, gases, liquids, peptides, even large proteins such as antibodies.

Examples of cellular targets at which a cancer drug may have an effect are listed here, but are not limiting. The cellular targets of cancer drugs include the following identified targets: mTORC, RAF kinase, MEK kinase, Phophoinositol kinase 3, Fibroblast growth factor receptor, Multiple tyrosine kinase, Human epidermal growth factor receptor, Vascular endothelial growth factor, Other angiogenesis factors, Heat shock protein; Smo (smooth) receptor, FMS-like tyrosine kinase 3 receptor, Apoptosis protein inhibitor, Cyclin dependent kinases, Deacetylase, ALK tyrosine kinase receptor, Serine/threonine-protein kinase Pim-1, Porcupine acyltransferase, Hedgehog pathway, Protein kinase C, mDM2, Glypciin 3, ChK1, Hepatocyte growth factor MET receptor, Epidermal growth factor domain-like 7, Notch pathway, Src-family kinase, DNA methyltransferase, DNA intercalators, Thymidine synthase, Microtubule function disruptor, DNA cross-linkers, DNA strand breakers, DNA alkylators, JNK-dependent p53 Ser15 phosphorylation inducer, DNA topoisomerase inhibitors, Bcl-2, and free radical generators.

1. Chemotherapy Using mTOR Inhibitors, PI3K Inhibitors, Mulit-Kinase Inhibitors

There are mTORC Inhibitors to treat cancer. A mammalian Target of Rapamycin Complex (mTORC) inhibitor may inhibit mTOR, mTORC1, and/or mTORC2. Some mTORC inhibitors also inhibit other cell enzymes such as for example PI3K (phosphoinositol 3-kinase). The mTOR Complex 1 (mTORC1) is composed of: mTOR; a regulatory-associated protein of mTOR (Raptor); a mammalian lethal with SEC13 protein 8 (MLST8); PRAS40; and DEPTOR. The catalytic subunit of the two molecular complexes mTORC1 and mTORC2 is mTOR which belongs to the phosphatidylinositol 3-kinase-related kinase protein family. The mTORC1 is a nutrient/energy/redox sensor and controls protein synthesis. When there is an adequate cellular levels of energy, nutrients, oxygen, and cell growth factors, then mTORC1 is activated. The mTORC1 activation activates protein synthesis. Some kinds of cancer cells have abnormal functioning mTOR, mTORC1 or mTORC2 proteins.

Examples of mTORC inhibitors include AP23573 (deforolimus, ridaforolimus), AZD2014, AZD8055, CCL-779 (temsirolimus, NSC-683864), CH5132799, GDC-0941), GDC-0349, GSK2126458 (GSK458), GSK2126458 (GSK458), GSK1059615, INK128, Ku-0063794, NVP-BEZ235, NVP-BGT226, OSI-027 (ASP4786), Palomid 529 (P529), PI-103, PP121, PP242, PK1587, PF04691502, PF-05212384 (PKI-587), Rapamycin (sirolimus), RAD001 (everolimus), RG7422 (GDC0980), RG7321 (Pictilisib, SAR245409, XL-765), RG7440, SF1126, SF1101, Torin 1, Torin 2, WAY-600, WYE-125132 (WYE-132), WYE-354, and WYE-687. Rapamycin (sirolimus) (Rapaimmune, Wyeth-Ayerst) inhibits mTORC1 by associating with its intracellular receptor FKBP12. The FKBP12-rapamycin complex binds directly to the FKBP12-Rapamycin Binding (FRB) domain of mTOR, inhibiting its activity.

Second generation mTORC inhibitors are able to bind to the ATP-binding motif on the kinase domain of the mTOR core protein and this binding blocks the activity of both mTORC1 and mTORC2. As the mTOR and the PI3K proteins are related to phosphatidylinositol 3-kinase-related kinases (PIKK), some second generation mTORC inhibitors are more direct in their inhibition of mTOR, mTORC1 or mTORC2. Some of these compounds also inhibit PI3K (phosphatidylinositol 3-kinase) which acts "upstream" of mTORC1.

Everolimus (Afinotor, Novartis) is a mTORC1/2 inhibitor. CCL-779 (temsirolimus, NSC-683864) (Torisel,Wyeth-Ayerst/Pfizer) is a mTORC1/2 inhibitor. AP23573 (deforolimus, ridaforolimus, MK-8669) (Ariad/Merck) is a mTORC1/2 inhibitor. PI-103 is a mTORC1, mTORC2 and PI3K/Akt inhibitor. PP121 is a multi-target inhibitor of PDGFR, Hck, mTOR, VEGFR2, Src, Abl, and DNA-PK. BEZ235 is a PI3K/mTOR inhibitor. GSK2126458 (GSK458) is a PI3K/mTOR inhibitor. GSK2126458 (GSK458) is a mTORC1 and mTORC2 inhibitor. Ku-0063794 is a mTORC1 and mTORC2 inhibitor. SAR245409 (XL-765) is a PI3K/mTOR inhibitor. SF1126 (SF stands for Semafore Pharmaceuticals) is prodrug containing the pan-PI3K/mTOR inhibitor LY294002/SF1101 which is conjugated to the RGD-containing tetra-peptide SF1174. The targeting peptide SF1174 moiety of pan-PI3K/mTOR inhibitor SF1126 selectively binds to cell surface integrins and, upon cell entry, the agent is hydrolyzed to the active drug SF1101. SF-1101 (LY294002) is a PI3K/mTOR inhibitor. PP242 is an ATP-competitive inhibitor against both mTORC1 & mTORC2. INK-128 (MLN-0128) (IN stands for Intellikine) is a mTORC1/2 inhibitor, an inhibitor of raptor-mTOR (TOR complex 1 or TORC1) and rictor-mTOR (Note that mTOR is also part of a distinct complex defined by the novel protein rictor (rapamycin-insensitive companion of mTOR) which modulates the phosphorylation of Protein Kinase C alpha (PKCalpha) and the actin cytoskeleton. AZD-8055 (AZ stands for Astra-Zeneca) is an inhibitor of mTOR. NVP-BGT226 is a novel dual PI3K/mTOR inhibitor. RG7666 (GDC-0084) is a PI3 kinase inhibitor of the PI3K/Akt/mTOR pathway. RG7422 (GNE 390; GDC-0980) is a PI3K/mTOR dual inhibitor. PF-05212384 (PKI-587) is a PI3K/mTOR inhibitor. PF04691502 is an mTOR and a PI3K inhibitor. RG7321 (Pictilisib, GDC-0941) is a PI3K/mTOR inhibitor. GDC-0349 is an mTOR inhibitor. Torin 1 is a mTORC1 and mTORC2 inhibitor. Torin 2 is a mTOR inhibitor and a ATM/ATR/DNA-PK inhibitor. AZD2014 is a dual mTORC1 and mTORC2 inhibitorCH5132799 is a mTOR and a PI3K inhibitor. WAY-600 is a mTORC inhibitor. WYE-125132 (WYE-132) is a mTORC inhibitor. WYE-687 is a mTORC inhibitor. Palomid 529 (P529) is a PI3K/Akt/mTOR inhibitor for VEGF-A and bFGF. GSK1059615 is a novel and dual inhibitor of PI3Kα, PI3KIβ, PI3Kδ, PI3Kγ and mTOR. WYE-354 is an inhibitor of mTOR.

2. Chemotherapy Using RAF Kinase Inhibitors of RAS-RAF-MEK-ERK (MAPK/ERK) Pathway The RAS-RAF-MEK-ERK (MAPK/ERK) pathway is a chain of interacting proteins which transfer cell surface receptor activity to induce DNA activity in the cell nucleus to make proteins and promote cellular changes such as cell division. MAPK (Mitogen-activated protein kinases) was previously called ERK (Extracellular signal-regulated kinases). MAPK phosphorylates the pathway RAS-RAF-MEK proteins and this alteration can switch this pathway to be "on" or "off". Proteins of the Ras-Raf-MEK-ERK pathway may be mutated and then functionally be stuck either "on" or "off". Such dysfunctionality is an observed precursor to cell cancer. RAS is a family of five GTPases. About 20% of human cancers (as high as 90% in specific cancers) have Ras protein mutations related to an oncogene that causes constant Ras protein kinase activation which phosphorylates RAF protein (https://en.wikipedia.org/wiki/Ras_subfamily). RAF comprises a family of three serine-threonine-specific protein kinases A, B and C; known as ARAF, BRAF, CRAF. One mutant BRAF is known as V600E. Specific examples of RAF Kinase inhibitors include Sorafenib, RAF265, LGX818, SB590885, PLX4720, XL-281 and vemurafenib. Sorfenib (Nexavar, Bayer) is an inhibitor of several Tyrosine protein kinases (VEGFR and PDGFR) and Raf kinases C-Raf and B-Raf kinases. RAF265 is an inhibitor of B-Raf and VEGFR2 kinases. LGX818, SB590885, PLX4720, XL281, and Vemurafenib (PLX-4032, Zelboraf), are B-RAF inhibitors.

3. Chemotherapy Using MEK kinase Inhibitors of [RAS-RAF-MEK-ERK (MAPK/ERK)] Pathway Activated RAF kinases phosphorylate and activate MEK kinases: MEK1 and MEK2. MEK is also known as MAPKK. MEK is a tyrosine/threonine kinase that once activated, can phosphorylate and activate a mitogen-activated protein kinase (MAPK). MAPK is a serine/threonine-selective protein kinase. Specific examples of MEK inhibitors include CI-1040, MEK162, PD035901, selumetinib, refametinib, BAY-86-9766, RDEA119, Trametinib (GSK1120212), and XL518, RG7167, RG7420, 4. Chemotherapy Using PI3K (phosphoinositol 3-kinase) Inhibitors The PI3K pathway is an important signaling pathway for many cellular functions such as growth control, metabolism and translation initiation. A PI3K inhibitor often results in tumor suppression. There are a number of different classes and isoforms of PI3Ks. Class 1 PI3Ks have a catalytic subunit known as p110, with four types (isoforms)—p110 alpha, p110 beta, p110 gamma and p110 delta Inhibitors being studied for treatment of various cancers inhibit one or more isoforms of the class I PI3Ks. Specific examples of PI3K (phosphoinositol 3-kinase) inhibitors include BEZ235, BYL719, buparlisib, BKM120, INC280, RG7440, RG7604, RG7666(GDC-0084), RG7321, RG7422, PF-05212384 (PKI-587), and PF-04449913.

5. Chemotherapy Using FGFR Inhibitors (Fibroblast Growth Factor Receptor (FGFR)

Fibroblast growth factors (FGFs), are a family of growth factors involved in angiogenesis, wound healing, and embryonic development. The FGFs are heparin-binding proteins and interactions with cell-surface-associated heparin sulfate proteoglycans have been shown to be essential for FGF signal transduction. FGFs are key players in the processes of proliferation and differentiation of wide variety of cells and tissues. Fibroblast growth factor receptors (FGFR) on the surface of the cell can communicate a signal through the MAPK/ERK pathway chain of proteins in the cell to the DNA in the nucleus of the cell. The FGFR family has 4 members, FGFR1, FGFR2, FGFR3, and FGFR4. FGFRs consist of three extracellular immunoglobulin-type domains (D1-D3), a single-span trans-membrane domain and an intracellular split tyrosine kinase domain. Examples of FGRF inhibitors are BGJ398 and dovitinib.

6. Chemotherapy Using Multiple Tyrosine Kinase Inhibitors (TKI)

Tyrosine kinases are enzymes responsible for the activation of many proteins by signal transduction cascades. The proteins are activated by adding a phosphate group to the protein (phosphorylation). Tyrosine kinase inhibitors (TKI) are typically used as anti-cancer drugs. TKIs operate by four different mechanisms: they can compete with adenosine triphosphate (ATP), the phosphorylating entity, the substrate or both or can act in an allosteric fashion, namely bind to a site outside the active site, affecting its activity by a conformational change. TKIs are small molecular weight inhibitors of tyrosine phosphorylation, which do not inhibit protein kinases that phosphorylate serine or threonine residues and can discriminate between the kinase domains of the EGFR and that of the insulin receptor. It was further shown that in spite of the conservation of the tyrosine-kinase domains one can design and synthesize TKIs that discriminate between even closely related protein tyrosine kinases such as EGFR and its close relative HER2.

Specific examples of tyrosine kinase inhibitors include Nexavar, Strivarga, Sutent, Iressa, and Inlyta, sunitinib malate.

7. Chemotherapy Using HER (Human Epidermal Growth Factor Receptor) Inhibitors

Signaling pathways activated by HER2 include: mitogen-activated protein kinase (MAPK), phosphoinositide 3-kinase (PI3K/Akt), phospholipase C γ, protein kinase C (PKC) and signal transducer and activator of transcription (STAT). Signaling through the ErbB family of receptors promotes cell proliferation and opposes apoptosis, and therefore must be tightly regulated to prevent uncontrolled cell growth from occurring. Amplification or over-expression of the ERBB2 gene is strongly associated with increased disease recurrence and a poor prognosis. Over-expression is also known to occur in breast, ovarian, stomach, and aggressive forms of uterine cancer, such as uterine serous endometrial carcinoma. HER2 is co-localized, and, most of the time, co-amplified with the gene GRB7, which is a proto-oncogene associated with breast, testicular germ cell, gastric, and esophageal tumors. HER2 proteins have been shown to form clusters in cell membranes that may play a role in tumorigenesis. Specific examples of HER (human epidermal growth factor receptor) inhibitors include RG7116, RG1273 (pertuzumab, Perjeta®), RG3502 (trastuzumab emantasine, T-DMI), RG597 (trastuzumab, HERCEPTIN), RGA201 (RG7160), erlotinib (Tarceva®), dacomitinib (PF-00299804), PF-05280014 (Pfizer's biosimilar mAB to RG597).

8. Chemotherapy Using VEGF (Vascular Endothelial Growth Factor) Inhibitors

In order to grow larger, tumors need their own blood vessels, which they create by angiogenesis promoters such as VEGF. Drugs that interrupt the tumor angiogenesis process (angiogenesis inhibitors) show promise in treating cancer. When one angiogenesis promoter is blocked, cancers eventually grow blood vessels using another angiogenesis promoter. A tumor is a population of rapidly dividing and growing cancer cells. Mutations rapidly accrue within the population. These mutations provide functional variations that allow the cancer cells or a sub-population of cancer cells within a tumor, to develop a drug resistance and/or escape therapy. When solid cancers are small, they are supplied with nutrients by diffusion from nearby blood vessels. Tumors cannot grow larger than 2 mm without angiogenesis which brings in oxygen, brings in nutrients and serves as a waste pathway to take away the biological end products secreted by rapidly dividing cancer cells. Angiogenesis is also required for the spread of a tumor, or metastasis. Single cancer cells can break away from an established solid tumor, enter the blood vessel, and be carried to a distant site, where they can implant and begin the growth of a secondary tumor. There is evidence that the blood vessel in a given solid tumor may be a mosaic vessel composed of endothelial cells and tumor cells. The mosaic vessel might shed tumor cells into the vasculature to escape inflammation or ischemia caused by radiation Specific examples of VEGF (vascular endothelial growth factor) inhibitors include Strivarga (regorafenib), bevacizumab (Avastin), Inlyta, itraconazole and XL184 (cabozantinib). Regorafenib shows anti-angiogenic activity due to its dual targeted VEGFR2-TIE2 tyrosine kinase inhibition. Inlyta (axitinib) is a VEGF tyrosine kinase inhibitor. Natural and synthetic angiogenesis inhibitors include angiostatin, endostatin and tumstatin. The anti-angiogenic mechanism for bevacizumab and itraconazole is a direct binding to VEGF. Itraconazole also inhibits VEGFR phosphorylation, glycosylation, mTOR signaling, endothelial cell proliferation, cell migration, lumen formation, and tumor associated angiogenesis. XL184 (cabozantinib) is an inhibitor of the tyrosine kinases Met and VEGFR2, and has been shown to abrogate tumor growth, metastasis, and angiogenesis.

9. Chemotherapy Using Other Angiogenesis Inhibitors

There are other compounds and VEGF inhibitors that may inhibit some forms of angiogenesis. Anti-angiogenic compounds include: carboxyamidotriazole, TNP-470, CM101, IFN-α, IL-12, Platelet factor 4, angiostatic steroids plus heparin, matrix metalloproteinase inhibitors, angiostatin, endostatin, 2-methoxyestradiol, tecogalan, tetrathiomolybdate, thalidomide, thrombospondin, prolactin, αVβ3 inhibitors, and linomide. Carboxyamidotriazole inhibits cell proliferation and cell migration of endothelial cells. TNP-470 and CM101 activate the immune system. IFN-α downregulates angiogenesis stimulators and inhibit cell migration of endothelial cells. IL-12 (interleukin-12) stimulates angiogenesis inhibitor formation. Platelet factor-4 inhibits binding of angiogenesis stimulators. Angiostatic steroids plus heparin, and matrix metalloproteinase inhibitors inhibit basement membrane degradation. Angiostatin inhibits cell proliferation and induce apoptosis of endothelial cells. Endostatin inhibits cell migration, cell proliferation and survival of endothelial cells. The steroid 2-methoxyestradiol inhibit cell proliferation and cell migration and induce apoptosis of endothelial cells. Tecogalan inhibit cell proliferation of endothelial cells. Tetrathiomolybdate causes copper chelation which inhibits blood vessel growth. Thalidomide inhibit cell proliferation of endothelial cells. Thrombospondin inhibit cell migration, cell proliferation, cell adhesion and survival of endothelial cells. Prolactin inhibit bFGF and VEGF. The αVβ3 inhibitors induce apoptosis of endothelial cells. Linomide inhibits cell migration of endothelial cells.

10. Chemotherapy Using HSP (Heat Shock Protein) Inhibitors

Heat shock protein 90 (HspP90) is a molecular chaperone which regulates the folding and degradation of many proteins. Specific examples of HSP (heat shock protein) inhibitors include AUY922.

11. Chemotherapy Using Smo (Smooth) Receptor Inhibitors

The smoothened receptor (SMO) is part of the hedgehog signaling pathway. SMO inhibition causes the transcription factors GLI1 and GLI2 to remain inactive, which prevents the expression of tumor mediating genes within the hedgehog pathway. Sonic hedgehog is one of three proteins in the mammalian signaling pathway family called hedgehog, the others being desert hedgehog (DHH) and Indian hedgehog (IHH). SHH is the best studied ligand of the hedgehog signaling pathway. It plays a key role in regulating vertebrate organogenesis, such as in the growth of digits on limbs and organization of the brain. Sonic hedgehog is a morphogen which is a molecule that diffuses to form a concentration gradient and has different effects on the cells of the developing embryo depending on its concentration. SHH remains important in the adult. It controls cell division of adult stem cells and has been implicated in development of some cancers.

Specific examples of Smo (smooth) receptor inhibitors include Erivedge (vismodegib), erismodegib (LDE225), and LEQ506. Erivedge is a Smo receptor inhibitor FDA approved for basal cell carcinoma, and is also undergoing clinical trials for metastatic colorectal cancer, small-cell lung cancer, advanced stomach cancer, pancreatic cancer, medulloblastoma and chondrosarcoma. Erivedge acts as a cyclopamine-competitive antagonist of the smoothened receptor (SMO) which is part of the hedgehog signaling pathway. SMO inhibition causes the transcription factors GLI1 and GLI2 to remain inactive, which prevents the expression of tumor mediating genes within the hedgehog pathway.

12. Chemotherapy Using CD135 (FMS-Like Tyrosine Kinase 3 Receptor) Inhibitors

CD135 is a type III receptor tyrosine kinase. Cluster of differentiation antigen 135 (CD135) also known as Fms-like tyrosine kinase 3 (FLT-3), receptor-type tyrosine-protein kinase FLT3, or fetal liver kinase-2 (Flk2) is a protein that in humans is encoded by the FLT3 gene. Flt3 is a cytokine receptor which belongs to the receptor tyrosine kinase class III. CD135 is the receptor for the cytokine Flt3 ligand (Flt3L). CD135 is expressed on the surface of many hematopoietic progenitor cells. Signaling of Flt3 is important for the normal development of hematopoietic stem cells and progenitor cells. When this receptor binds to Flt3L it forms a dimer with itself (homodimer) that activates its intrinsic tyrosine kinase activity, which in turn phosphorylates and activates signal transduction molecules that propagate the signal in the cell. Signaling through CD135 plays a role in cell survival, proliferation, and differentiation. CD135 is important for lymphocyte (B cell and T cell) development. Specific examples of FLT-3 (tyrosine kinase receptor 3) inhibitors include INC280 (INCB028060), and midostaurin (PKC412). INC280 (INCB028060) inhibits c-Met (hepatocyte growth factor receptor [HGFR]) dependent PI3K and RAS signaling.

Midostaurin (PKC412) is used to inhibit mutated CD135 (FMS-like tyrosine kinase 3 receptor).

13. Chemotherapy Using Apoptosis Protein Inhibitors

Inhibitors of Apoptosis (IAP) are a family of functionally and structurally related proteins, which serve as endogenous inhibitors of programmed cell death (apoptosis). A common feature of all IAPB is the presence of a BIR (Baculovirus IAP Repeat, a ~70 amino acid domain) in one to three copies. The human IAP family consists of 8 members, and IAP homologs have been identified in numerous organisms. The first members of the IAPB identified were from the baculovirus IAPB, Cp-IAP and Op-IAP, which bind to and inhibit caspases as a mechanism that contributes to its efficient infection and replication cycle in the host. Five more human IAPB are XIAP, c-IAP1, C-IAP2, NAIP, and survivin. XIAP binds caspase-9, caspase-3 and caspase 7, thereby inhibiting their activation and preventing apoptosis. Note cIAP1 and cIAP2 bind caspases, although how the IAPB inhibit apoptosis mechanistically at the molecular level is not understood. An example of an Apoptosis protein inhibitor is LCL161.

14. Chemotherapy Using CDK 4/6 (Cyclin Dependent Kinases 4 and 6) Inhibitors

Cyclin-dependent kinases (CDKs) are a family of protein kinases involved in regulating transcription, mRNA processing, and differentiation. Present in all known eukaryotes, CDKs are small proteins kinase that bind a regulatory protein called a cyclin. The cyclin-CDK complex is an active serine-threonine kinase that phosphorylates their substrates on serines and threonines. Cyclin-dependent kinase 4 also known as cell division protein kinase 4 is an enzyme that in humans is encoded by the CDK4 gene. Mutations in this gene as well as in its related proteins including D-type cyclins, p16(INK4a) and Rb are all found to be associated with tumorigenesis of a variety of cancers. There are known to be 13 CDKs, listed here with their regulatory cyclin protein in brackets: CDK1 (cyclin A, cyclin B); CDK2 (cyclin A, cyclin E); CDK3 (cyclin C); CDK4 (cyclin D1, cyclin D2, cyclin D3); CDK5 (CDK5R1, CDK5R2); CDK6 (cyclin D1, cyclin D2, cyclin D3); CDK7 (cyclin H); CDK8 (cyclin C); CDK9 (cyclin T1, cyclin T2a, cyclin T2b, cyclin K); CDK10; CDK11 also known as CDC2L2 (cyclin L): CDK12 also known as CRKRS (cyclin L); and CDK13 also known as CDC2L5 (cyclin L). Specific examples of CDK 4/6 (cyclin dependent kinases 4 and 6) inhibitors include LEE011, PD-0332991 (palbociclib, PD-0332991-0054, PD-332991 and PF-00080665-73. Other CDK inhibitors include flavopiridol (alvocidib) [inhibits CDKs1, 2, 4, 6, 7, 9]; olomoucine [inhibits CDKs1, 2, 5]; roscovitine [inhibits CDKs 1, 2, 5]; purvalanol [inhibits CDKs 1, 2, 5]; paullones [inhibits CDKs 1, 2, 5]; butryolactone [inhibits CDKs 1, 2, 5]: thio/oxoflavopiridols [inhibits CDK 1]; oxindoles [inhibits CDK 2]; aminothiazoles [inhibits CDK 4]; benzocarbazoles [inhibits CDK 4]; pyrimidines [inhibits CDK 4]; and Seliciclib.

15. Chemotherapy Using DAC (Deacetylase) Inhibitors

Histone deacetylase inhibitors (HDAC inhibitors, HDIs) are a class of compounds that interfere with the function of histone deacetylase. The histone deacetylase inhibitors are a new class of cytostatic agents that inhibit the proliferation of tumor cells in culture and in vivo by inducing cell cycle arrest, differentiation and/or apoptosis. To carry out gene expression, a cell must control the coiling and uncoiling of DNA around histones. This is accomplished with the assistance of histone acetylases (HAT), which acetylate the lysine residues in core histones leading to a less compact and more transcriptionally active chromatin, and, on the converse, the actions of histone deacetylases (HDAC), which remove the acetyl groups from the lysine residues leading to the formation of a condensed and transcriptionally silenced chromatin. Reversible modification of the terminal tails of core histones constitutes the major epigenetic mechanism for remodeling higher-order chromatin structure and controlling gene expression. HDAC inhibitors (HDI) block this action and can result in hyperacetylation of histones, thereby affecting gene expression.

Resminostat (4SC-201) is an oral pan-HDACi. Specific DAC (deacetylase) inhibitors include panobinostat (LBH589), Vorinostat, Romidepsin (Istodax), Valproic acid (as magnesium valproate), Belinostat (PXD101), Mocetinostat (MGCD0103), Abexinostat (PCI-24781), Entinostat (MS-275), SB939, Resminostat (4SC-201, an oral pan-HDACi [tested for use in hepatocellular carcinoma], Givinostat (ITF2357), Quisinostat (JNJ-26481585), CUDC-101 (also inhibits EGFR and HER2), AR-42, CHR-2845, CHR-3996, 4SC-202, CG200745 for solid tumors, ACY-1215, selective for HDAC6 with bortezomib (Velcade) and with lenalidomide (Revlimid), ME-344, for solid refractory tumors, sulforaphane, and Kevetrin, selective for HDAC2.

16. Chemotherapy Using ALK Inhibitors

Anaplastic lymphoma kinase (ALK) also known as ALK tyrosine kinase receptor or CD246 (cluster of differentiation 246) is an enzyme that in humans is encoded by the ALK gene. The ALK gene can be oncogenic in three ways—by forming a fusion gene with any of several other genes, by gaining additional gene copies or with mutations of the actual DNA code for the gene itself. The EML4-ALK fusion gene is responsible for approximately 3-5% of non-small-cell lung cancer (NSCLC). The vast majority of cases are adenocarcinomas. Renal cell carcinoma is a result of such gene rearrangements and overexpression. Specific examples of ALK (anaplastic lymphoma) inhibitors include LDK378, RG7853, crizotinib (Xalkori), and PF-03446962 mAB.

17. Chemotherapy Using PIM Inhibitors

Proto-oncogene serine/threonine-protein kinase Pim-1 is an enzyme that in humans is encoded by the PIM1 gene. Proto-oncogene serine/threonine-protein kinase Pim-1 is an enzyme that in humans is encoded by the PIM1 gene for a PIM serine/threonine kinase. The oncogene has been implicated in multiple human cancers, and is highly expressed in cell cultures isolated from human tumors. Pim-1 is mainly involved in cell cycle progression, apoptosis and transcriptional activation, as well as more general signal transduction pathways, and has been implicated in many signal transduction pathways. Because Pim-1 translation is initiated by STAT3 and STAT5, its production is regulated by the cytokines that regulate the STAT pathway, or STAT factors. These include interleukins (IL-2, IL-3, IL-5, IL-6, IL-7, IL12, IL-15), prolactin, TNFα, EGF and IFNγ, among others. Specific examples of PIM (proto-oncogene serine/threonine-protein kinase) inhibitors include LGH447.

18. Chemotherapy Using Porcupine Acyltransferase Inhibitor

Porcupine is a member of the membrane-bound O-acyltransferase (MBOAT) family that adds the palmitoyl group to Wnt proteins, Wnt protein secretion and Wnt signaling ability. Breast tumors have also been seen to metastasize due to Wnt involvement in the epithelial-mesenchymal transition (EMT). The EMT process is what allows epithelial cells to transform into mesenchymal cells so that they are no longer held in place at the laminin. It involves a down-regulation of cadherins so that cells can detach from laminin and migrate Repression of Wnt/β-catenin signaling can prevent EMT, which can inhibit metastasis. Wnt signaling has also been implicated in the development of more than just breast-type cancers. Changes in CTNNB1 expression, which is the gene that encodes β-catenin, can be measured in not just breast cancer, but also colorectal cancer, melanoma, prostate cancer, lung cancer, and several other cancer types. Specific examples of Porcupine inhibitors include LGK974, XAV939, IWR-1, and IXP-2. BHQ880 is a phage-derived DKK1 neutralizing human immunoglobulinG1 (IgG1) antibody and an antagonist of the Wnt pathway.

19. Chemotherapy Using Hedgehog Pathway Inhibitors

The most common targeting of the hedgehog pathway modulates SMO (a 7 membrane spanning receptor called Smoothened). Antagonist and agonists of SMO affect the pathway regulation downstream. The most clinically advanced SMO targeting agents are cyclopamine-competitive. Itraconazole (Sporanox) has also been shown to target SMO through a mechanism distinct from cyclopamine and vismodegib. Itraconazole inhibits SMO in the presence of mutations conferring resistance to vismodegib and other cyclopamine-competitive antagonists, like IPI-926 and Novartis' LDE-225. PTCH, and Gli3 (5E1) antibodies also regulate the pathway. A downstream effector and strong transcriptional activator siRNA Gli1 has been used to inhibit cell growth and promote apoptosis. Arsenic trioxide (Trisenox) has also been shown to inhibit hedgehog signaling by interfering with Gli function and transcription.

Metastasis is activated by activation of the Hedgehog pathway as this leads to an increase in Snail protein expression and a decrease in E-cadherin and Tight Junctions. Hedgehog signaling is a crucial regulator of angiogenesis and thus metastasis. Tumor regulation is affected by activation of the Hedgehog pathway which leads to an increase in Angiogenic Factors (angiopoietin-1 and angiopoietin-2), an increase in Cyclins (cyclin D1 and B1), an increase in anti-apoptotic genes and a decrease in apoptotic genes (Fas). Specific examples of Hedgehog pathway inhibitors include Erivedge (RG3616), IPI-926, Sporonox (itraconazole), Trisenox (arsenic trioxide), LDE-225, PTCH and Gli3 (5E1) antibodies, and PF-04449913.

20. Chemotherapy Using PKC (Protein Kinase C) Inhibitors

Protein kinase C, activated by tumor promoter phorbol ester, may phosphorylate potent activators of transcription, and thereby lead to increased expression of oncogenes, promoting cancer progression. Protein kinase C iota type is an enzyme that in humans is encoded by the PRKCI gene. This gene encodes a member of the protein kinase C (PKC) family of serine/threonine protein kinases. The PKC family comprises at least eight members, which are differentially expressed and are involved in a wide variety of cellular processes such as microtubule dynamics in the early secretory pathway. This kinase is found to be necessary for BCL-ABL-mediated resistance to drug-induced apoptosis Specific examples of protein kinase C inhibitors include AEB071, ruboxistaurin, and ingenol mebutate.

21. Chemotherapy Using MDM2 Inhibitors

Mouse double minute 2 homolog (MDM2), also known as E3 ubiquitin-protein ligase Mdm2, is a protein that in humans is encoded by the MDM2 gene. Mdm2 is an important negative regulator of the p53 tumor suppressor. Mdm2 protein functions both as an E3 ubiquitin ligase that recognizes the N-terminal trans-activation domain (TAD) of the p53 tumor suppressor and an inhibitor of p53 transcriptional activation. Specific examples of MDM2 inhibitors include RG7112 and RG7388 Inhibitors of the MDM2-p53 interaction include the cis-imidazoline analog nutlin.

22. Chemotherapy Using Glypican-3 Inhibitors

Glypican-3 is a protein that in humans is encoded by the GPC3 gene. The protein encoded by this gene is a member of the glypican family. Cell surface heparin sulfate proteoglycans are composed of a membrane-associated protein core substituted with a variable number of heparin sulfate chains. Members of the glypican-related integral membrane proteoglycan family (GRIPS) contain a core protein anchored to the cytoplasmic membrane via a glycosyl phosphatidylinositol linkage. These proteins may play a role in the control of cell division and growth regulation. Glypican 3 immunostaining has utility for differentiating hepatocellular carcinoma (HCC) and dysplastic changes in cirrhotic livers; HCC stains with glypican 3, while liver with dysplastic changes and/or cirrhotic changes does not. Specific examples of glypican inhibitors include RG7687.

23. Chemotherapy Using ChK1 Inhibitors

Human checkpoint kinase 1 (Chk1) is an essential kinase required to preserve genome stability. Chk1 is required during normal S phase to avoid aberrantly increased initiation of DNA replication, thereby protecting against DNA breakage Inhibition or depletion of Chk1 causes a rapid and strong phosphorylation of ATR targets in S-phase cells, which is associated with increased initiation of DNA replication, massive induction of single stranded DNA, and generation of DNA strand breaks. Specific examples of ChK1 inhibitors include RG7602, RG7741, CEP-3891, and UCN-01.

24. Chemotherapy Using HGF/MET Inhibitors

The c-Met inhibitors inhibit the enzymatic activity of the c-Met tyrosine kinase, and have therapeutic application in the treatment of various types of cancers. Met tyrosine kinase is the receptor for hepatocyte growth factor (HGF a.k.a. scatter factor, SF). HGF is mostly expressed on epithelial cells and mesenchymal cells (e.g., smooth muscle cells and fibroblasts). HGF is normally active in wound healing, liver regeneration, embryo and normal mammalian development, and organ morphogenesis. c-Met dysregulation can be due to overexpression, gene amplification, mutation, a ligand-dependent auto- or paracrine loop or an untimely activation of RTK. All these factors affect the survival of cells, their proliferation and motility. They also lead to cancers and resistance to therapies which aim to treat them. Patients with aberrant c-Met activity usually have a poor prognosis, aggressive disease, increased metastasis and shortened survival. Specific examples of HGF/MET inhibitors include RG3638 (onartuzumab, METMAB), cabozantinib, AM7, SU11274, BMS-777607, PF-02341066, AMG-458, GSK 1363089 (XL880, foretinib), MK-2461. PF-04217903, and JNJ-38877605.

25. Chemotherapy Using EGFL7 (Epidermal Growth Factor Domain-Like 7) Inhibitors

EGF-like domain-containing protein 7 is a protein that in humans is encoded by the EGFL7 gene. Epidermal Growth Factor like domain 7 (Egfl7) also known as Vascular Endothelial-statin (VE-statin) codes for a gene mostly expressed in endothelial cells. An up-regulation of egfl7 is observed in endothelial cells during vascular remodeling tissues, such as in growing tumors. Expression of egfl7 is endothelial cell-specific in physiological conditions, however it is aberrantly expressed by tumor cells in human cancers. In colorectal cancer, high levels of egfl7 correspond to tumors with higher pathologic stages and to the presence of lymph node metastases. Egfl7 is also over-expressed by tumor cells in human hepatocellular carcinoma and overexpression is significantly higher in tumors with multiple nodules, without capsules and with vein invasion. Levels of egfl7 are thus correlated with markers of metastasis and with poor prognosis. Suppression of egfl7 expression inhibits the migration of hepatocellular carcinoma cells through an EGFR/FAK pathway. In vivo, egfl7 knockdown expression in hepatocellular carcinoma cells has been reported to decrease the number of intra-hepatic and pulmonary metastases. In mice, inhibition of egfl7 in hepatocellular carcinoma cells decrease tumor growth and micro-vessel density. Over-expression of Egfl7 in tumor cells implanted in mice has been reported to increase tumor growth and metastasis. Within the tumors, Egfl7 increases micro-vessel density, hypoxia, necrosis and vascular permeability. Egfl7 promotes tumor escape from immunity by repressing leukocyte adhesion molecules of tumor blood vessel endothelial cells. Consequently, tumors over-expressing Egfl7 are much less infiltrated by immune cells. A specific example of an EGFL7 (epidermal growth factor domain-like 7) inhibitor is parsatuzumab (MEGF0444A, RG7414) monoclonal antibody.

26. Chemotherapy Using Notch Pathway Inhibitors

Endothelial cells use the Notch signaling pathway to coordinate cellular behaviors during the blood vessel sprouting that occurs in angiogenesis. Activation of Notch takes place primarily in "connector" cells and cells that line patent stable blood vessels through direct interaction with the Notch ligand, Delta-like ligand 4 (Dll4), which is expressed in the endothelial tip cells. VEGF signaling, which is an important factor for migration and proliferation of endothelial cells, can be down-regulated in cells with activated Notch signaling by lowering the levels of Vegf receptor transcript. A specific example of a Notch pathway inhibitors is PF-03084014 (Gamma secretase inhibitor of proteolytic activation of Notch receptors). An orally bioavailable, small-molecule gamma secretase (GS) inhibitor with potential antitumor activity is RO4929097 which blocks activation of Notch receptors.

27. Chemotherapy Using Src-Family Kinase Inhibitors

Proto-oncogene tyrosine-protein kinase Src also known as proto-oncogene c-Src or simply c-Src is a non-receptor protein tyrosine kinase protein that in humans is encoded by the SRC gene. This protein phosphorylates specific tyrosine residues in other proteins. An elevated level of activity of c-Src tyrosine kinase is suggested to be linked to cancer progression by promoting other signals. c-Src can be activated by many transmembrane proteins that include: adhesion receptors, receptor tyrosine kinases, G-protein coupled receptors and cytokine receptors. Most studies have looked at the receptor tyrosine kinases and examples of these are platelet derived growth factor receptor (PDGFR) pathway and epidermal growth factor receptor (EGFR). When src is activated, it promotes survival, angiogenesis, proliferation and invasion pathways. The activity of c-Src has been best characterized in colon cancer. Researchers have shown that Src expression is 5 to 8 fold higher in premalignant polyps than normal mucosa.[15][16][17] The elevated c-Src levels have also been shown to have a correlation with advances stages of the tumor, size of tumor, and metastatic potential of tumors. Specific examples of Src-family kinase inhibitors include bosutinib (SKI-606), bafetinib, AZD-530, XL1-999, KX01, dasatinib, and XL228.

28. Chemotherapy Using DNA Methyltransferase Inhibitors

Cancer is driven by epigenetic alterations. Epigenetic alterations refer to functionally relevant modifications to the genome that do not involve a change in the nucleotide sequence. Examples of such modifications are changes in DNA methylation (hypermethylation and hypomethylation). DNA methyltransferase (DNMT) enzymes catalyze the transfer of a methyl group to DNA. DNA methylation serves a wide variety of biological functions. All the known DNA methyltransferases use S-adenosyl methionine (SAM) as the methyl donor. These enzymes are responsible for the methylation of specific DNA sequences in order to prevent the host from digesting its own genome via its restriction enzymes. Excess methylated cytosine in tumor suppressor genes is a consistent hallmark of human cancers. Changes in the pattern of DNA methylation, either increased (hypermethylation) or decreased (hypomethylation), have been identified in all types of cancer cells examined so far. Specific examples of DNA methyltransferase inhibitors include Dacogen® (EU) (decitabine, 2'-Deoxy-5-azacytidine, 5-Aza-2'-deoxycytidine, NSC 127716), 5-azacytidine, zebularine, (−)-epigallocatechin-3-gallate, procaine, psammaplins, and MG98.

It has been reported that resistance of human tumor xenografts to treatment with cisplatin, carboplatin, temozolomide, and epirubicin was decreased by adding nontoxic doses of decitabine. Importantly, the timing of drug administration appears to be associated with therapeutic response. To be effective, decitabine had to be given 6-12 days before the cytotoxic drug; if decitabine was given at the same time or after the cytotoxic drug was administered, sensitization was lost. This observation provides strong support for the notion that decitabine sensitizes tumors by epigenetic reactivation of proapoptotic genes that potentiate the effects of cytotoxic drugs.

29. Chemotherapy Using DNA Intercalators

Molecules (also known as ligands) can interact with DNA. Ligands may interact with DNA by covalently binding, electrostatically binding, or intercalating. Intercalation occurs when ligands of an appropriate size and chemical nature fit themselves in between base pairs of DNA. DNA intercalators are used in chemotherapeutic treatment to inhibit DNA replication in rapidly growing cancer cells.

These ligands are mostly polycyclic, aromatic, and planar. Specific examples of DNA intercalators include berberine, ethidium bromide, proflavine, daunomycin, doxorubicin (Adriamycin, Doxil), and thalidomide.

30. Chemotherapy Using Thymidine Synthase Suicide Inhibitors

Thymidylate synthase inhibitors are chemicals which inhibit the enzyme thymidylate synthase and have potential as an anticancer chemotherapy. This inhibition is termed suicide inhibition, and is irreversible. The enzyme binds a substrate analogue and forms an irreversible complex with it through a covalent bond during the "normal" catalysis reaction. Specific examples of suicide inhibitor drugs which inhibit thymidine synthase include 5-fluorouracil (5-FU, Efudex), raltitrexed, pemetrexed, nolatrexed, ZD9331, and GS7904L. Raltitrexed, and fluorouracil have been used for treating colorectal cancer.

31. Chemotherapy Using Mitotic Inhibitor (Microtubule Function Disruptor)

A mitotic inhibitor blocks cell division by disrupting microtubules which structurally pull a cell apart when it divides. Mitotic inhibitors are used in cancer treatment, because cancer cells are able to grow and eventually spread through the body (metastasize) through continuous mitotic division and are more sensitive to inhibition of mitosis than normal cells. Specific examples of drugs mitotic disruptors include Taxol (paclitaxel), Taxotere (docetaxil), Abraxane, Halaven, Jevtana, vinblastine, vincristine, and vinorelbine.

32. Chemotherapy Using DNA Cross-Linkers

Crosslinks in DNA occur when various exogenous or endogenous agents react with two different positions in the DNA. This can either occur in the same strand (intrastrand crosslink) or in the opposite strands of the DNA (interstrand crosslink). Crosslinks also occur between DNA and protein. DNA replication is blocked by crosslinks, which causes replication arrest and cell death if the crosslink is not repaired. Alkylating agents such as 1, 3-bis(2-chloroethyl)-1-nitrosourea (BCNU, carmustine)) and nitrogen mustard which are used in chemotherapy can cross link with DNA at N7 position of guanine on the opposite strands forming interstrand crosslink. Cisplatin (cis-diamminedichloro-platinum(II)) and its derivative forms DNA cross links as monoadduct, interstrand crosslink, intrastrand crosslink or DNA protein crosslink (mainly on the adjacent N-7 guanine forming 1, 2 intrastrand crosslink). Mitomycin C is a potent DNA crosslinker by sequence specific guanine base N-alkylation. Specific examples of DNA crosslinkers also include Paraplatin, and Eloxatin.

33. Chemotherapy Using DNA Strand Breakers

Cancer therapy procedures such as chemotherapy and radiotherapy work by overwhelming the capacity of the cell to repair DNA damage, resulting in cell death. Cells that are most rapidly dividing, i.e., cancer cells, are preferentially affected. The DNA repair process is constantly active as it responds to damage in the DNA structure. When normal repair processes fail, and when cellular apoptosis does not occur, irreparable DNA damage may occur, including double-strand breaks and DNA crosslinkages (interstrand crosslinks or ICLs). If a cell retains DNA damage, transcription of a gene can be prevented, and, thus, translation into a protein will also be blocked. Replication may also be blocked and the cell may die. A specific example of a drug which induces DNA strand breaks is bleomycin.

34. Chemotherapy Using DNA Alkylators

Alkylation of DNA is used in chemotherapy to damage the DNA of cancer cells. Alkylated DNA either does not coil or uncoil properly, or cannot be processed by information-decoding enzymes. This results in cytotoxicity with the effects of inhibition of the growth of the cell, initiation of programmed cell death or apoptosis. However, mutations are also triggered, including carcinogenic mutations, explaining the higher incidence of cancer after exposure. A specific example of a DNA alklylating drug is mephalen (Alteran).

35. Chemotherapy Using JNK-dependent p53 Ser15 Phosphorylation Inducers

Many enzymes and receptors are switched "on" or "off" by phosphorylation and dephosphorylation. The p53 tumor suppressor protein is heavily regulated and contains more than 18 different phosphorylation sites. Through JNK-dependent p53 Ser15 phosphorylation, activation of p53 can lead to cell cycle arrestor apoptotic cell death. A specific example of this is the drug plumbagin which has been shown to induce cell cycle arrest and apoptosis in numerous cancer cell lines.

36. Chemotherapy Using DNA Topoisomerase Inhibitors

Irinotecan prevents DNA from unwinding by inhibition of topoisomerase 1. Irinotececan (campostar, CPT-111) is used to treat colon cancer, in particular, in combination with other chemotherapy agents. This includes the regimen FOLFIRI, which consists of infusional 5-fluorouracil, leucovorin, and irinotecan.

37. Chemotherapy Using Bcl-2 Inhibitors

Bcl-2 encoded by the BCL2 gene, is the founding member of the Bcl-2 family of regulator proteins that regulate cell death (apoptosis). Damage to the Bcl-2 gene is a cause of a number of cancers and a cause of resistance to cancer treatments. Over-expression of anti-apoptotic genes, and under-expression of pro-apoptotic genes, can result in the lack of cell death that is characteristic of cancer. Specific examples of BCl inhibitors include RG7601 (ABT-199, GDC-0199), obatoclax (GX15-070), ABT-737, RG7601 (ABT-199; ABT199; ABT 199; and GDC-0199).

38. Chemotherapy Using Free Radical Generators.

A number of cancer chemotherapeutic agents increase free radical levels. Examples include sorafenib and Adriamycin.

39. Chemotherapeutic Prodrugs

In one embodiment, any chemotherapeutic agent or prodrug agent that increases the activity or effectiveness of a chemotherapeutic agent is useful in the methods provided herein.

In one embodiment, the method of practicing the invention involves administering to a patient with a prodrug chemotherapeutic agent selected from the group consisting of a hypoxia activated prodrug, evofosfamide, TH-302, AQN4, banoxatrone, a nitrogen mustard prodrug, PR-104, apaziquone, EO-9, CB1954, 5-(aziridin-1-yl)-4-hydroxylamino-2-nitrobenzamide, canofosfamide, TLK286, TER286, JS-K, and Boc-KAc-Puro.

In one embodiment, the method of practicing the invention involves administering to a patient with a peptidomimetic inhibitor of GSH or GHT-π, for example, a peptidomimetic inhibitor selected from the group consisting of γ-glutamyl-S-(benzyl)cysteinyl-R-phenylglycine diethyl ether, TLK199, Telintra, and NOV-002. The peptidomimetic inhibitor of GSH or GHT-π lowers cancer cell levels of GSH (glutathione) or the activity of GHT-π (glutathione-S-transferase-π) and this can potentiate the toxicity of an administered anticancer drug by preventing its metabolism. Also the treatment of a cancer patient with TLK-199 which is also an inhibitor of the multidrug resistant-associated protein known to be a multidrug efflux transporter, can be used to increase cancer cell levels of a chemotherapeutic agent.

In one embodiment, the cancer chemotherapeutic agent is a prodrug that is activated by GSH. In one embodiment, the method of practicing the invention involves administering to a patient a GSH-activated prodrug selected from the group consisting of cis-6-(2-acetylvinylthio)purine (cis-AVTP), and trans-6-(2-acetylvinylthio)guanine (trans-AVTP). This method of practicing the invention can involve treatment of a cancer patient with a GST-activated prodrug, the GST-activated prodrug selected from the group consisting of γ-glutamyl-α-amino-β(2-ethyl-N,N,N',N'-tetrakis (2-chloroethyl)phosphodiamidate)-sulfonyl)-propionyl-(R)-phenylglycine (TLK286) and $O^2$-[2,4-dinitro-5-(N-methyl-N-4-carboxyphenylamino) phenyl] 1-N,N-dimethylamino) diazen-1-ium-1,2-diolate (PABA/NO).

V. Methods of Treatment

While not to be bound by any specific mechanism, it is believed that CONPs are particularly useful in connection with anti-cancer treatment because CONPs cause marginal harm to a patient's normal non-cancerous cells. During radiation therapy, CONPs have been found to protect irradiated normal cells from radiation and improve efficacy of combined radiation/chemotherapy.

In a first aspect, the invention comprises a method of treating a cancer in a patient in need therefor, comprising:
administering an effective dose of cerium oxide nanoparticles to the patient;
administering a therapeutically effective dose of radiation to the patient; and
administering a dose of a chemotherapeutic agent to the patient, thereby treating the cancer.

In one embodiment, CONPs are administered before radiation. Without being bound by any theory, it is believed the CONPs sensitize cancer cells to radiation therapy and prevent damage to normal cells.

In one embodiment, CONPs are administered after radiation therapy. Without being bound by any theory, it is believed that the CONPs treat acute damage and/or chronic damage from radiation treatment. This approach is advantageous over the current clinical standard where a toxic protectant is administered 30 minutes before radiation therapy but does not protect against chronic damage occurring 6 months, 12 months after radiation treatment.

In one embodiment, the administration of the cerium oxide nanoparticles improves the efficacy of treatment of combination radiation/chemotherapy treatment.

In one embodiment, the administration of the cerium oxide nanoparticles lowers the therapeutically effective radiation dose and/or lowers the therapeutically effective chemotherapeutic agent dose compared to the therapeutically effective dose in the absence of nanoparticles.

In one embodiment, the administration of the cerium oxide nanoparticles lowers the therapeutically effective radiation dose and lowers the therapeutically effective chemotherapeutic agent dose compared to the effective dose in the absence of nanoparticles.

In one embodiment, the administration of the cerium oxide nanoparticles lowers the therapeutically effective radiation dose and lowers the therapeutically effective chemotherapeutic agent dose compared to the effective dose in the absence of nanoparticles and/or radiation.

In one embodiment, the administration of the cerium oxide nanoparticles lowers the therapeutically effective radiation dose and lowers the therapeutically effective chemotherapeutic agent dose compared to the effective dose in the absence of nanoparticles and/or chemotherapy.

In one embodiment, the dose of radiation or chemotherapy is from between about 1% and 90%, or between about 1% and 80%, or between about 1% and 70%, or between about 1% and 60%, or between about 1% and 50%, or between about 1% and 40%, or between about 1% and 30%, or between about 1% and 20%, or between about 1% and 10% of either (i) the dose used in the current treatment standard in the absence of CONPs or the (i) therapeutically effective dose in the absence of CONPs.

In one embodiment, the dose of radiation or chemotherapy is between about 10% and 90%, or between about 20% and 80%, or between about 30% and 70%, between about 40% and 60%, between about 10% and 50%, between about 10% and 30%, between about 50% and 90%, or between about 70% and 90%.

In one embodiment, the radiation may be administered after the cerium oxide nanoparticles are administered.

In another embodiment, the radiation may be administered before the cerium oxide nanoparticles are administered.

In one embodiment, the chemotherapeutic agent is administered before the nanoparticles and/or radiation.

In another embodiment, the chemotherapeutic agent is administered at the same time as the nanoparticles and/or radiation.

In another embodiment, the chemotherapeutic agent is administered after the nanoparticles and/or radiation.

In another embodiment, the method further comprises a surgical resection of the cancer (i.e., a tumor) before radiation is administered.

In another embodiment, the method further comprises a surgical resection of the cancer (i.e., tumor) after the radiation is administered.

In another embodiment, the method further comprises a surgical resection of the cancer (i.e., tumor) before the chemotherapeutic agent is administered.

In another embodiment, the method further comprises surgical resection of the cancer (i.e., tumor) after the chemotherapeutic agent is administered.

In exemplary embodiments, a patient is successfully "treated" according to the methods of the present disclosure if the patient shows one or more of the following: (i) a reduction in the number of or complete absence of cancer cells; (ii) a reduction in the tumor size or volume; (iii) retardation or reversal of tumor growth, (iv) inhibition, e.g., suppression, prevention, retardation, shrinkage, delay, or reversal of metastases, e.g., of cancer cell infiltration into peripheral organs including, for example, the spread of cancer into soft tissue and bone; (v) inhibition of, e.g., suppression of, retardation of, prevention of, shrinkage of, reversal of, delay of, or an absence of tumor metastases; (vi) inhibition of, e.g., suppression of, retardation of, prevention of, shrinkage of, reversal of, delay of, or an absence of tumor growth; (viii) relief of one or more symptoms associated with the specific cancer; (ix) reduced morbidity and mortality; and/or (x) improvement in quality of life. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable.

Another aspect provides a method of treating a cancer in a patient, comprising:
administering an effective dose of cerium oxide nanoparticles to the patient;
administering a therapeutically effective dose of radiation to the patient;

administering a therapeutically effective dose of a first chemotherapeutic agent to the patient; and administering a therapeutically effective dose of a second cancer chemotherapeutic agent to the patient.

In another embodiment, the administration of the effective dose of the cerium oxide nanoparticles lowers the therapeutically effective dose of radiation and/or lowers the therapeutically effective dose of the chemotherapeutic agent(s) as compared to the effective dose in the absence of nanoparticles.

In another aspect, the invention provides a method of reducing toxicity of radiation and/or at least one chemotherapeutic agent administered to a patient undergoing cancer treatment, comprising:

(i) administering an effective dose of CONPs to the patient, (ii) administering a dose of radiation and/or at least one chemotherapeutic agent, wherein administering an effective dose of CONPs reduces the toxicity of radiation and/or at least one chemotherapeutic agent administered to the patient.

In another aspect, the invention provides a method of decreasing a dose of radiation and/or at least one chemotherapeutic agent administered to a patient required to effectively treat a cancer, comprising (i) administering an effective amount of CONPs to the patient, (ii) administering a dose of radiation and/or at least one chemotherapeutic agent, wherein administering an effective dose of CONPs reduces the dose of radiation and/or at least one chemotherapeutic agent required to effectively treat cancer.

In one embodiment, the method permits a reduced dose of radiation or chemotherapy than the current standard of care in the absence of CONPs or the effective amount to treat the tumor. In various embodiments, the dose of radiation or chemotherapy is between about 1% and 90%, or between about 1% and 80%, or between about 1% and 70%, or between about 1% and 60%, or between about 1% and 50%, or between about 1% and 40%, or between about 1% and 30%, or between about 1% and 20%, or between about 1% and 10% of either (i) the dose used in the current treatment standard in the absence of CONPs or (ii) the effective amount to treat the tumor in the absence of CONPs.

In other embodiments, the dose of radiation or chemotherapy is between about 10% and 90%, or between about 20% and 80%, or between about 30% and 70%, or between about 40% and 60%, or between about 10% and 50%, or between about 10% and 30%, or between about 50% and 90%, or between about 70% and 90%.

In one embodiment, a lower dose of the second cancer chemotherapeutic agent than standard of care is administered to treat a cancer in a cancer patient due to the anti-cancer effectiveness of the treatment of the patient's cancer using administered CONPs.

In one embodiment, the chemotherapeutic agent is administered before the nanoparticles and/or radiation.

In another embodiment, the chemotherapeutic agent is administered at the same time as the nanoparticles and/or radiation.

In another embodiment, the chemotherapeutic agent is administered after the nanoparticles and/or radiation.

In another embodiment, the CONPs may be administered to a patient in a dose between about 1 nanogram per kilogram patient body weight to about 5 milligrams per kilogram patient body weight; or between about 1 nanogram per kilogram patient body weight to about 5 milligrams per kilogram patient body weight; or between about 1 nanogram per kilogram patient body weight to about 5 milligrams per kilogram patient body weight; or between about 10 nanogram per kilogram patient body weight to about 0.5 milligrams per kilogram patient body weight; or between about 20 nanogram per kilogram patient body weight to about 100 micrograms per kilogram patient body weight; or between about 10 nanogram per kilogram patient body weight to about 10 micrograms per kilogram patient body weight.

The route of the administration of the CONPs or another chemotherapeutic agent or other substance may be any route known, including oral, intravenous, topical, subcutaneous, intramuscular, intraperitoneal, intra-urethral, into the bladder, by any catheter or cannula means to reach a cellular area or tissue area in a patient. Other routes of administration include injection, intrathecal, into cerebrospinal fluid, intrabronchial, intranasal, intravitrous humor, into a tumor, into the lymphatic system, into a lymph node, into an artery feeding a tumor, into a nerve sheath, intracardiac, pulmonary, rectal, intrauterine, vaginal, by an inhaler, by a transdermal patch, or by a pump using any of the aforementioned routes of administration.

In exemplary embodiments, the CONPs are provided as a pharmaceutical composition comprising cerium oxide nanoparticles and a pharmaceutically acceptable carrier, vehicle or diluents.

In exemplary embodiments, the CONP composition may be formulated as appropriate to any route of delivery, including, but not limited to oral, intravenous, topical, subcutaneous, intramuscular, intraperitoneal, intra-urethral, into the bladder, by any catheter or cannula means to reach a cellular area or tissue area in a patient. The most effective mode of administration and dosage regimen depends upon the location, extent, or type of the cancer being treated, the subject's health and response to treatment and the judgment of the treating physician.

In one embodiment, the CONP composition is a topical composition. Formulations suitable for topical administration include liquid or semi-liquid preparations suitable for penetration through the skin to the site of where treatment is required, such as liniments, lotions, creams, ointments or pastes, emulsions and drops suitable for administration to the eye, ear, or nose.

When formulated as a topical composition, the CONPs may be administered by an application to a skin area of the patient. The formulations are preferably administered at or adjacent to the area to be treated.

In one embodiment, the preferred route of administration of the CONPs for protection of normal skin and tissues of breast cancer patients treated with radiation is topical administration of CONPs.

In a particular embodiment, the topical composition comprises CONPs, a surfactant, an oil and water.

The term "surfactant" refers to a substance which aids the formation of an emulsion, and includes emulsifiers, detergents and other surface active agents. Surfactants suitable for use include any type of surfactant that has been used for pharmaceutical formulations, including, without limitation, anionic surfactants, non-ionic surfactants, cationic surfactants, and amphoteric surfactants. Examples of anionic surfactants include, but are not limited to, ammonium lauryl sulfate, sodium lauryl sulfate, ammonium laureth sulfate, sodium laureth sulfate, alkyl glyceryl ether sulfonate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, potassium lauryl sulfate, potassium laureth sulfate, sodium lauryl sarcosinate, sodium lauroyl sarcosinate, lauryl sarcosinate, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium and ammonium salts of coconut alkyl triethylene glycol ether sulfate; tallow alkyl triethylene glycol ether sulfate, tallow alkyl hexaoxyethylene sulfate, disodium N-octadecylsulfosuccinnate, disodium lauryl sulfosuccinate, diammonium lauryl sulfosuccinate, tetrasodium N-(1,2-dicarboxyethyl)-N-octadecylsulfosuccinnate, diamyl ester of sodium sulfosuccinic acid, dihexyl ester of sodium sulfosuccinic acid, dioctyl esters of sodium sulfosuccinic acid, docusate sodium, and combinations thereof.

Examples of nonionic surfactants include, but are not limited to, polyoxyethylene fatty acid esters, sorbitan esters, cetyl octanoate, cocamide DEA, cocamide MEA, cocamido propyl dimethyl amine oxide, coconut fatty acid diethanol amide, coconut fatty acid monoethanol amide, diglyceryl diisostearate, diglyceryl monoisostearate, diglyceryl monolaurate, diglyceryl monooleate, ethylene glycol distearate, ethylene glycol monostearate, ethoxylated castor oil, glyceryl monoisostearate, glyceryl monolaurate, glyceryl monomyristate, glyceryl monooleate, glyceryl monostearate, glyceryl tricaprylate/caprate, glyceryl triisostearate, glyceryl trioleate, glycol distearate, glycol monostearate, isooctyl stearate, lauramide DEA, lauric acid diethanol amide, lauric acid monoethanol amide, lauric/myristic acid diethanol amide, lauryl dimethyl amine oxide, lauryl/myristyl amide DEA, lauryl/myristyl dimethyl amine oxide, methyl gluceth, methyl glucose sesquistearate, oleamide DEA, PEG-distearate, polyoxyethylene butyl ether, polyoxyethylene cetyl ether, polyoxyethylene lauryl amine, polyoxyethylene lauryl ester, polyoxyethylene lauryl ether, polyoxyethylene nonylphenyl ether, polyoxyethylene octyl ether, polyoxyethylene octylphenyl ether, polyoxyethylene oleyl amine, polyoxyethylene oleyl cetyl ether, polyoxyethylene oleyl ester, polyoxyethylene oleyl ether, polyoxyethylene stearyl amine, polyoxyethylene stearyl ester, polyoxyethylene stearyl ether, polyoxyethylene tallow amine, polyoxyethylene tridecyl ether, propylene glycol monostearate, sorbitan monolaurate, sorbitan monooleate, sorbitan monopalmitate, sorbitan monostearate, sorbitan sesquioleate, sorbitan trioleate, stearamide DEA, stearic acid diethanol amide, stearic acid monoethanol amide, laureth-4, and combinations thereof.

Examples of amphoteric surfactants include, but are not limited to, sodium N-dodecyl-alanine, sodium N-lauryl-iminodipropionate, myristoamphoacetate, lauryl betaine, lauryl sulfobetaine, sodium 3-dodecyl-aminopropionate, sodium 3-dodecylaminopropane sultanate, sodium lauroamphoacetate, cocodimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, oleamidopropyl betaine, coca dimethyl sulfopropyl betaine, stearyl dimethyl sulfopropyl betaine, lauryl dimethyl sulfoethyl betaine, lauryl bis-(2-hydroxyethyl) sulfopropyl betaine, and combinations thereof.

Examples of cationic surfactants include, but are not limited to, behenyl trimethyl ammonium chloride, bis(acyloxyethyl) hydroxyethyl methyl ammonium methosulfate, cetrimonium bromide, cetrimonium chloride, cetyl trimethyl ammonium chloride, cocamido propylamine oxide, distearyl dimethyl ammonium chloride, ditallowdimonium chloride, guar hydroxypropyltrimonium chloride, lauralkonium chloride, lauryl dimethylamine oxide, lauryl dimethylbenzyl ammonium chloride, lauryl polyoxyethylene dimethylamine oxide, lauryl trimethyl ammonium chloride, laurtrimonium chloride, methyl-1-oleyl amide ethyl-2-oleyl imidazolinium methyl sulfate, picolin benzyl ammonium chloride, polyquaternium, stearalkonium chloride, sterayl dimethylbenzyl ammonium chloride, stearyl trimethyl ammonium chloride, trimethylglycine, and combinations thereof.

Suitable oils are physiologically acceptable and include, but are not limited to: simple lipids, derived lipids, complex lipids that are derived from natural vegetable oil and fat, animal oil and fat, and mineral oil, or a mixture of those.

Other suitable excipients may be included including, for example, antioxidants, UV absorbers, radical scavengers, chelating agents, vitamins and derivatives thereof, abrasives, astringents, fragrance, structuring agents, emulsifiers, solubilizing agents, buffering agents, thickeners, pH adjusters, pigments or colorants, and preservatives. Preservatives can be used to prevent the growth of fungi and other microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetypyridinium chloride, chlorobutanol, phenol, phenylethyl alcohol, thimerosal, and combinations thereof. In exemplary embodiments, the topical composition is packaged in single-use doses.

In one embodiment, the preferred route of administration of the CONPs is by intravenous administration.

In one embodiment, the preferred route of administration of the CONPs for protection of normal tissues of pancreatic cancer patients treated with radiation is intravenous administration of CONPs.

In a particular embodiment, the CONPs are formulated as a micro-emulsion. In exemplary embodiments, the microemulsion is an oil-in-water micro-emulsion. In exemplary embodiments, the microemulsion is water-in-oil microemulsion.

While the amount of CONPs to be contained in the composition is not particularly limited, for example, the CONPs are contained in the composition from about 0.0001 to about 10% by weight of the entire formulation, or about 0.001 to 1% by weight, or about 0.01 to 0.5% by weight.

During cancer treatment or following administration, the total concentration of cerium oxide nanoparticles in the blood plasma of the patient may be between about 5 nanomolar to about 200 micromolar, or between about 10 nanomolar to about 100 micromolar, or between about 20 nanomolar to about 10 micromolar.

In one embodiment, the patient who is treated by the present invention is diagnosed with a pancreatic cancer, a lung cancer, a breast cancer, a colon cancer, a liver cancer, a skin cancer, a brain cancer, a bone cancer, a kidney cancer, an ovarian cancer, a uterine cancer, a prostate cancer, or a head cancer and a neck cancer.

In exemplary embodiments, the cancer treated by the method of the present invention is a solid tumor. Representative, non-limiting of solid tumors suitable include nervous system tumors, retinoblastoma, neuroblastoma, pediatric tumors, kidney cancers, renal cell adenocarcinoma, oesophagogastric cancer, hepatocellular carcinoma, pancreaticobiliary neoplasia, adenocarcinomas, islet cell tumours, colorectal cancer, cervical cancer, anal cancer, uterine cancer, reproductive tract cancer, urinary tract cancer, ureter cancer, bladder cancer, germ cell tumour, testicular germ cell tumour, ovarian germ cell tumour, ovarian cancer, ovarian epithelial cancer, carcinoma of unknown primary, human immunodeficiency associated malignancy, Kaposi's sarcoma, lymphoma, leukemia, malignant melanoma, sarcoma, endocrine tumour, thyroid gland tumour, mesothelioma, or other pleural tumour, peritoneal tumour, neuroendocrine tumour or carcinoid tumour.

The total concentration of cerium oxide nanoparticles (CONPs) in the blood plasma of the patient is defined as the plasma protein bound CONPs plus the free blood plasma concentrations of the CONPs.

1. Treatment Schedules

Radiation therapy is administered using conventional methods and devices to at appropriate doses, fractionated appropriately to provide the appropriate dose of radiation to the area in need of treatment.

Patients usually receive external-beam radiation therapy in daily treatment sessions over the course of several weeks. The number of treatment sessions depends on many factors, including the total radiation dose that will be given.

For external radiation to the lymph node areas and areas such as the breast, patients may receive treatment once a day, 5 days a week, for 3 to 7 weeks. Internal radiation for example in treating breast cancer, is usually given twice a day for 1 week. External partial-breast radiation, when used, is given twice a day for 1 week. For treatment to areas where the cancer has spread, daily treatments for 2 to 3 weeks are typical.

Chemotherapeutic agents may be administered by any conventional administration route, for example by those routes described herein. The skilled practitioner is aware of the methods to determine dose and schedule of chemotherapy administration.

Depending on the drug(s) to be given, there are different ways to determine chemo doses. The overall dose may be based on a patient's body weight in kilograms while some chemo doses are determined based on body surface area (BSA), which doctors calculate using height and weight.

Chemotherapy is commonly given at regular intervals or cycles. A cycle may involve a dose of one or more drugs followed by several days or weeks without treatment to permit normal cells time to recover from drug side effects. Doses may be given a certain number of days in a row, or every other day for several days, followed by a period of rest. Some drugs work best when given continuously over a set number of days.

Chemotherapy treatments once a week, once every 10 days or once every two or three weeks.

In various embodiments, the course of chemotherapy is for X number of cycles of chemotherapy, with each cycle given about every Y number of days.

Where X is selected from 1, 2, 3, 4, 5, 6, 7, 8, 9, 10, or more than 10 cycles and Y is selected from 1, 2, 3, 4, 5, 6, 7, 8, 9, 10, 14, or 21 days.

By way of example, not intended to be limiting, a proposed schedule for chemotherapy and radiation is provided as follows:

Example Schedule:

Chemotherapeutic Agent #1—given by IV on Monday of Week 1, Week 5

Chemotherapeutic Agent #2—given by oral on Tuesday-Friday of Week 1, Week 3

Radiation Therapy—given Monday-Friday of Week 1, Week 2, Week 3, Week 4, Week 5, Week 6.

EXAMPLES

Example 1

Use of Cerium Oxide Nanoparticles in Combination with Radiation Therapy to Treat Pancreatic Cancer Cells In some embodiments of the present invention, CONPs are non-agglomerated 3 to 5 nanometer sized crystals which can be prepared by a micro-emulsion process known in the art.

Figure 2:
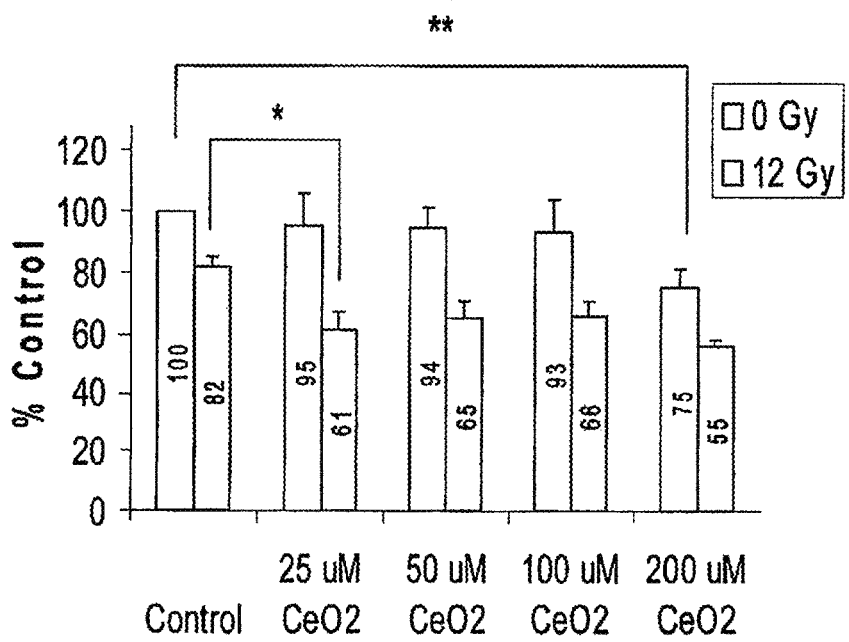

FIGS. 1 and 2 illustrate the results of the presence of cerium oxide nanoparticles on L3.6pl human pancreatic cancer cells treated to radiation. The white bars represent cells that were not radiated, while the grey bars represent cells irradiated at 12 Gy. An MTT assay (a colorimetric cell viability assay) was performed 24 h (FIG. 1) and 48 h (FIG. 2) after the radiation exposure to determine the radioprotection and/or cytotoxicity of the CONPs. CONPs at a concentration of 25 to 200 µM increased the radiation-induced death of the pancreatic cancer cells in cell culture. The cytotoxicity of 200 µM CONPs was more significant 48 h (FIG. 2) after the radiation exposure than at 24 h (FIG. 1).

Figure 3:
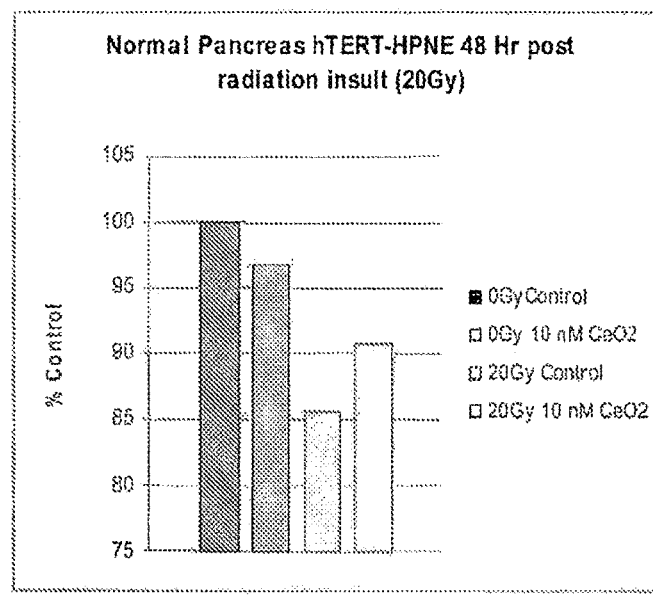
FIGS. 3 and 4 are graphs of normal hTERT HPNE (FIG. 3) and pancreatic L3.6pl cell lines 48 h post radiation insult (note that h-TERT HPNE refers to human telomerase reverse transcriptase immortalized cell line of human pancreatic duct cells).
Figure 4:
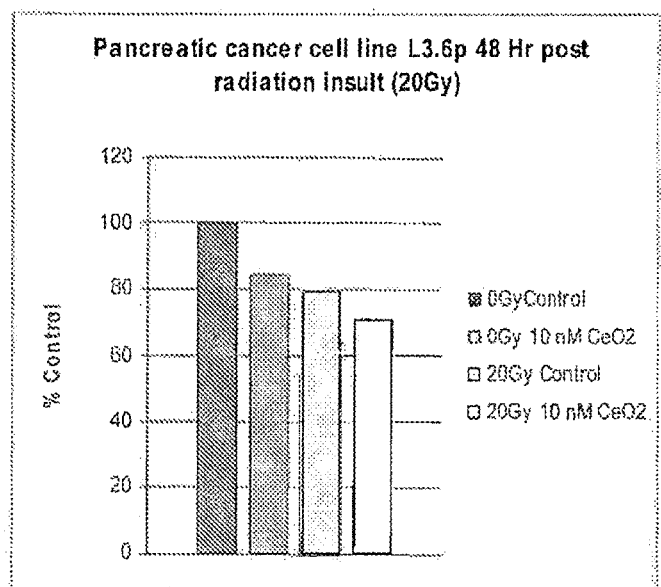

A study of radiation-induced cell death in normal pancreatic cells (hTERT HPNE cell line) (FIG. 3) and in the pancreatic cancer cell line L3.6PL (FIG. 4) was performed by plating cells in white-walled 96-well plates (20,000/well) overnight. After 24 h, some cells were treated with the saline vehicle, and some, with a nanoparticle solution containing 10 nM CONPs and returned to incubation at 5% $CO_2$, 37° C., for 24 h. After incubation, some of the plates were irradiated with a single dose of 20 Gy, and the plates were returned to the incubator. After 48 h, cell proliferation was assessed with the use of an ATP luminescence assay. Increased cell death is observed in the 20 Gy control for the normal cells, with radioprotection indicated in the presence of CONPs.

Figure 5:
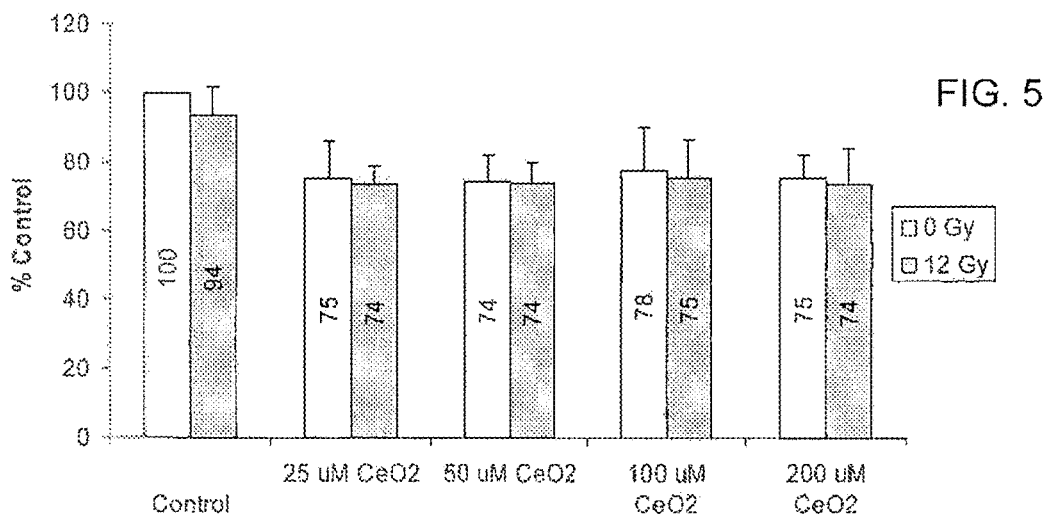
FIGS. 5 and 6 are graphs of the results of 24 h (FIG. 5) and 48 h (FIG. 6) MTT assay to determine the effect of cerium oxide on Panc-1 human pancreatic cancer cells.
Figure 6:
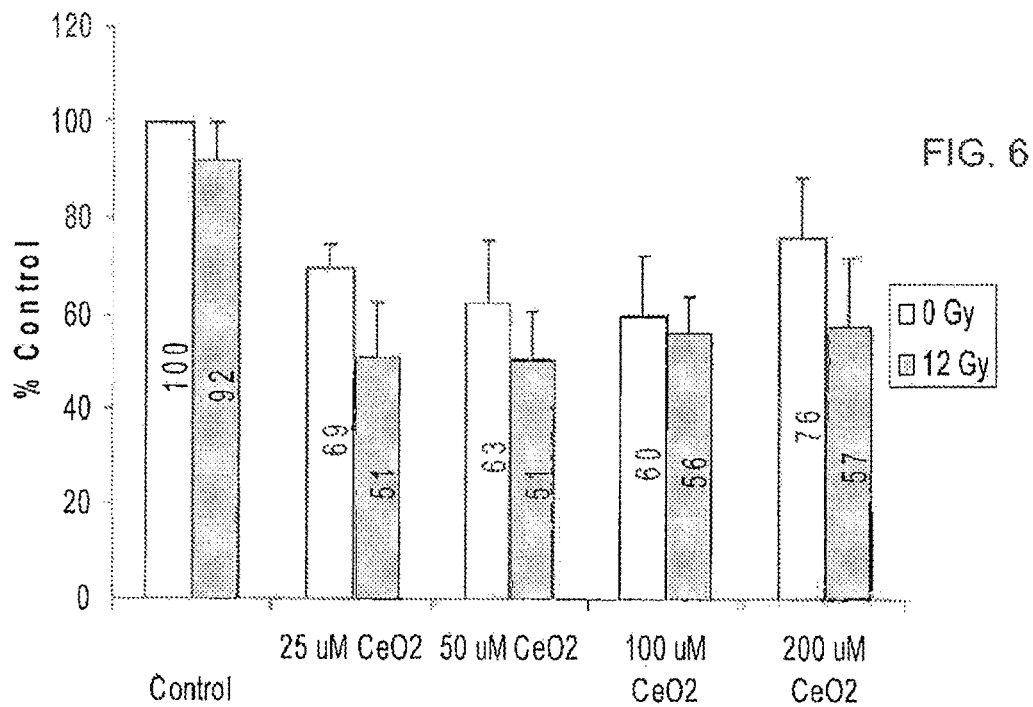

FIGS. 5 and 6 illustrate the radio-protective and/or cytotoxicity effects of CONPs on Panc-1 human pancreatic cancer cells. The assays performed were MTT assays at 24 h (FIG. 5) and 48 h (FIG. 6). It was found that CONPs at all concentrations were cytotoxic to Panc-1 cells, in both the presence and the absence of radiation. There was no significant enhancement of radiation-induced death at 24 h, but there was enhanced radiation-induced death at 48 h. Therefore, CONPs on human pancreatic cancer cells did not protect against radiation-induced death.

Figure 7:
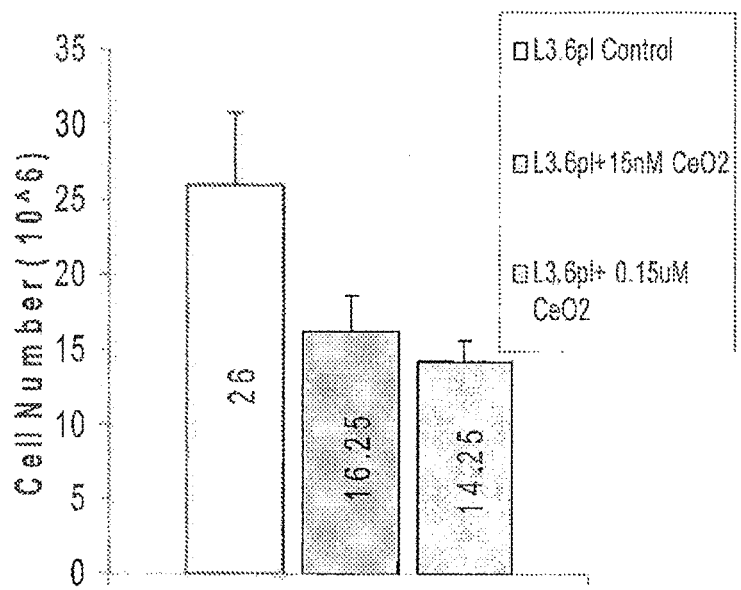
FIG. 7 is a graph of the results of a 48 h cell count study on L3.6pl human pancreatic cancer cells.

FIG. 7 is a graph illustrating the results of a 48 h cell count study on L3.6pl human pancreatic cancer cells, in order to determine the cytotoxicity of $CeO_2$. It was found that there was no significant difference in induction of cytotoxicity between 15 nM and 150 nM. The same results were obtained with an MCF-7 human breast cancer cell line.

Figure 8:
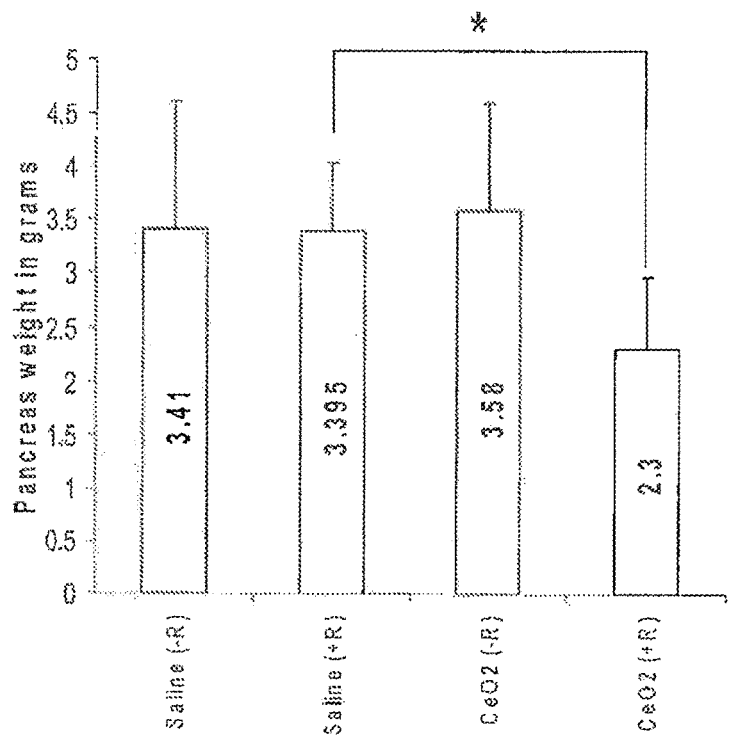
FIGS. 8 and 9 are graphs of the results of 6-week tumor weight (FIG. 8) and tumor volume (FIG. 9) studies on irradiated nude mice having human pancreatic cancer cells growing therein.

Another experiment studied the effects of CONPs on irradiated nude mice having had human pancreatic cancer cells injected therein. Mice were injected twice weekly intravenously with 100 ul of 15 nM (0.00001 mg/kg) $CeO_2$, and irradiated once a week with a fractionated dose of 5 Gy for 6 weeks. FIG. 8 is a graph of the results of this experiment, showing that radiation alone does not reduce pancreatic tumor weight after the 6 weeks of radiation treatment (total of 35 Gy). In the presence of radiation, CONP-treated mice had a 37% decrease in tumor weight, as compared with radiation-treated mice.

Figure 9:
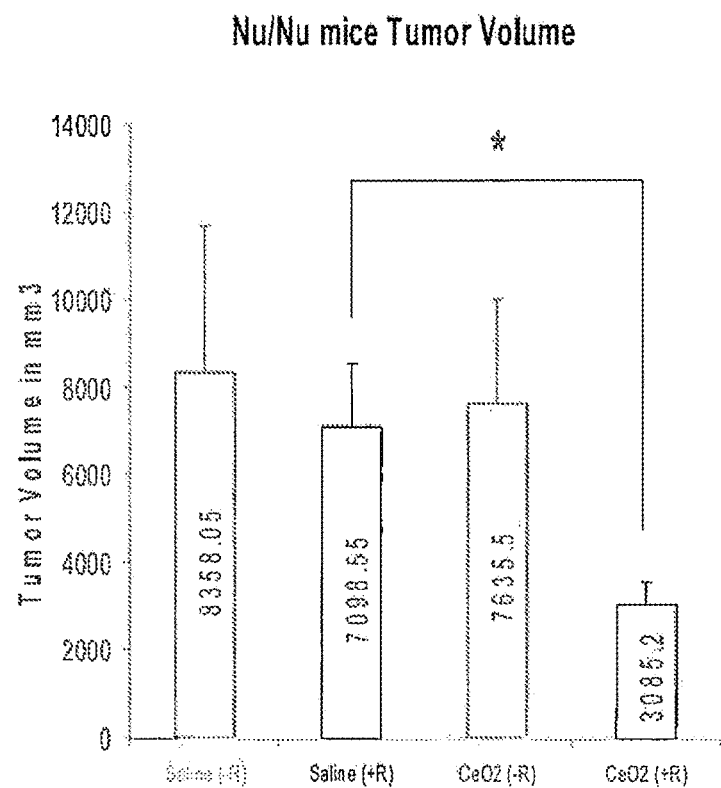

In a similar experiment (FIG. 9), the effects of CONPs on irradiated nude mice having had human pancreatic cancer cells injected therein were studied with regard to tumor volume. Again, mice were injected twice weekly intravenously with 100 ul of 15 nM (0.00001 mg/kg) CONPs, and irradiated once a week with a fractionated dose of 5 Gy for 6 weeks. It was found that radiation alone reduced pancreatic tumor volume after the 6 weeks of radiation treatment (total of 35 Gy), and that CONPs as a single agent reduced pancreatic tumor volume. In the presence of radiation, CONPs-treated mice had a 50% decrease in tumor volume as compared with radiation-treated mice.

Table 2 contains data on the remits of treatment of orthotopically-implanted L3.6 pl pancreatic cancer cells by ionized radiation and cerium oxide nanoparticles (CONPs).

TABLE 2

Treatment of Orthotopically Implanted L3.6p1 Human Pancreatic Cancer Cells by Ionized Radiation (R) and Cerium Oxide Nanoparticles (CONPs)

| Treatment Group[1] | Tumor Incidence[2] | Tumor Volume (mm$^3$) Median | Tumor Volume (mm$^3$) Range | Tumor Weight (g) Median | Tumor Weight (g) Range | Incidence of Liver Metastasis | Body Weight (g) Media | Body Weight (g) Range |
|---|---|---|---|---|---|---|---|---|
| Saline Control | 10/10 | 7661 | 3436 to 11311 | 3.53 | 3.41-5.88 | 1/10 | 32 | 29-34 |
| Saline (+R) | 10/10 | 6251 | 5645 to 8844 | 3.40 | 2.44-3.90 | 2/10 | 29 | 27-33 |
| CONPs (−R) | 10/10 | 6251 | 4486 to 9175 | 3.58 | 2.67-4.70 | 1/10 | 30 | 26-34 |
| CONPs (+R) | 10/10 | 3.044[3] | 3002 to 4206 | 2.3[4] | 1.30-2.78 | 1/10 | 27 | 24-32 |

L3.6pl human pancreatic cancer cells (1×10⁰) were injected into the pancreas of nude mice. Ten days later, groups of mice were treated with vehicle solution, 5 Gy ionized radiation once weekly (30 Gy), twice weekly i.p. 15 nM CONPs, and a combination of 5 Gy ionized radiation once weekly (30 Gy), twice weekly i.p. 15 nM cerium oxide NP. All mice were killed on day 45.

Number of positive mice/number of mice injected.
P<0.005 compared to control.
P<0.01 compared to control.

Figure 10A:
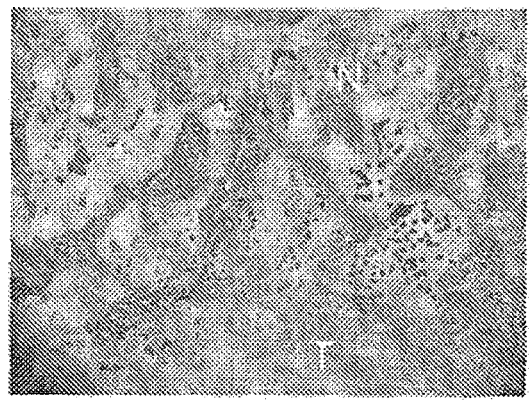
FIGS. 10A and 10B are histological slides of pancreatic tumor tissue with radiation alone (FIG. 10A) and radiation plus CONPs (FIG. 10B).
Figure 10B:
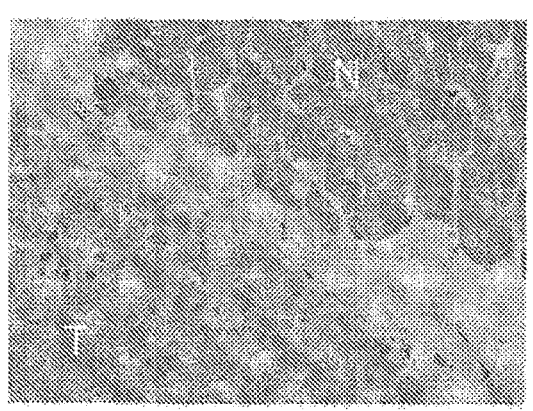
Figure 11:
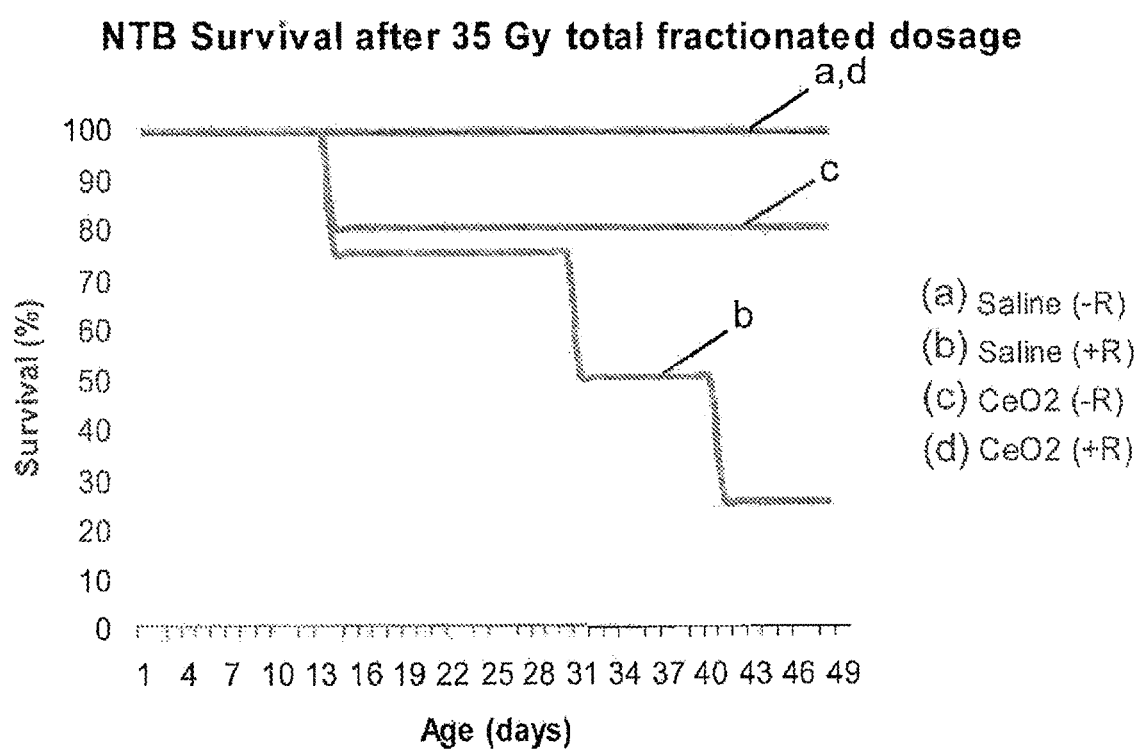
FIG. 11 is a graph of the effect of CONP injections on the survival rate of non-tumor-bearing nude mice.
Figure 12:
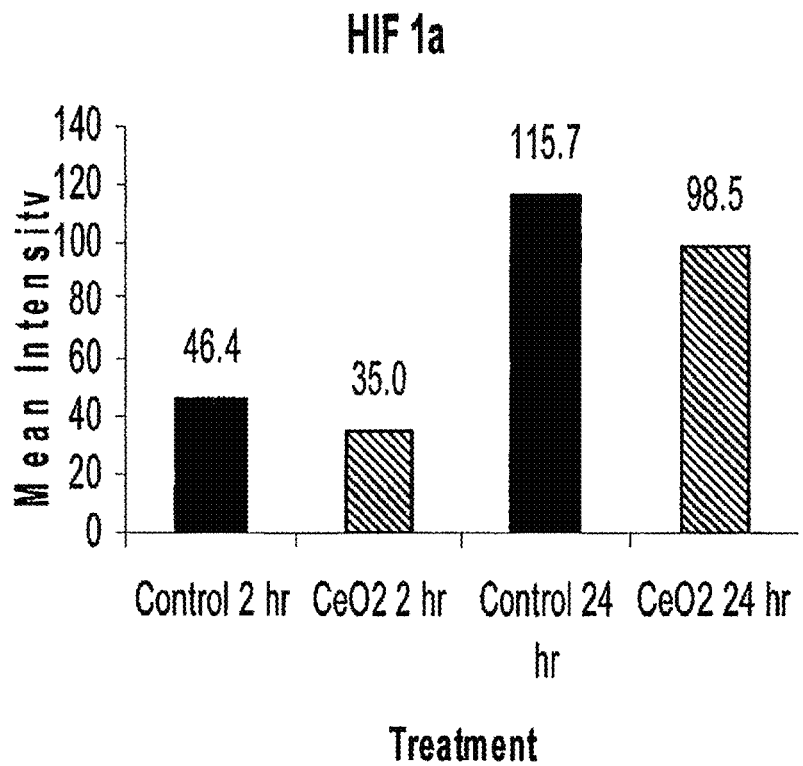
FIGS. 12 and 13 are graphs of the effect of hypoxia on L3.6pl pancreatic cancer cells using HIF 1a (FIG. 12) and HIF 2a (FIG. 13) as indicator, wherein FIG. 13 also includes a photograph of a gel from a Western blot assay of protein levels.
Figure 13:
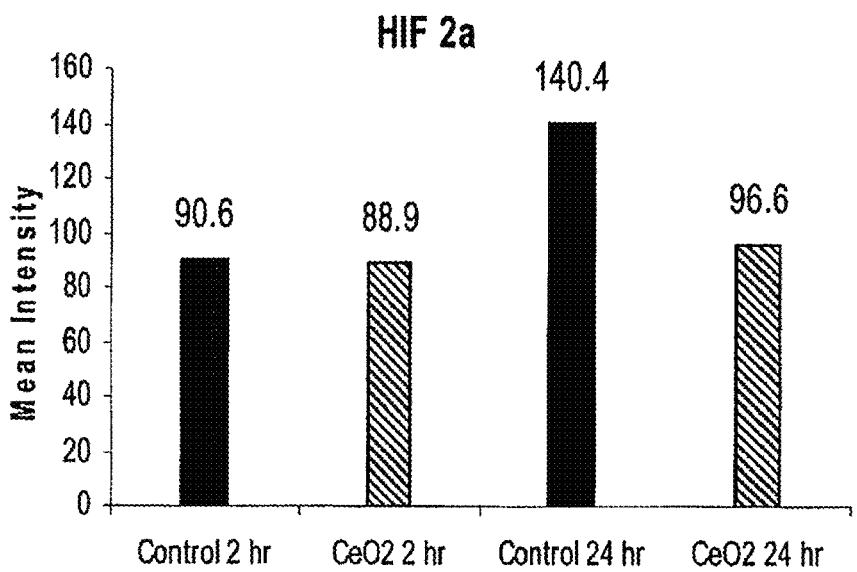

FIGS. 10A and 10B are reproductions of histological slides of pancreatic tumor tissue with radiation alone (FIG. 10A) and radiation plus CONPs (FIG. 10B). Here it is shown that CONPs sensitize tumor cells to radiation treatment and at the same time protect normal tissue. FIG. 10A shows an irradiated pancreatic tumor surrounded by non-functional pancreatic tissue. FIG. 10B shows an irradiated tumor surrounded by functional normal pancreatic tissue. FIG. 11 is a graph of the effect of cerium oxide injections on the survival rate of non-tumor-bearing nude mice. As above, mice were injected twice weekly intravenously with 100 ul of 15 nM (0.00001 mg/kg) CONPs and irradiated once a week with a fractionated dose of 5 Gy for 7 weeks. Here it is shown that CONPs are well tolerated by the mice, and that no deleterious effects were observed in the CONPs-treated group. Mice that received radiation alone (curve b) were found to succumb to radiation-induced death, but all the CONP-treated mice (curves c and d) survived the radiation treatment. Hypoxia experiments were also undertaken, since it is known that CONPs act as an oxygen buffer in low oxygen conditions. Tumors are hypoxic by nature; so the hypoxic microenvironment in the tumor makes the tumor resistant to radiation treatment, since oxygen is necessary for the production of superoxide radicals. For this study, L3.6pl pancreatic cancer cells were exposed to a hypoxic environment for 5 h, and mRNA was extracted 2 and 24 h after induction of hypoxia. RT-PCT results for HIF 1a (FIG. 12) and HIF 2a (FIG. 13) demonstrated that cells treated with $CeO_2$ (CONPs) retained their baseline mRNA levels 24 h after hypoxia exposure. Beneath FIG. 13 are shown the results of a Western blot assay to prove that the same amount of protein was loaded onto the gel, and that, therefore, the changes in HIF that were measured reflect the effects of cerium oxide nanoparticles (CONPs) and not loading. It is hypothesized that CONPs can oxygenate the tumor microenvironment, increasing tumor radiation sensitivity. HIF 1a and HIF 2a are overexpressed in cells under hypoxic conditions, and are transcription factors important in vascular development. Hypoxia is also known to contribute greatly to the pathophysiology of major categories of human disease, including myocardial and cerebral ischemia, cancer, pulmonary hypertension, congenital heart disease, and chronic obstructive pulmonary disease.

Figure 14:
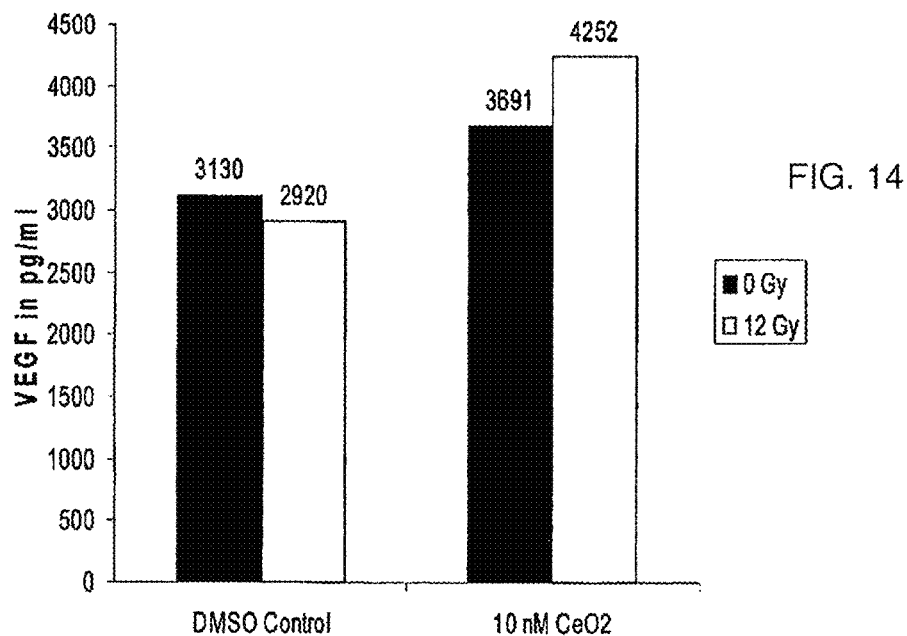
FIGS. 14 and 15 are graphs of the effects of cerium oxide on VEGF production by L3.6pl human pancreatic cancer cells 24 h (FIG. 14) and 48 h (FIG. 15) after irradiation.
Figure 15:
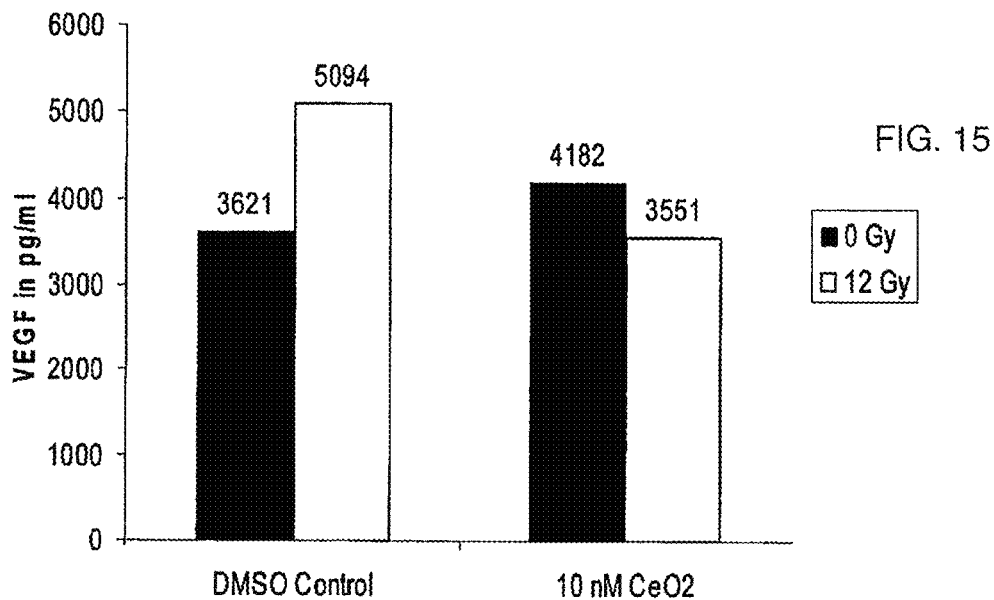

FIGS. 14 and 15 are graphs of the effects of cerium oxide on VEGF production by L3.6pl human pancreatic cancer cells 24 h (FIG. 14) and 48 h (FIG. 15) after irradiation. In this study, VEGF concentration was determined from the cell culture supernatant, and it was found that CONPs slightly increased VEGF concentration on both non-irradiated (control) and irradiated cells. It was also found that 12 Gy irradiation increased VEGF production in the vehicle control, and that CONPs abrogated the VEGF production after radiation insult.

Example 2

Figure 16:
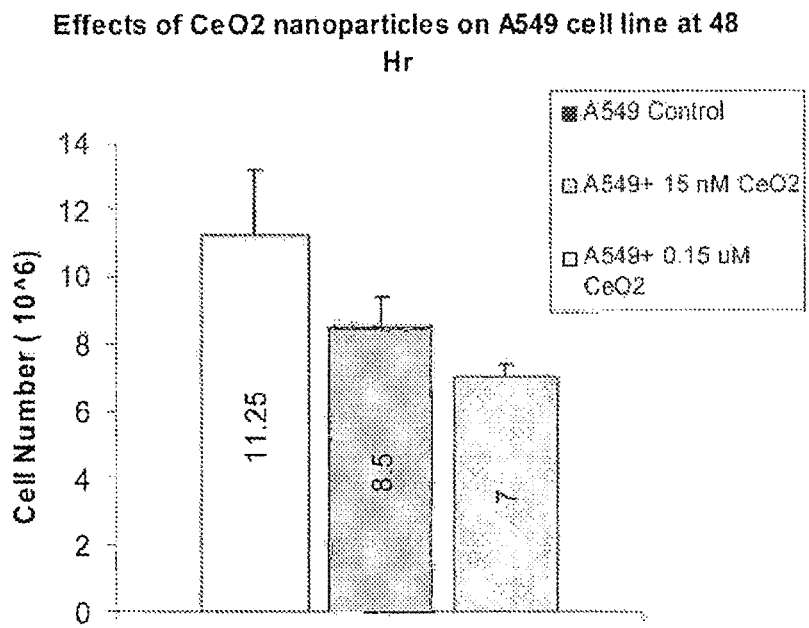
FIGS. 16 and 17 are graphs of the results of a 48 h cell count study on un-irradiated (FIG. 16) and irradiated (FIG. 17) A549 human lung cancer cells.
Figure 17:
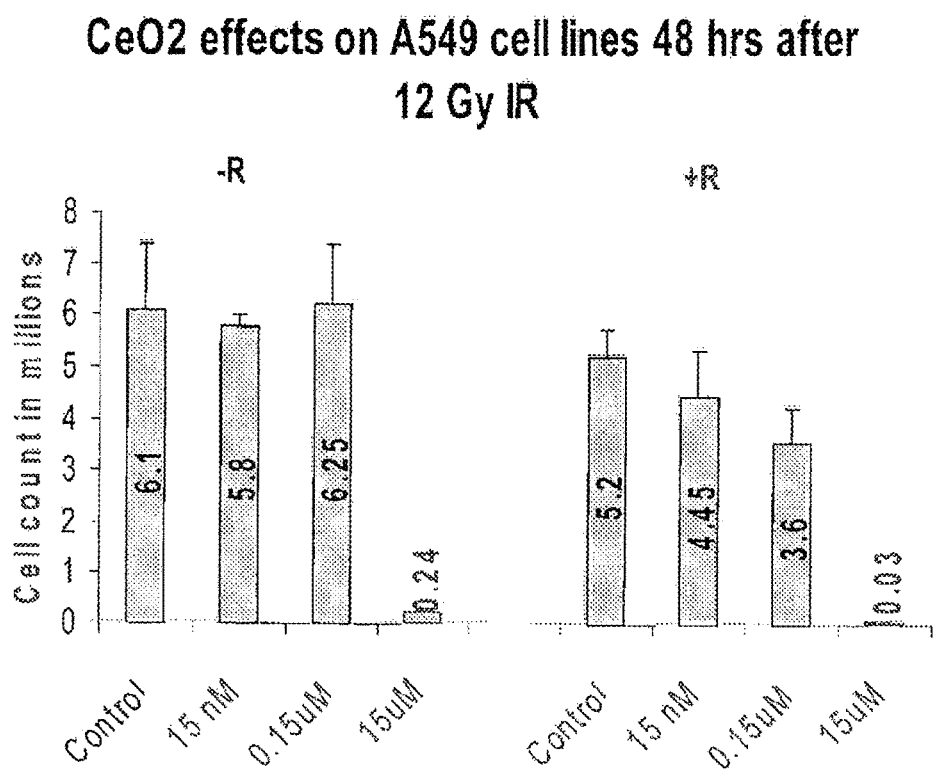
Figure 18:
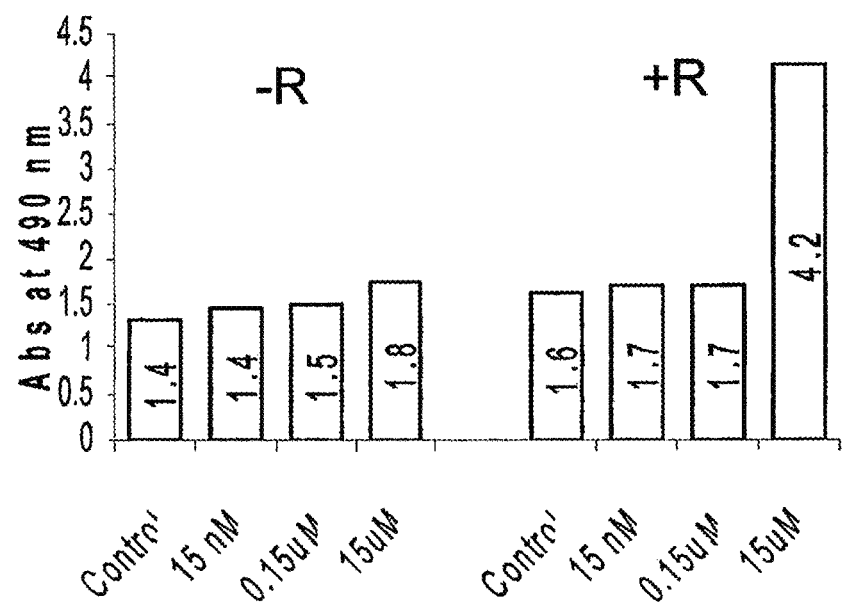
FIG. 18 is a graph of the results of a 48 h LOH study on irradiated A549 human lung cancer cells.

Use of Cerium Oxide Nanoparticles in Combination with Radiation Therapy to Treat Lung Cancer Cells The effects of CONPs on A549 human lung cancer cells are illustrated in FIG. 16. A 48 h cell count assay was undertaken to determine cytotoxicity, with the result that, at high concentration, CONPs are cytotoxic to this cell line in dose-dependent fashion. FIG. 17 also illustrates results of a 48 h cell count study on irradiated A549 human lung cancer cells. Here it is shown that, for these cells, the effect of CONPs is most significant at 15 uM, and that CONPs increase radiation-induced death in a dose-dependent manner. In addition, FIG. 18 further illustrates results of the effects of CONPs on irradiated A549 human lung cancer cells. A 48 h study included the testing of cell culture supernatant for the presence of LOH, which monitors for cell death. Again, as in FIG. 18, 15 uM CONPs was found to be the most significant concentration in the presence of radiation.

Figure 19:
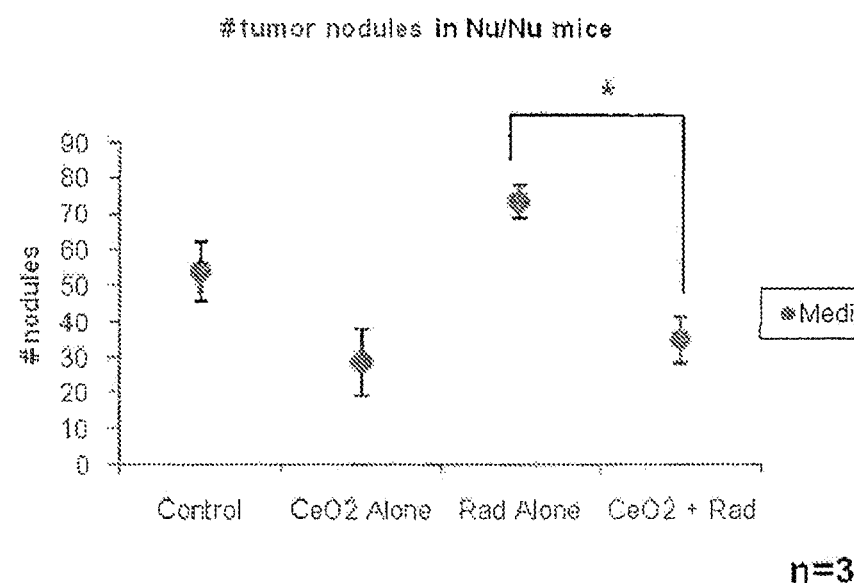
FIGS. 19 and 20 illustrate the results obtained on an orthotopic lung cancer model, wherein the number of tumor nodules in Nu/Nu mice (FIG. 19) and whole lung weight (FIG. 20) are plotted.
Figure 20:
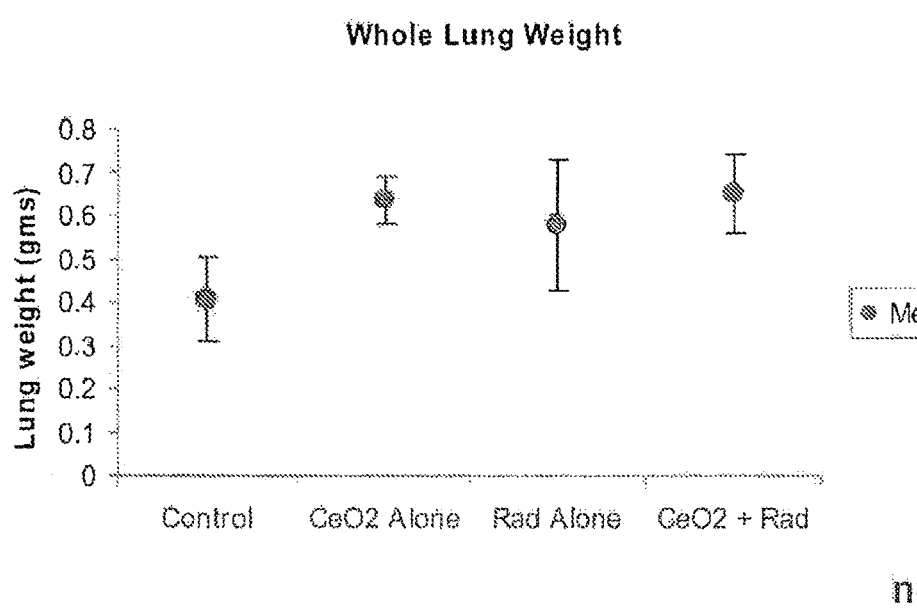

An orthotopic lung cancer model is illustrated in FIGS. 19 and 20, wherein the number of tumor nodules in Nu/Nu mice (FIG. 19) and whole lung weight (FIG. 20) are plotted for conditions with and without radiation, and with and without CONPs. It can be seen that the number of tumor nodules is significantly reduced in the presence of cerium oxide nanoparticles (CONPs).

Another deleterious effect of radiation treatment for lung cancer is pneumonitis, the inflammation of lung tissue. Both in vitro (using normal lung fibroblast CCL 135 cells) and in vivo (using athymic nude mice lung tissue) experiments were performed to test the efficacy of CONPs in radioprotection of lung tissue.

Figure 21A:
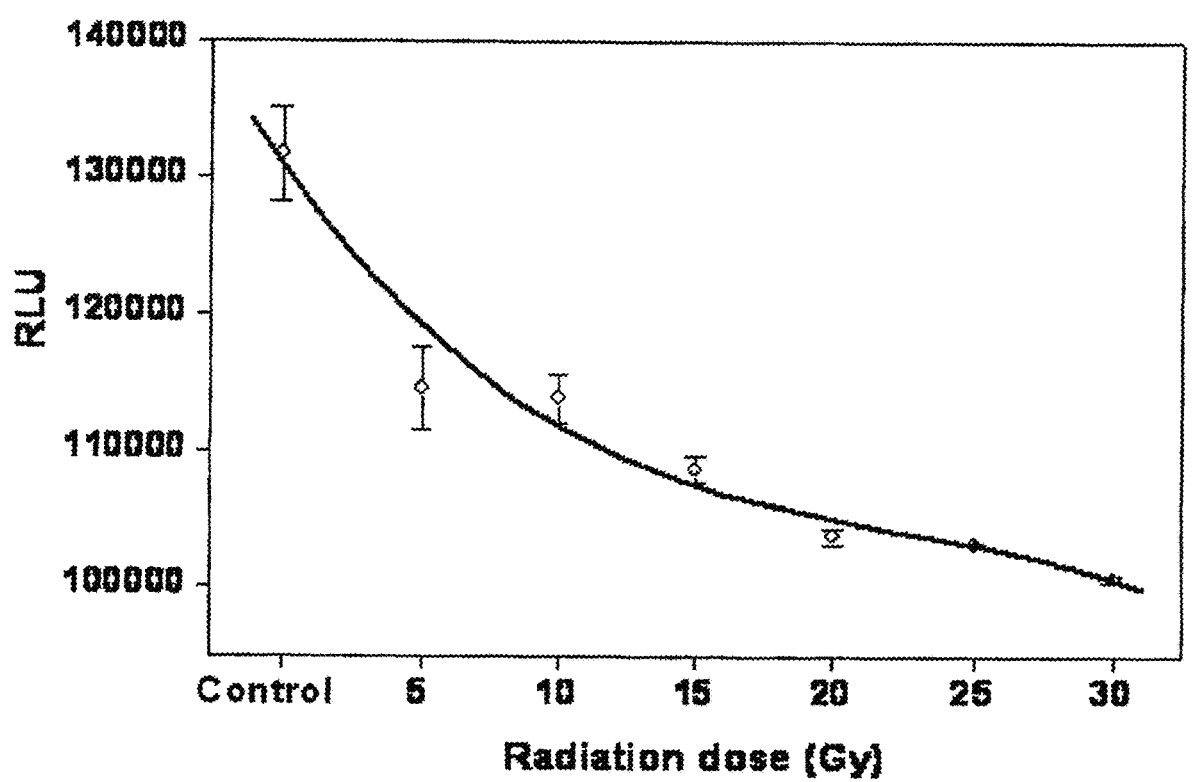
FIGS. 21A to 21C illustrate the radio-protective effect of cerium oxide nanoparticles on normal lung fibroblasts, including a plot of cell viability versus radiation dose (FIG. 21A), cell viability under 20 Gy radiation with and without the presence of cerium oxide nanoparticles (FIG. 21B), and cell apoptosis under 20 Gy radiation, with and without the presence of cerium oxide nanoparticles (FIG. 21C).

For in vitro studies, the cells were trypsinized with a brief exposure to 0.25% trypsin and 0.02% EOTA, and 20,000 cells were delivered to 96-well plates in Dulbecco's Minimal Essential Medium (OMEM), supplemented with 10% fetal bovine serum. In the first set of studies, the cells were exposed to 0, 5, 10, 15, 20, 25, 30 Gy of radiation for 48 h. Radiation was performed on the 160-kV cell culture and small animal irradiator (radiation machine) from Kimtron Inc. (Woodbury, Conn.). Cell viability was determined by measuring the amount of ATP present, which signals the presence of metabolically active cells (FIG. 21A). The ATP is measured using the CellTiter-Glo luminescent Cell Viability Assay (Promega, Madison, Wis.). A direct relationship exists between luminescence measured with the CellTiter-Glo Assay and the number of cells in culture; therefore, the amount of ATP is directly proportional to the number of cells present. The detection of luminescence (RLU) is measured by a luminometer.

In the next set of experiments cells were treated with a predetermined optimal concentration of 10 nM of CONPs and exposed to a single dose of radiation (20 Gy). Forty-eight hours later, cell viability (FIG. 21B) was determined by measuring the amount of ATP present, using the CellTiter-Glo Luminescent Cell Viability Assay (Promega, Madison, Wis.). In addition, the amount of caspase 3/7 activity (FIG. 21C) was measured by the Caspase-Glo 3/7 Assay (Promega, Madison, Wis.), and the amount of luminescence is proportional to the caspase 3/7 activity.

For the in vivo studies, athymic nude mice are housed in the specific pathogen-free (SPF) Cancer Research Institute animal facility which exceeds the national requirements for animal care, with two conventional mouse rooms, two nude mouse rooms, and one quarantine room. Radiation was administered using an IC160 X-ray cell culture and small animal irradiation system (Kimtron Inc., Woodbury, Conn., USA) located inside the animal facility. Nine weeks post radiation, the mice were sacrificed and the lungs were harvested and processed for hematoxylin and eosin (H&E) staining. For immunohistochemistry and hematoxylin and eosin-staining procedures, one part of the tumor tissue is formalin-fixed and paraffin-embedded and another part embedded in OCT compound (Miles, Inc., Elkhart, Ind.), rapidly frozen in liquid nitrogen, and stored at −200° C. for sectioning. Immunofluorescence microscopy is performed using a 20× objective on an epifluorescence microscope equipped with narrow bandpass excitation filters mounted in a filter wheel (Ludl Electronic Products, Hawthorne, N.Y.).

Figure 21B:
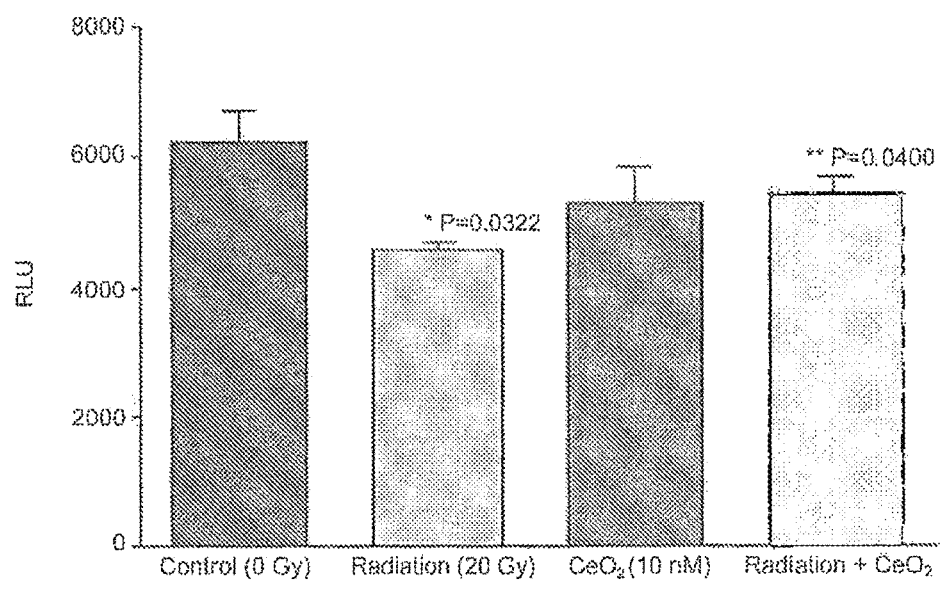
Figure 21C:
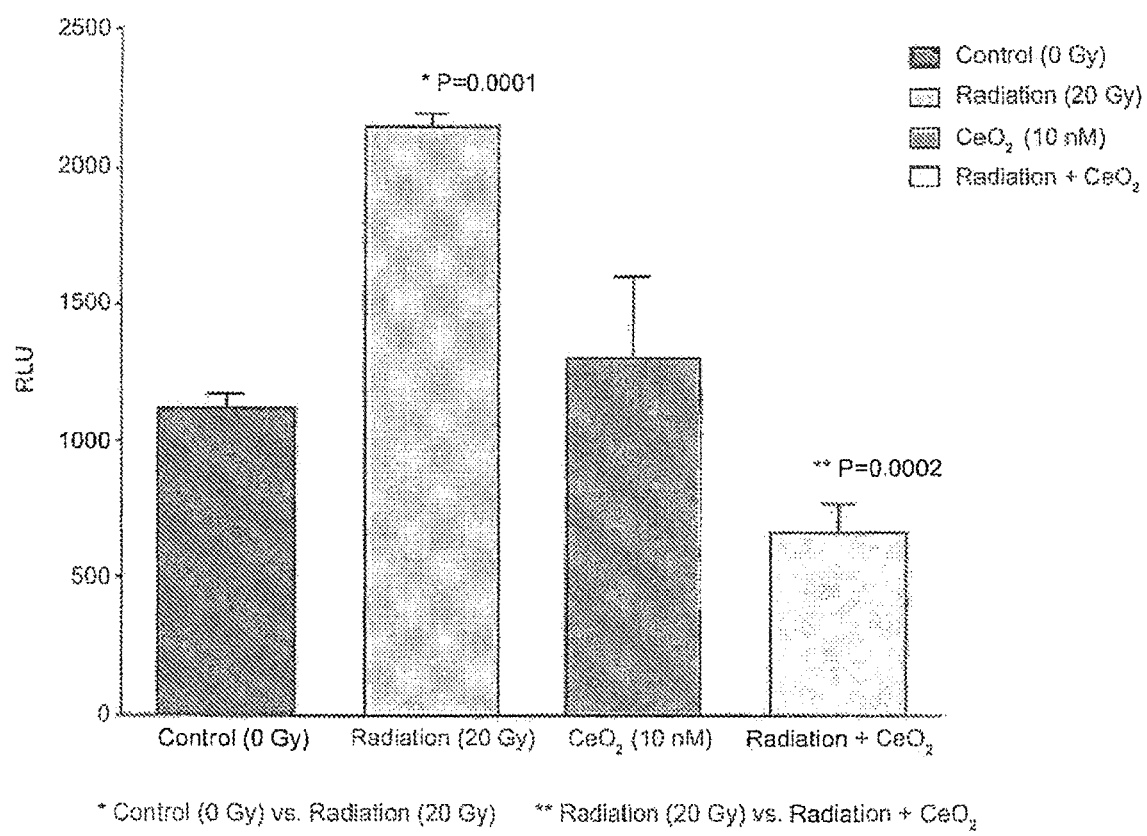

To obtain the results given in FIGS. 21A-21C, normal lung fibroblast (CCL 135) cells were exposed to increasing doses (5, 10, 15, 20, 25, 30 Gy) of radiation. The cell viability was measured by the quantification of ATP present, which signals the presence of metabolically active cells. As expected, results show a dose-dependent decrease in normal cell viability (FIG. 21A).

In the next set of experiments, the protective effect of CONPs on normal cells against radiation-induced cell damage was measured. Normal lung fibroblast CCL 135 cells were treated with a predetermined optimal concentration of 10 nM CONPs and exposed to a single dose of radiation (20 Gy). The results show that when radiation was administered as single therapy, the number of viable cells in culture, as measured by Cell Titer-Glo luminescent Cell Viability Assay (which signals the presence of metabolically active cells), was significantly decreased. However, when CONPs were administered 24 h prior to radiation, the CONPs significantly protected the normal lung fibroblast cells from radiation-induced cell death (FIG. 21B).

In subsequent experiments, normal lung fibroblast CCI 135 cells were treated with a 10 nM concentration of CONPs and exposed to a single dose of radiation (20 Gy).

Forty-eight hours later, Caspase 3/7 activity (which signals the presence of apoptosis) was measured (FIG. 21C). When radiation (20 Gy) was administered as single therapy, the levels of Caspase 3/7 activity significantly increased as compared to control cells (no radiation). However, in the presence of CONPs, the normal cells exposed to radiation were significantly protected and the activity of Caspase 3/7 was significantly decreased compared to control cells, and to cells exposed to CONPs alone, or radiation alone (FIG. 21C).

Radiation pneumonitis and subsequent pulmonary fibrosis can significantly decrease the quality of life of humans exposed to radiation. Therefore, in another set of experiments, a murine model of radiation-induced pneumonitis was established. A single dose of radiation (control, FIG. 22A; 12 Gy, FIG. 238; 15 Gy, FIG. 22C; and 18 Gy, FIG. 220) was administered to the thoracic ventral area of non-tumor bearing athymic nude mice. Nine weeks post radiation, the mice were sacrificed, and the lungs were harvested and processed for hematoxylin and eosin (H&E) staining. Results indicate that a successful murine model of radiation-induced pneumonitis has been developed, and histology analyses show established pneumonitis in the lungs of those mice receiving 15 and 18 Gy of radiation (FIGS. 22C and 22D).

In an attempt to administer nanoparticles to live animals and to evaluate the radiation protection activity of CONPs, the survival of non-tumor-bearing athymic nude mice was measured. Non-tumor-bearing athymic nude mice were exposed to fractionated doses of 30 Gy radiation (weekly administration of 5 Gy) in the presence or absence of twice weekly intravenous (i.v.) injections of Ce02 or intraperitoneal (i.p.) injections of Amifostine 30 min prior to radiation. Amifostine is a free radical scavenger. Nude mice (25 g) were randomized into the following groups: (1) weekly i.v. injections of saline (n=10, control group); (2) thrice weekly administrations of 5 Gy radiation (n=1O); (3) twice weekly i.v. injections of 15 nM (0.00001 mg/kg) CONPs (n=5); (4) thrice weekly i.p. injections of 150 mg/kg Amifostine (n=5); (5) administration of radiation combined with twice weekly i.v. injections of CONPs (n=10); and (6) administration of radiation combined with an Amifostine i.p. injection 30 min prior to radiation (n=10). Treatments continued for two weeks for a total dose of 30 Gy radiation. The mice were killed and necropsied only when they became moribund or the experiment was terminated. The weight and mortality of each mouse was measured throughout the experiment and median and percent survival was determined, as shown in FIG. 22E.

The results show that CONPs are well tolerated by athymic nude mice and protect mice from radiation-associated death. All control mice lived until termination date of 207 days. Interestingly, 80% of mice treated with CONPs alone were alive on termination date of 207 days. After treatment with radiation alone, Amifostine alone, and a combination of radiation and CONPs, or radiation and Amifostine, the median survival time was 132, 119, 210, and 81 days, respectively (control versus radiation, P<0.019; control versus Ce02, P<0.66; control versus Amifostine, P<0.0370; radiation versus radiation and CONPs, P<0.0041; radiation versus radiation and Amifostine, P<0.0432).

Amifostine was highly toxic to the mice, as shown by the significant difference in median survival time (as compared with control mice). In summary, these results suggest that CONPs nanoparticles are well tolerated by mice and have a significant advantage over Amifostine.

Figures 23E, 23F, 23G, 24H:
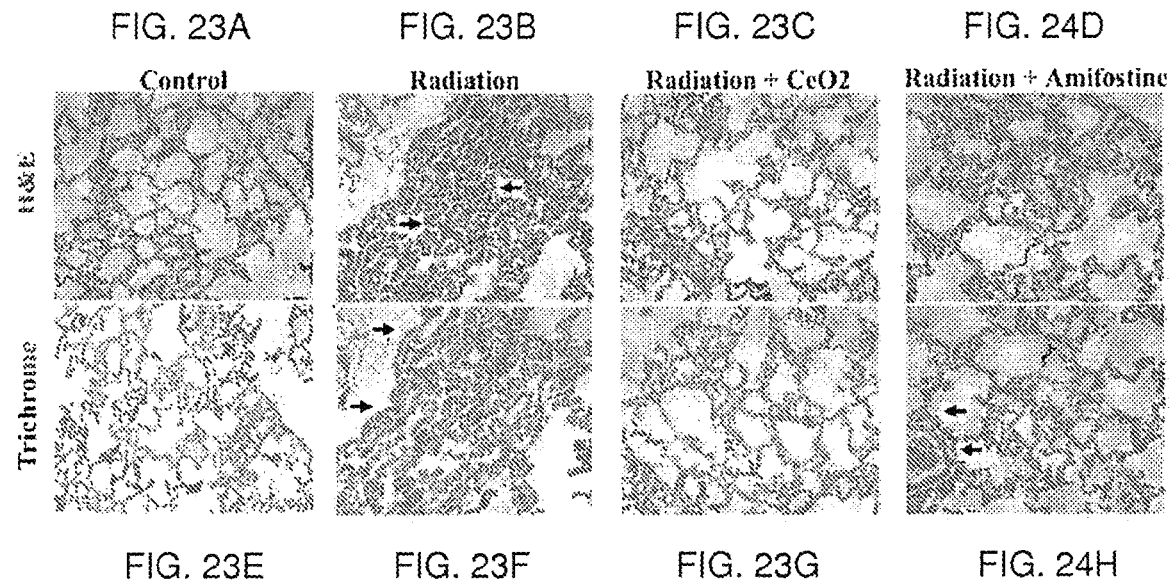

To determine the degree of radiation-induced pneumonitis, the lungs were harvested and processed for histology and H&E staining (FIGS. 23A-23D) and the amount of fibrosis and collagen deposition, indicative of chronic lung conditions, was measured using Masson's trichrome stain (FIGS. 23E-23H). The conditions include a control (FIGS. 23A, 23E), radiation alone (FIGS. 238, 23F), radiation plus CONPs (FIGS. 23C, 23G), and radiation plus Amifostine (FIGS. 230, 23H).

The lungs from mice in the control group (radiation alone, FIG. 238) showed visible pneumonitis, with extensive macrophage invasion, whereas the lungs from irradiated mice receiving CONPs showed no visible pneumonitis and appeared normal (FIG. 23C).

In the experiments using Masson's Trichrome stain, the immunohistochemical analyses show that fibrosis and collagen deposition were common in the irradiated lungs of those mice given radiation alone (FIG. 23F) and of those mice given a pretreatment of Amifostine (FIG. 23H). Furthermore, immunohistochemical analysis indicated that collagen deposits were relatively recent, due to the faint blue stain, as compared to dark blue staining of older, more cross-linked collagen seen in human chronic lung diseases. In sharp contrast, no significant Trichrome staining was observed in normal lungs (control, FIG. 23E) or in those irradiated lungs of mice treated with CONP (FIG. 23G).

Figure 24:
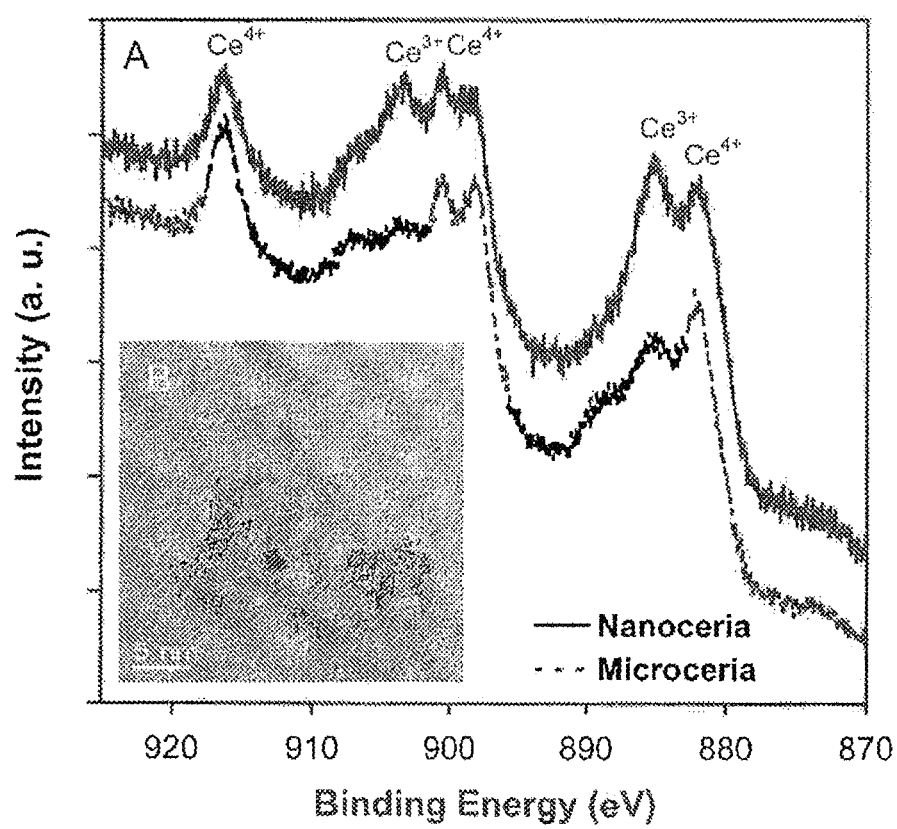
FIG. 24 plots x-ray photoelectron spectra for $Ce^{+3}$ and $Ce^{+4}$ in nanoceria (nanometer sized $CeO_2$ particles, CONPs) and microceria (micron-sized $CeO_2$ particles) with the inset a high-resolution transmission electron microscopy image of nanoceria particle.

The comparative Ce 3d x-ray photoelectron spectroscopy (XPS) spectra of micron size and synthesized cerium oxide nano particles (CONPs) are shown in FIG. 24. The XPS show a high concentration of $Ce^{+3}$ in CONPs compared with micron size cerium oxide particles. Peaks at 882.1 and 886 eV correspond to $Ce^{+4}$ and $Ce^{+3}$ peaks. Peaks at 918 eV correspond to satellite peaks indicating the presence of $Ce+^4$ peak.

The inset B of FIG. 24 is a high-resolution transmission electron microscopy (HRTEM) image of the synthesized CONPs (nanoceria, $CeO_2$ nanoparticles, cerium oxide nanoparticles) indicating the particle size of 3-5 nanometer size with a fluorite lattice structure.

CONPs have been shown to confer protection against radiation-induced cell damage in normal lung fibroblast (CCL 135) cells and suggest that CONPs are an effective radio-protectant for normal tissues. Furthermore, CONPs appear to be well tolerated by treated animals, and seem to protect athymic nude mice against radiation-associated death, leading to a novel approach to radiation protection.

It can be seen in the above results that CONPs are well tolerated by mice, and cause no toxicity to normal mice. CONPs also enhance radiation-induced cancer cell death, and protect normal tissue from radiation. Further, CONPs plus radiation control/minimize the metastatic index.

One embodiment of the present invention is a topical cream composition of CONPs. A plurality of compositions has been devised, each of which uses a "nanoactive solution," of CONPs. The topical CONP compositions are made as follows: A slurry is formed from a batch of 12% w/v ceria (CONPs) with 2% w/v Daxad, a sodium methacrylate acid-based surfactant. This slurry is stirred with the ingredients listed in Table 2 to form a smooth-spreading gel for spreading on the skin. In these compositions, Carbopol is a lightly cross-linked acrylic acid; Tween 80 is polysorbate 80, and the coconut oil is a fraction of whole oil in which the long-chain fatty acids are removed so that only the medium-chain saturated fatty acids remain. Centrifugation was performed for 15 min at 1380 G.

TABLE 3

Sample compositions and characteristics

| Sample No. | Composition | Centrifugation Properties | pH | Rheometric Analysis Viscosity |
|---|---|---|---|---|
| 1 | 6.09 g of (10 ml 12% $CeO_2$ nanoactive soln + 0.2 g *aloe vera* powder + 0.2 g Carbopol 971) + 1 ml coconut oil + 200 µl Tween 80 | No settling | 4.75 | 2.70 at 25 C. 2.53 at 37 C. |
| 2 | 4.43 g essential wholesale shea butter cream + 1 ml 12% $CeO_2$ nanoactive soln + 200 µl PMB30W | Very slight settling | 6.62 | 1.76 at 25 C. 0;.41 at 37 C. |
| 3 | 4.53 g essential wholesale goat milk cream + 1 ml 12% $CeO_2$ nanoactive soln + 200 µl Tween 80 | No settling | 6.38 | 0.29 at 25 C. 0.07 at 37 C. |
| 4 | 6.79 (4.90 ml 12% $CeO_2$ nanoactive soln + 100 µl triethanolamine + 0.1 g *aloe vera* powder + 0.1 g Carbopol 971) + 1 ml coconut oil + 200 µl Tween 80 | No settling | 8.03 | 3.43 at 25 C. 2.47 at 37 C. |
| 5 | 3 ml 12% $CeO_2$ nanoactive soln + 0.06 g *aloe vera* + 0.06 g Carbopol 971 + 556 µl coconut oil + 111 µl Tween 80 | — | 4.71 | 3.87 at 25 C. 2.92 at 37 C. |

TABLE 3-continued

Sample compositions and characteristics

| Sample No. | Composition | Centrifugation Properties | pH | Rheometric Analysis Viscosity |
|---|---|---|---|---|
| 6 | 6.51 g (4.90 ml 12% CeO$_2$ nanoactive soln + 100 μl 1M NaOH + 0.1 g *aloe vera* powder + g Carbopol 971) + 1 ml coconut oil + 200 μl Tween 80 | No Settling But slight water layer at top. | 5.14 | 1.72 at 25 C. 1.38 at 37 C. |
| 7 | 6.61 g (12% CeO$_2$ nanoactive soln + 100 μl triethanolamine + 0.1 g *aloe vera* powder + 0.125 g Carbopol 971) + 1 ml coconut oil + 200 μl Tween 80 | No settling | 7.77 | 4.31 at 25 C. 2.74 at 37 C. |
| 8 | 5 ml 12% CeO$_2$ nanoactive soln + 0.1 g *aloe vera* powder + 2 ml coconut oil + 1 ml Tween 80 + 0.16 g Carbopol 971 | Small White, creamy layer had separated on top, but ceria did not settle out. | 4.52 | 2.89 at 25 C. 2.50 at 37 C. |
| 9 | 1.25 ml 12% CeO$_2$ nanoactive soln + 0.25 ml glycerin + 0.25 ml coconut oil + 0.5 ml safflower oil + 0.5 ml cocoa butter + 0.5 ml emulsifying wax | No phase separation upon centrifugation. | 7.95 | 4.65 at 25 C. 1.93 at 37 C. |

Composition of Sample No. 9 in Table 3 has a high viscosity and good "skin feel," as observed when spread evenly on human skin. This composition also has a good stability and a moderate pH. This composition is an emulsion of water and oil phase. The oil phase comprises safflower oil and fractionated coconut oil, both of which are in the liquid phase at room temperature along with cocoa butter and emulsifying wax, which are both solid at room temperature. The oil phase components were heated to liquefy. The water phase of ceria nanoactive solution and glycerin were also heated to 35° C. The oil phase was added to the water phase and mixed with a spatula. Agitation of the solution was continued for approximately 5 min to create an emulsion and ensure that the phase did not separate while cooling took place. A preferred route of administration of the CONPs for protection of normal skin and tissues of breast cancer patients treated with radiation is a topical administration of CONPs. The topical formulation of the CONPs in this case may be a water-oil emulsion such as described above.

Preliminary studies suggest that these nanoparticles may be a therapeutic regenerative material that will scavenge reactive oxygen species (ROS) that are responsible for radiation-induced cell damage. When biological systems are under high-energy exposure, such as in long-duration space exploration and extravehicular activity, astronauts are exposed to numerous sources of oxidative stress, including radiation, elevated oxygen exposure during extravehicular activity, and physical and psychological stress. When ROS are produced at high levels, cellular components can be damaged. These ROS can be used by biological systems as a defense mechanism against microorganisms and can act as signal transduction and transcription agents in development, stress responses, and programmed cell death. Oxidative stress arises from the strong cellular oxidizing potential of excess ROS, or free radicals. In addition, elevated levels of oxidative damage are related to increased risks for cataracts, cardiovascular disease, and cancer. Therefore, the potential benefit of the proposed radioprotection research is of great significance on multiple levels, one of which is its potential impact on human life. This invention is relevant to the health and quality of life of humans worldwide who are exposed to radiation environments, such as, but not intended to be limited to, astronauts in NASA exposed to particle radiation; military and civilians potentially exposed to radiation in battle, terrorism, or occupational exposure; and patients receiving radiation treatments for cancer.

Example 3

Use of Cerium Oxide Nanoparticles to Increase Pancreatic Cancer Cell Sensitivity to Radiation Yet further, it was determined whether free radical scavenging cerium oxide nanoparticles (CONPs), at an optimal biological dose, sensitize pancreatic cancer cells to radiation. Radiation-induced H$_2$O$_2$ production was significantly increased in the presence of <10 or =10 uM CONPs, whereas the production of H$_2$O$_2$ was significantly decreased in the presence of >20 μM (0.013 mg/kg) CONPs. Radiation-induced ROS production was increased in L3.6pl cancer cells pre-treated with CONPs, which correlated with a significant decrease in cell viability and clone-genicity as compared to radiation alone. Conversely, ROS was decreased in normal hTERT-HPNE cells without impacting cell viability. The volume of pancreatic tumors was reduced by 48% in mice treated with combination therapy compared to radiation alone. Immunohistochemical analysis showed that combination therapy resulted in a significant increase in tumor cell apoptosis. Collectively, our results show that CONPs sensitize cancer cells to radiation and may provide a novel radiation sensitizer for the treatment of human pancreatic cancer.

Figure 25B:
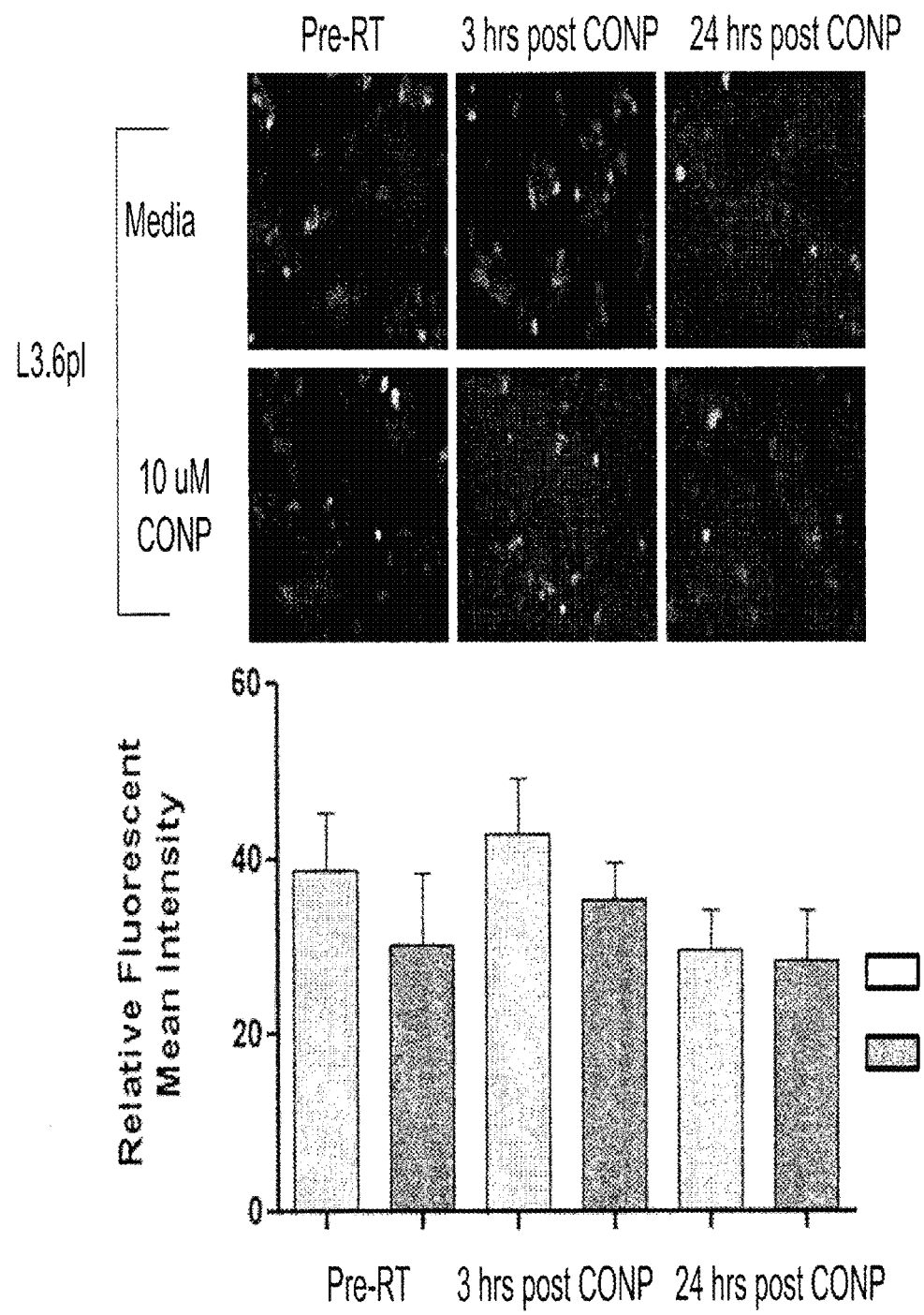

As illustrated with reference to FIGS. 25A and 25B, CONPs selectively increase RT induced ROS in pancreatic cancer cells. With reference to A, in L3.6pl and hTERT-HPNE cells pre-incubated with CONPs, CONPs increased ROS production in pancreatic cancer cells (L3.6pl) lasting up to 24 hours, while transiently reducing ROS production in normal pancreatic cells (HPNE). As illustrated in 8, CONPs added after radiation did not impact ROS production in 13.6pl cells but transiently decreased ROS production in HPNE cells. Yet further, FIGS. 25C and 25D illustrate results from FIGS. 25A and 25B were quantified and graphed to illustrate the changes in ROS level.

FIGS. 26A to 26D illustrate CONPs selectively sensitize pancreatic cancer cells to radiation in vitro. A. Pre-treatment of L3.6pl cells with 10 µM (0.0067 mg/kg) CONPs increased radiation-induced decreases in cell viability by 1.7 fold. B. Pre-treatment of normal pancreatic cells (HPNE) with 10 µM (0.0067 mg/kg) CONPs had no significant impact on radiation-induced decreases in cell viability. C. Pre-treatment of L3.6pl cells with 10 µM (0.0067 mg/kg) CONPs decreased radiation-induced colony formation by 2.4 fold. D. Results from FIG. 26C were quantified and graphed to illustrate the changes in colony formation.

Figure 27:
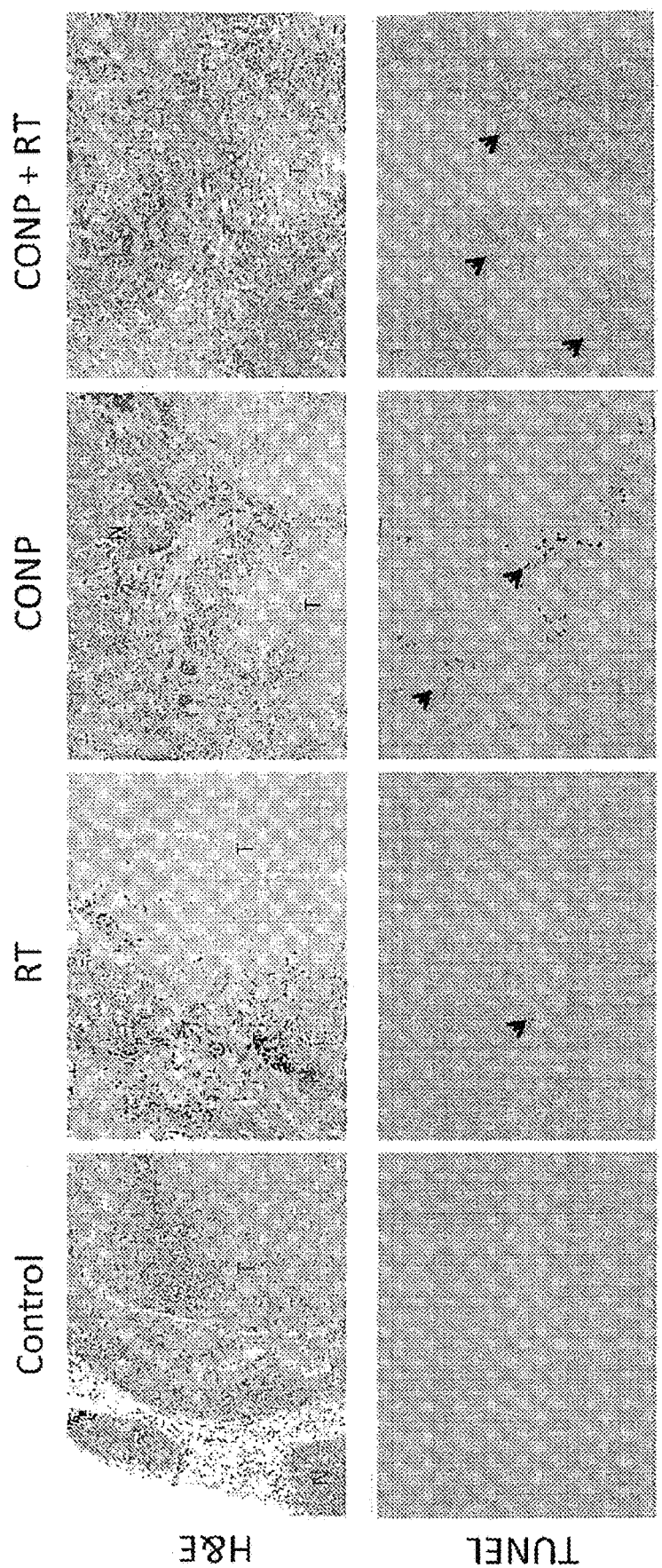
FIG. 27 illustrates CONPs drive radiation induced apoptosis in vivo.

FIG. 27 illustrates CONPs drive radiation induced apoptosis in vivo. H&E and TUNEL staining on tissue sections collected from mice showed CONP and, even more dramatically, combination (CONP and RT) treatment increased the amount of normal tissue present and the amount of radiation-induced apoptosis at the time of termination.

Detailed necropsy revealed that all of the mice had tumors in the pancreas. The data summarized in Table 4 shows that the combination of CONP with radiation produced the greatest decrease in tumor weight as compared with radiation alone (0.97 g and 1.31 g, respectively; P<0.005). Body weight was not changed among all treatment groups as compared with control mice. No visible liver metastases were present (enumerated with the aid of a dissecting microscope) in any of the treatment groups.

TABLE 4

CONP increases pancreatic cancer cell sensitivity to radiation
Pancreatic Tumors

| Treatment Group | Tumor Incidence | Tumor Weight (g) | | Body Weight (g) | |
| --- | --- | --- | --- | --- | --- |
| | | Mean | Range | Mean | Range |
| Vehicle Control | 15/15 | 1.31 | 3.41-5.88 | 27.89 | 22.35-31.66 |
| CONP (15 µM) | 15/15 | 1.39 | 2.44-3.90 | 26.38 | 20.06-37-25 |
| Radiation (30 Gy) | 15/15 | 1.38 | 2.67-4.70 | 25.89 | 20.20-31.15 |
| CONP (15 µM) + Radiation (30 Gy) | 15/15 | 0.97* | 1.30-2.78 | 26.59 | 20.88-30.93 |

As above addressed, the teachings of the present invention address a novel approach for the protection of normal tissues against radiation-induced damage by using cerium oxide ($CeO_2$) nanoparticles. $CeO_2$ nanoparticles (CONPs) have been tested for their ability to serve as free radical scavengers to render protection against chemical, biological, and radiological insults that promote the production of free radicals. It was suggested that the unique structure of $CeO_2$ nanoparticles, with respect to valence and oxygen defects, promotes cell longevity and decreases toxic insults by virtue of its antioxidant properties, prevents the accumulation of reactive oxygen species (ROS), and thereby prevents the activation of the apoptotic response and cell death.

Example 4

Use of Cerium Oxide Nanoparticles for Protection of Salivary and Skin Tissue from Radiation-Induced Damage Previous work has tested the safety and ability of CONPs to confer radioprotection in a murine model. CONPs are well tolerated and appear to decrease the incidence of pneumonitis in athymic nude mice. In the instant disclosure, it is hypothesized that CONPs represent a novel approach to the protection of salivary and skin tissue from radiation-induced damage and test their efficacy as a new radioprotective compound on athymic nude mice receiving radiotherapy to the head and neck.

Figure 28A:
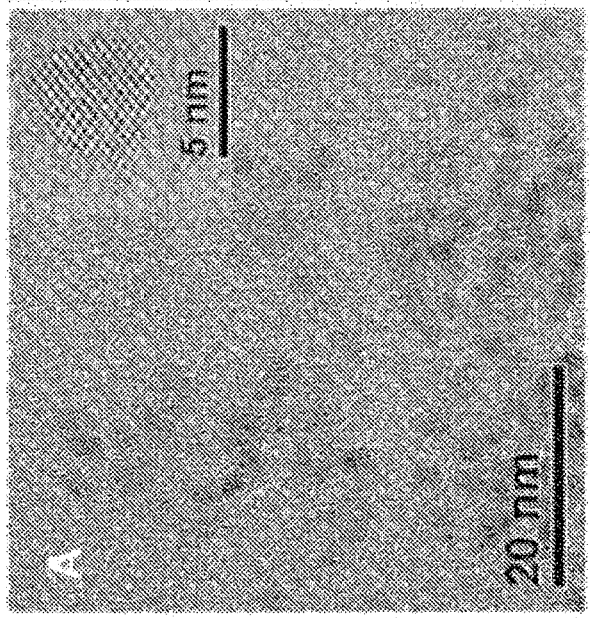
Figure 28B:
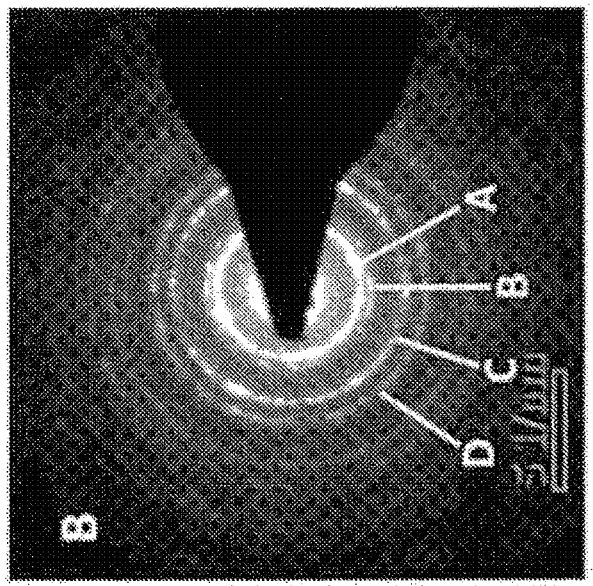
Figure 28C:
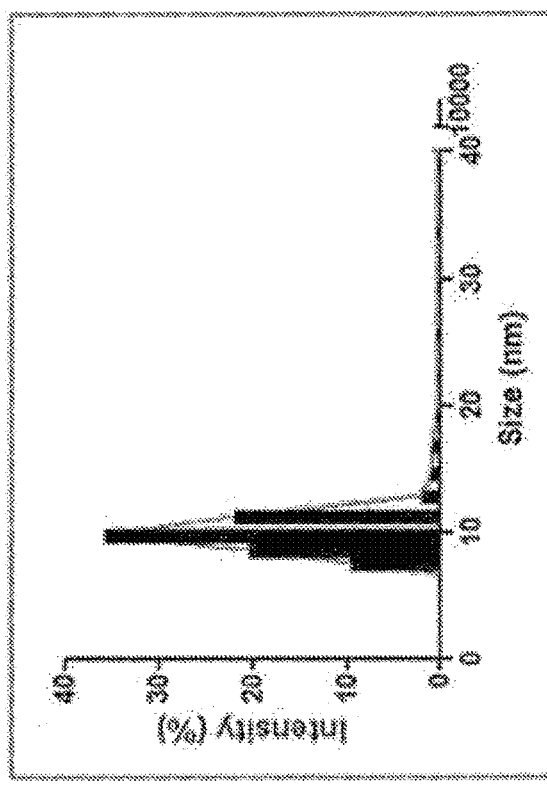

CONPs Synthesis and Characterization:

The cerium oxide nanoparticles were synthesized using a micro-emulsion process as previously described. Synthesized ceria oxide was examined by high-resolution transmission electron microscopy (HRTEM) to determine individual particle and agglomerate size. The physiochemical properties of the synthesized nanoparticles are illustrated in FIGS. 28A-28C. FIG. 28A illustrates HRTEM image of nanoceria (CONPs) showing $CeO_2$ nanoparticles size range of 3-5 nm, in the inset high magnification image of the nanoparticle. FIG. 28B illustrates a SEAD pattern of a fluorite crystal structure where A, B, C and D corresponds to different lattice pattern 111, 200, 220 and 311, respectively. FIGS. 28A and 28C taken together illustrate the radius of CONPs in the size range 5 nanometers to about 20 nanometers nanometers).

Animals: Female athymic nude mice (NCI-nu) were purchased from the Animal Production Area of the National Cancer Institute Frederick Cancer Research and Development Center (Frederick, Md.). Athymic nude mice were housed and maintained in the Cancer Research Institute's American Association for Accreditation of Laboratory Animal Care (AAALAC) accredited animal facility which exceeds the national requirements for animal care, with two conventional mouse rooms, two nude mouse rooms and one quarantine room. The use of animals for this study was and is approved by the MD Anderson Cancer Center Orlando Institutional Animal Care and Use Committee (IACUC) under the IACUC protocol number 09.06.01. Mice were used in accordance with institutional guidelines when they were 8-12 weeks of age.

Radiation and CONPs Treatment of the Head and Neck Region of Athymic Nude Mice:

The IC160 X-ray irradiation system (Kimtron Inc., Woodbury, Conn., USA) was employed to irradiate the head and neck region of the mice. The animals were anesthetized and placed in the supine position under the radiation focal spot. Irradiation was performed at room temperature with the use of a 160 kV X-ray generator unit operating at 18.5 mA at a rate of 2.74 Gy/sec. CeO2 nanoparticles were delivered in 100 µL of saline by intraperitoneal (i.p.) injection as previously reported. A pilot study was performed in order to characterize the effects of radiation exposure to the head and neck area on salivary flow. The athymic mice were randomized into 5 groups (N=1O/group). 1) no radiation (control group); 2) single radiation dose of 12.5 Gy; 3) single radiation dose of 15 Gy; 4) single radiation dose of 17.5 Gy; 5) single radiation dose of 20 Gy. Six weeks after the completion of radiation a sialometry analysis was performed.

In subsequent experiments, athymic nude mice cohorts underwent a two by three randomization. The mice were initially randomized into two cohorts (N=30/cohort): A) no radiation (mice were anesthetized and placed in the irradiator but did not receive radiation); B) 30 Gy of radiation fractionated in 6 doses (5 Gy/dose) given every other day over the course of two weeks. Then, each cohort was randomized into three groups (N=1O/group): 1) bi-weekly intraperitoneal (i.p.) injections of saline for two weeks before radiation treatment and during the course of radiation treatment (control group); 2) bi-weekly i.p. injections of 15 nM (0.00001 mg/kg) CeO$_2$ nanoparticles for two weeks before the radiation treatment and during the course of radiation treatment; 3) bi-weekly i.p. injections of 15 µM (0.01 mg/kg) CeO$_2$ nanoparticles for two weeks before initiating radiation therapy and during the course of radiation therapy. A total of 8 injections of CeO$_2$ nanoparticles were given; four injections during the two weeks prior to radiation and four injections during the two week radiation course (i.e., two injections per week).

Radiation-Induced Damage—Evaluation Criteria:

Two independent double-blinded researchers graded radiation-induced dermatitis and hyperpigmentation at 1, 4, and 12 weeks after radiation therapy according to the National Cancer Institute (NCI) Common Toxicities Criteria's (CTC v.3.0 Table 3).

Anesthesia:

During evaluation of radiation dermatitis and saliva collection the mice were anesthetized with i.p. injections of Ketamine (100 mg/ml) and Xylazine (20 mg/ml) cocktail (1 µl/g of body weight).

Sialometry Analysis:

In the first set of experiments during which mice received escalating doses of single fraction radiation (12.5, 15, 17.5 and 20 Gy) without the administration of nanoparticles, mice were sacrificed at six weeks after the completion of radiation. In the next set of experiments, in which mice received 30 Gy of fractionated radiation (5 Gy/dose) with and without nanoparticles mice were terminated 90 days after the completion of radiation. Once anesthetized, the mice were weighed and salivary gland function was stimulated using subcutaneous injection of pilocarpine solution (50 mg/ml) at 2 mg/kg of body weight. Saliva collection began 10 minutes after the pilocarpine administration. Animals were placed in a vertex position facing up, and a pre-weighted 75-mm heparinized micro-hematocrit capillary tube (Drummond, Broomall, Pa.) was placed into the oral cavity. Whole saliva was collected for a 10 minute period and the amount of saliva collected was determined gravimetrically.

Necropsy Procedures and Histological Studies:

After the analyses of radiation-induced dermatitis and stimulated salivary flow were completed, all mice were sacrificed using a CO$_2$ chamber. The animals' body weight was recorded after sacrifice. All tissue necropsy, Hematoxylin and Eosin (H&E), and TUNEL analyses were performed on mice that received 30 Gy fractionated radiation (i.e., with and without 15 nM (0.00001 mg/kg) and 15 µM (0.01 mg/kg) CeO$_2$ nanoparticles). Harvested specimens from the oral cavity and neck included the tongue and adjacent soft tissues, parotid glands, sublingual glands, submandibular glands, and the regional lymph nodes. For H&E staining, these tissues were fixed in formalin, embedded in paraffin, and serially sectioned at 200 µm.

Paraffin-embedded tissues were used for TUNEL staining. TUNEL-positive cells were detected using the DeadEnd Colorimetric TUNEL System (Promega, Madison, Wis.).

Immunohistological microscopy was performed using a 40× objective on a Nikon E400 microscope (Nikon Instruments, Melville, N.Y.). Routine procedures were used to capture images, which were processed on Adobe Photoshop. Histological analysis was performed in collaboration with the pathology team of MD Anderson—Orlando. Immunopositive cells for TUNEL expression were counted per animal using a 40× objective over 10 individual slides and the average values were calculated.

Statistical Analysis:

]Radiation-induced dermatitis and sialometry experiments were performed in triplicates and the data were presented as mean±SEM. Statistical analysis was done using Student's t test, assuming equal variance, and P value was calculated based on two-tailed test. A p value of <0.05 was considered statistically significant.

RESULTS included:

Validation of a Radiation-induced Xerostomia Model:

Athymic nude mice were exposed to different doses of single fraction radiation (12.5 Gy, 15 Gy, 17.5 Gy or 20 Gy) and sialometry analysis was performed (FIGS. 29A-29C). Results indicate a dose dependent decrease in salivary function which is consistent with clinical observations reported on human patients undergoing radiotherapy to the head and neck.

FIGS. 29A-29C illustrate radiation effects on salivary production in the absence and presence of CONPs. (FIG. 29A) Stimulated sialometry analysis of salivary gland function 6 weeks after single fraction radiation to the head and neck area (12.5 Gy, 15 Gy, 17.5 Gy or 20 Gy). The results indicate a dose dependent decrease in salivary function with the greatest decrease in stimulated salivary flow after 15-17.5 Gy of single fraction radiation. (FIG. 29B) Effects of CONPs on salivary flow protection after radiation exposure. The results demonstrate a statistically significant difference in salivary flow production between the control group that received 30 Gy/6 fractions of radiation and mice treated with 30 Gy/6 fractions of radiation plus concomitant CONPs. (FIG. 29C) Effects of CONPs on skin hyperpigmentation after radiation exposure using the NCI common terminology criteria for adverse events (CTCAE v.3.0). Mice treated with 15 nM (0.00001 mg/kg) CONPs demonstrated a lower incidence of grade II (33.33%) and a higher incidence of Grade I (66.67%) dermatitis. In contrast, mice treated with 15 µM (0.01 mg/kg) CONPs had an equal incidence of Grade I and II hyperpigmentation (50% each).

The greatest decrease in stimulated salivary flow was observed after 15-17.5 Gy of single fraction radiation. In order to simulate a more clinically relevant scenario, a fractionated schedule biologically equivalent to this single fraction regimen was devised. By a series of Biologically Effective Dose (BED) calculations [25], 30 Gy in 6 fractions of 5 Gy was used in subsequent experiments. This regimen has a BED of 45.0 Gy10 for acute effects and 80Gy3 for late effects, which compare favorably to the BED of a 15-17.5 Gy single fraction radiation regimen.

Furthermore, 30 Gy in 6 fractions would result in sufficient soft tissue effects and salivary gland dysfunction allowing adequate testing and evaluation of radioprotective properties of CeO$_2$ nanoparticles.

Effects of Cerium Oxide Nanoparticles on Salivary Function in the Absence of Radiation:

Sialometry analysis on non-radiated athymic nude mice previously exposed to i.p. injections of CONPs at 15 nM (0.00001 mg/kg) and at 15 µM (0.01 mg/kg) yielded no statistical difference in the mean salivary volume collected over 10 minutes, when compared to control no-nanoparticles (Saline) [Saline group vs. 15 nM (0.00001 mg/kg) group–p Value: 0.1007; Saline group vs. 15 µM (0.01 mg/kg) group–p Value: 0.9856; 15 nM (0.00001 mg/kg) group vs. 15 µM (0.01 mg/kg) group–p Value: 0.1159]. While the saline control group had a mean volume of 313 µL/10 min, the groups exposed to 15 nM (0.00001 mg/kg) and 15 µM (0.01 mg/kg) Ce02 nanoparticles had mean volumes of 286 µL/10 min and 312 µL/10 min, respectively.

Effects of Cerium Oxide Nanoparticles on Athymic Nude Mice Exposed to Radiation to the Head and Neck Region: The radiated groups that received either low concentration (15 nM; 0.00001 mg/kg) of CONPs or high concentration (15 μM; 0.01 mg/kg) of CONPs had an increase in salivary flow production when compared to the "no nanoparticle" radiated group 12 weeks after radiation exposure. Sialometry analysis demonstrated a statistically significant difference in salivary flow production between the control group that received 30 Gy/6 fractions of radiation and mice treated with 30 Gy/6 fractions of radiation that received concomitant treatment with CONPs.

When the 15 nM (0.00001 mg/kg) and 15 μM (0.01 mg/kg) CONPs radiated groups were individually compared to the "no nanoparticle" radiated control group, there was a statistically significant difference in the stimulated salivary flow, favoring the 15 μM (0.01 mg/kg) $CeO_2$ group (P value: 0.0003, 95% CI: −128.0 to −52.90).

All of the skin hyperpigmentation observed in mice treated with radiation alone was recorded as Grade II. In comparison, mice treated with 15 nM CONPs demonstrated a lower incidence of grade II (33.33%) and a higher incidence of Grade I (66.67%) hyperpigmentation. Mice treated with 15 μM (0.01 mg/kg) Ce02 nanoparticles had an equal incidence of Grade I and II hyperpigmentation (50% each).

Figure 30:
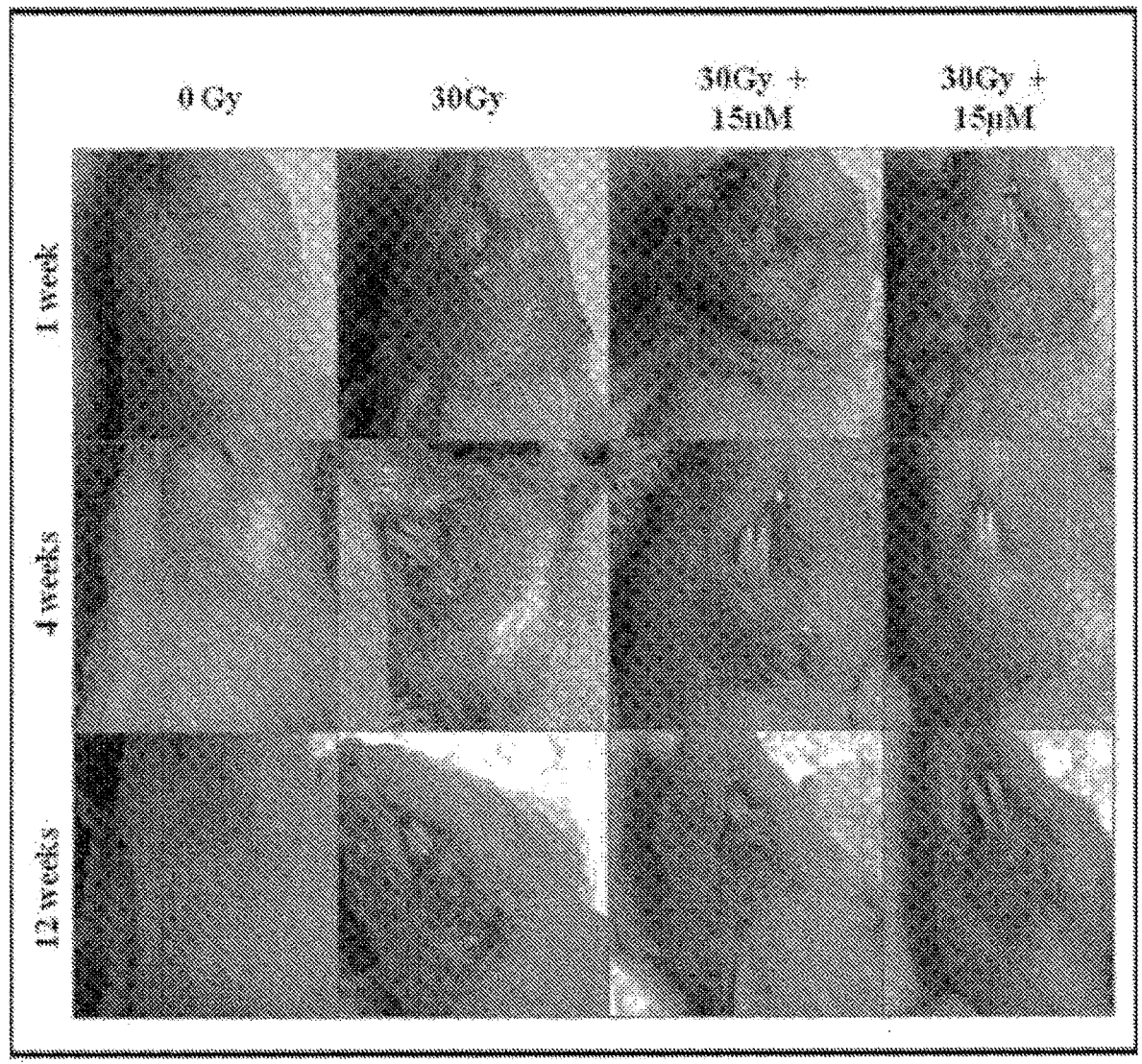
FIG. 30 illustrates macroscopic evaluation of radiation-induced dermatitis of athymic mice exposed to 30 Gy in 6 fractions to the head and neck region.

An inverse correlation was observed between the incidence of Grade 3 radiation induced dermatitis and the concentration of $CeO_2$ nanoparticles given (FIG. 30). The incidence of Grade 3 dermatitis 1 week after radiation was decreased in the 15 μM (0.01 mg/kg) CONPs group compared to the non-CONPs controls (10% vs. 100% incidence of Grade 3 dermatitis, respectively). This effect was not appreciated in the 15 nM CONPs group. Furthermore, animals exposed to radiation and either 15 nM (0.00001 mg/kg) or 15 μM (0.01 mg/kg) concentration of CONPs showed swifter resolution of radiation dermatitis when compared to the control "no nanoparticle" radiated group. For example, complete healing was observed in 60% of animals pre-treated with 15 μM (0.01 mg/kg) of CONPs before radiation, vs 10% on the radiated control group, at 12 weeks post-radiation (see FIG. 30).

Effects of Cerium Oxide Nanoparticles (CONPs) on the Apoptotic Index of Salivary Glands Parenchymal Cells After Radiation to the Head and Neck Region:

The parotid, sublingual and submandibular glands were independently analyzed and the acinar cell apoptotic index was determined using TUNEL analysis. Our results indicate a dose dependent decrease in the apoptotic index for the individual glands after radiation, indicative of the radioprotective nature of the nanoparticles (see FIGS. 31A and 31B).

Figure 31:
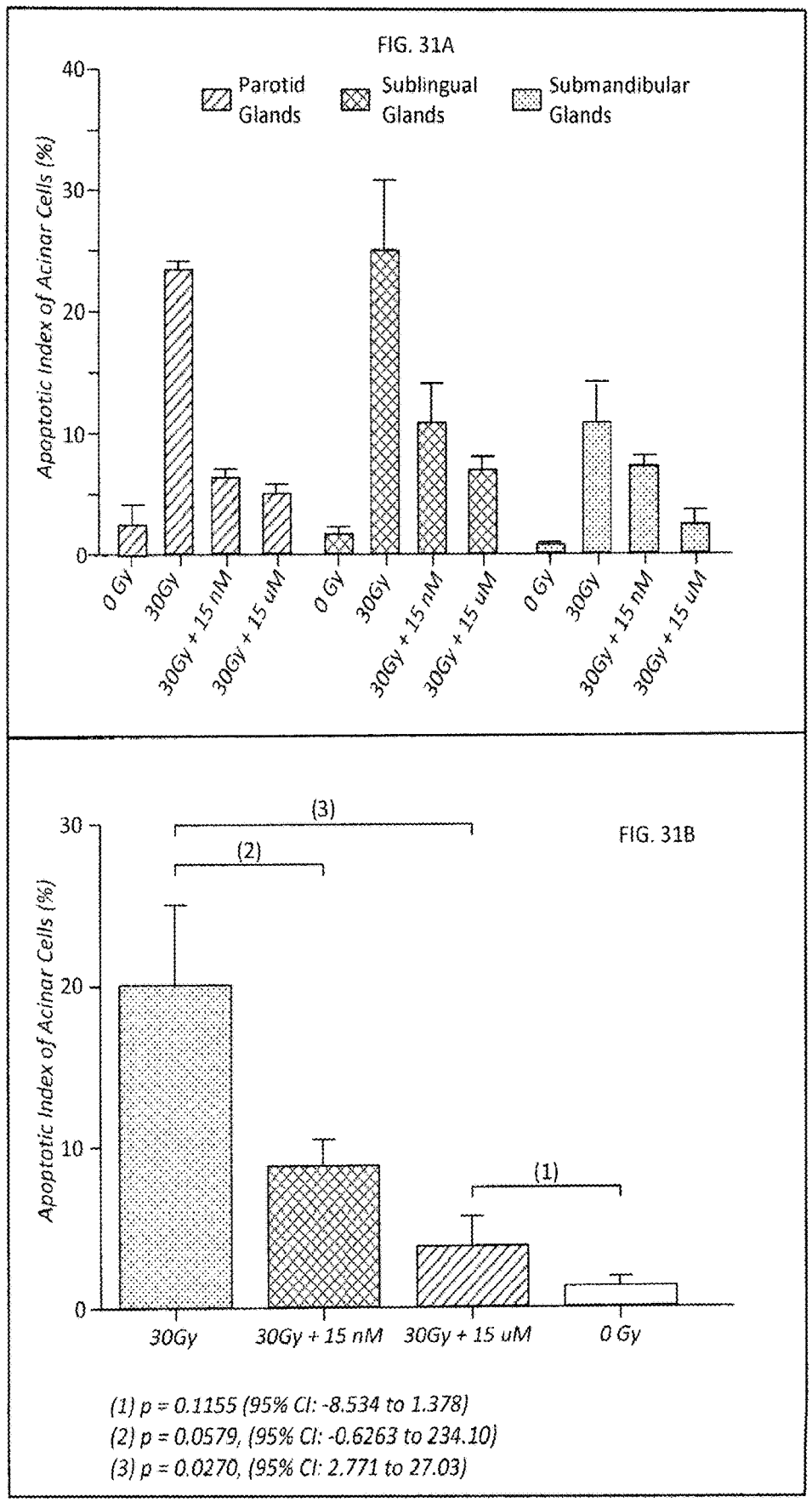

FIGS. 31A and 31 B illustrate effects of cerium oxide nanoparticles on the apoptotic index of salivary glands parenchymal cells after radiation to the head and neck region. (FIG. 31A) Radiation-induced apoptosis of salivary glands (Parotid, Sublingual and Submandibular) parenchymal cells. The parotid glands of mice that given radiation, without CONPs treatment, showed an increase in apoptotic index (22%) compared to those that were not treated with radiation (2.2%) and to glands of mice that received either 15 nM (0.00001 mg/kg) or 15 μM (0.01 mg/kg) CONPs plus radiation (5.32% and 4.25%, respectively). Non-irradiated sublingual glands had a baseline apoptotic index of 1.87%, which increased to 26% after radiation. Pre-treating with either 15 nM (0.00001 mg/kg) or 15 μM (0.01 mg/kg) CONPs resulted in a reduction in the magnitude of apoptotic index elevation to 11.8% and 7.2%, respectively after radiation. Non-irradiated submandibular glands had a baseline apoptotic index of 0.2%. While radiation increased the index to 12.2%, by pre-treating with CONPs (15 nM (0.00001 mg/kg) or 15 μM (0.01 mg/kg)) the magnitude of elevation was decreased to 7.4% and 2.6% respectively. (FIG. 31B) Complementary analysis of the effects of CONPs combined with radiation on all major salivary gland yielded a similar response as that shown in FIG. 31A.

Complementary analysis of the effects of CONPs combined with radiation on all major salivary glands yielded a similar response. The overall apoptotic index baseline of acinar cells for the nonradiated group was 1.43%, while radiation-induced damage increased the apoptotic rate to 19.91%. Meanwhile, after treatment with radiation, both (15 nM and 15 μM; 0.00001 mg/kg and 0.01 mg/kg)) CONPs treated groups exhibited an apoptotic index of 8.17% and 4.67%, respectively. Statistical analysis demonstrated a significant difference between the "no-nanoparticle" treated group and the 15 μM (0.01 mg/kg) Ce02 treated group (p Value: 0.0270, 95% CI: 2.77 to 27.03). Lastly, a comparison between the group that received a combination of nanoparticles plus radiation and the control group (i.e. "no nanoparticle" "no radiation" controls) was performed to quantify the degree of radioprotection from apoptotic death compared to virgin salivary tissue. Comparison of the apoptotic index of the 15 μM (0.01 mg/kg) CONPs group that received radiation versus the "no radiation" "no-nanoparticle" control group showed no statistical difference (p Value: 0.1155, 95% CI: −8.534 to 1.378).

On the other hand, the apoptotic index of the 15 μM (0.01 mg/kg) CONPs treated group that did not receive radiation and the non-radiated "no-nanoparticle" control group showed no statistical difference between them. These results suggest that exposure to $CeO_2$ nanoparticles does not result in adverse effects to acinar cells.

Figure 32:
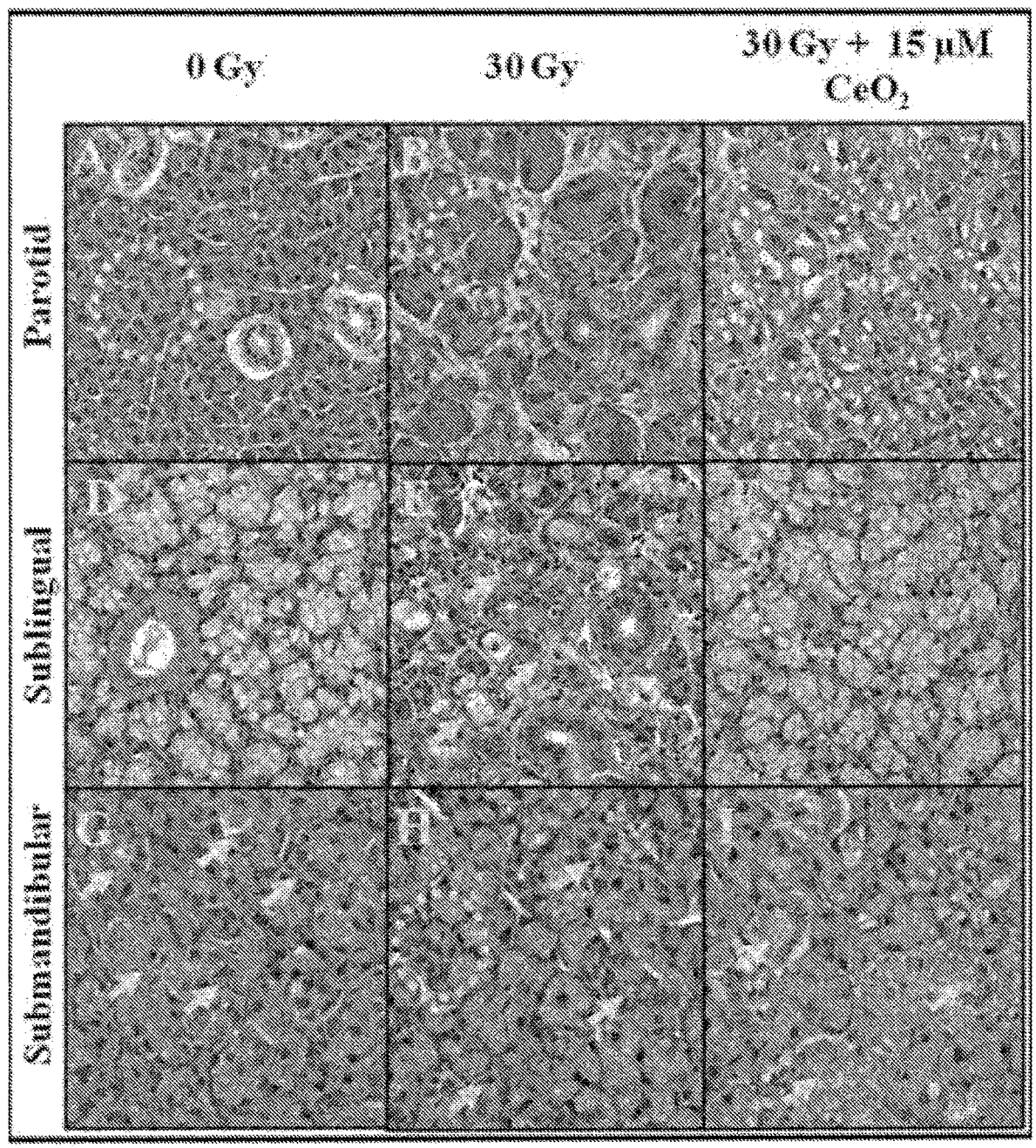
FIG. 32 illustrates a hematoxylin and eosin (H&E) analysis of radiation-induced damage on salivary glands parenchymal cell architecture.

H&E Evaluation of Radiation-Induced Damage on Salivary Gland Cell Architecture:

To determine the degree of radiation-induced damage to the salivary glands, the tongue, regional lymph nodes and soft tissue from the neck, these tissues were harvested and processed for H&E staining. The glands from mice in the irradiated control group (radiation alone) showed visible damage to their morphological architecture, with extensive macrophage and lymphocyte invasion. In contrast, the neck specimens from irradiated mice receiving either 15 nM (0.00001 mg/kg) (data not shown) or 15 μM (0.01 mg/kg) CONPs showed vacuolization of the acinar cells, but the overall morphology of the acinar tissue and number of acinar cell nuclei appears to be preserved (see FIG. 32). FIG. 32 illustrates H&E Analysis of Radiation-Induced Damage on Salivary Glands Parenchymal Cell Architecture. Shown are histologic evaluations using hematoxylin and eosin staining of harvested non-irradiated salivary gland specimens (A,D,G) [at 40× magnification]; gland specimens radiated with 30 Gy in 6 fractions (B,E,[at 40× magnification]; and specimens pretreated with 15 μM (0.01 mg/kg) of CONPs and subsequently irradiated (C,F,I) [at 40× magnification]. Morphologic analysis of parotid glands (Panel A: non-treated, non-irradiated group [yellow circle]) demonstrated preservation in the serous acinar architecture in the 15 μM (0.01 mg/kg) of CONPs irradiated group (Panel C, yellow circle) in contrast to radiation only specimens (Panel B, yellow circle) which shows destruction (yellow arrow) and hypertrophy of serous acinus. Sublingual gland analysis shows no alterations between the mucinous acinar structure of the non-treated, non-irradiated group and the 15 μM (0.01 mg/kg) of CONPs irradiated group (Panel D & F, yellow circle) when compared to the fibrotic changes, secondary to radiation, damage seen in the radiated only group (Panel E, yellow arrows). While the serous acinus architecture was preserved in the submandibular specimens there was a higher incidence of inflammatory cells (yellow circle) in the radiation only group. Meanwhile, the number of interlobular ducts was greatly decreased in the radiation only group (Panel H, yellow arrows) when compared to the non-treated, non-irradiated control group and the 15 µM (0.01 mg/kg) of $CeO_2$ irradiated group (Panel G & I, yellow arrows).

Radiation-induced xerostomia, dermatitis, fibrosis, and mucositis are common and often severe complications of radiotherapy for head and neck cancer. Presently, Amifostine is the only agent in clinical use. Unfortunately, its short half-life, daily dosing requirements, and cost have been barriers to the widespread use of Amifostine during radiotherapy for head and neck cancer. As a result, there remains a clinical need for a well-tolerated, facile, long-lasting, and cost-effective radioprotective agents; the "panacea" of radioprotection remains to be found.

Previous work has demonstrated the ability of $CeO_2$ nanoparticles to provide radioprotection to normal breast (CRL-8798) cells, but not to human breast cancer (MCF-7) cells at concentrations greater than 50 nM. Extension of this work demonstrated that Ce02 nanoparticles protect gastrointestinal epithelium against radiation induced damage.

This work also suggests that CONPs confer radioprotection by acting as a free radical scavenger and by increasing the production of superoxide dismutase 2. Animal studies have demonstrated that CONPs are well tolerated in live animals. In addition, lung tissues harvested after whole-lung irradiation demonstrated no histological evidence of pneumonitis and fibrosis in athymic mice treated with 15 nM CONPs compared to "no nanoparticle" controls. These results show that CONPs may play a key role in the protection of tissues in the head and neck against radiation-induced damage that is possibly concentration dependent.

In this study, the assessment of stimulated sialometry strongly demonstrated improved salivary production in all CONP treated groups compared to the "no-nanoparticle" radiated treated group. In the 15 µM (0.01 mg/kg) CONPs treated group the mean salivary flow after radiation was 65% of the non-radiated control, whereas in the 15 nM (0.00001 mg/kg) CONP-treated group the stimulated flow was approximately 50% of the non-radiated control. Therefore, CONPs appear to confer some degree of preservation of stimulated salivary function after radiation.

It is worth noting that salivary flow rates in the cohort of mice treated in the single fraction experiment (see FIG. 29A) were higher (even after 15-20Gy single fraction dose) than the flow rates in the fractionated experiment (see FIG. 298). The argument could be made that hyposalivation is greater at three months compared to six weeks post-radiation. However, this is not what is suggested in the clinical literature.

Clinical studies suggest that xerostomia is more intense immediately after radiation and begins to improve after a few months.

The explanation for this incongruence with clinical data on humans is unclear. The mice in the first experiment received single fraction radiation, which may be of different biologic significance than the fractionated course in the second experiment. Hence, it is difficult to compare sialometry results between the two groups.

There was a decreased incidence of radiation dermatitis in mice treated with 15 µM (0.01 mg/kg) CONPs that was not seen in the 15 nM (0.00001 mg/kg) CONPs group. However, the recovery from acute radiation dermatitis appeared to be more rapid in all groups that were pretreated with CONPs.

TUNEL analysis demonstrated a decrease in cell death that was inversely proportional to the CONPs concentration. Lastly, it appears that salivary tissue architecture was preserved after radiation in mice receiving the highest concentration (15 µM; 0.01 mg/kg) of nanoparticles.

Example 5

Effects of Cerium Oxide Nanoparticles in Combination with Radiation+Paclitaxel on Lung Cancer CRL5803 Cells The combination therapy of Cerium Oxide Nanoparticles with Radiation and chemotherapeutic agent Paclitaxel was assayed in a lung cancer cell line.

Experimental Design

Lung cancer CRL5803 cells were plated in a 96 well plate for 24 hours. (density ~2000 cells/well). At time=0, culture media was changed and cells exposed to the following treatment conditions.

Control

5Gy Radiation

100 µg Paclitaxel 10 nM Cerium Oxide nanoparticles in combination with radiation and paclitaxel At 24 h, 48 h, 72 h and 96 h after treatment, cell viability was measured using the Cell-Titer Glo Luminescent Cell Viability Assay and plates were read using an Optima microplate reader.

Figure 33:
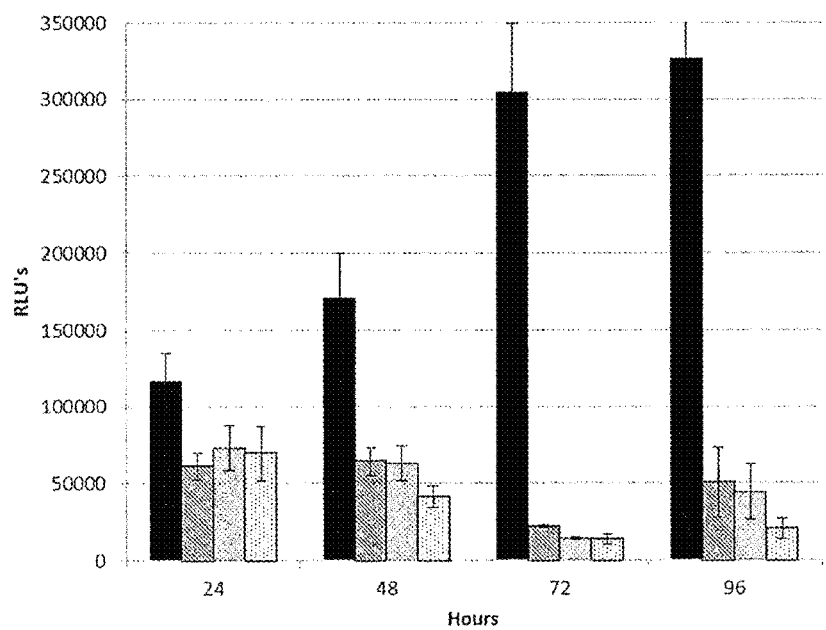
FIG. 33 provides a graph demonstrating the effect of CONPs in combination with radiation and paclitaxel on lung cancer cell viability over a course of 96 hours. Legend: Black bars–control (no treatment), hatched bars–radiation, gray bars–paclitaxel, dotted bars–CONPs+Radiation+Paclitaxel.

The results shown in FIG. 33 show the effectiveness of the combination therapy on lung cancer cell viability as measured by relative light units (RLU) on Optima.

Example 6

Pilot Study of Cerium Oxide Nanoparticles in Combination with Radiation and Chemotherapy in a Mouse Hepatitis Model The Effect of combination therapy (CONPs, radiation, chemotherapy) was studied in a mouse model of hepatitis.

Mice were assigned to the following treatment groups.

| | |
|---|---|
| Saline Control | n = 3 |
| $CeO_2$ nanoparticles (15 µM i.p.) | n = 3 |
| Paclitaxel (100 µg) | n = 3 |
| Radiation 30 Gy | n = 3 |
| Radiation 30 Gy + CeO2 nanoparticles (15 µM i.p.) | n = 3 |
| Radiation 30 Gy + Paclitaxel (100 µg) | n = 3 |
| Radiation 30 Gy CeO2 nanoparticles (15 µM i.p.) + Paclitaxel (100 µg) | n = 3 |

Nanoparticles were administered 2 weeks prior to radiation treatment, during radiation treatment and two weeks after radiation treatment. Cerium Oxide nanoparticles (100 µL i.p. of a 15 µM solution on days 1 and 3). Radiation (30 Gy) was given as a single dose on day 2 of treatment weeks. Paclitaxel (100 µL i.p. of a 100 µg solution) was administered twice on day 2 and 4.

Two weeks after radiation treatment, livers were necropsied and analyzed for histological changes and photographed for analysis.

Figure 34:
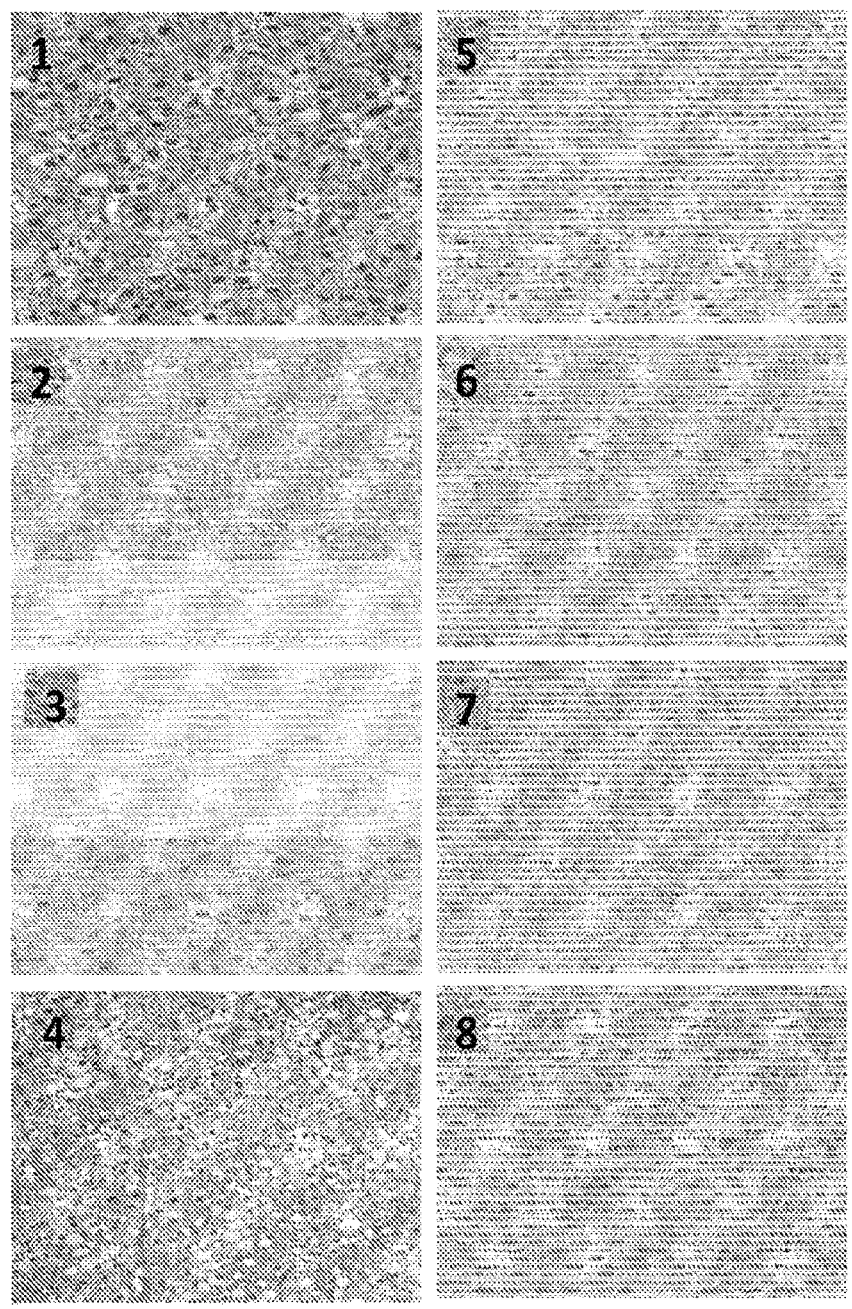
FIG. 34 provides a series of photomicrographs demonstrating mouse liver pathology collected 2 weeks after radiation treatment. Legend: 1) untreated liver, 2) CONPs, 3) CONPs+Radiation, 4) 30 Gy Radiation, 5) CONPs+Paclitaxel, 6) CONPs+Paclitaxel+Radiation, 7) Paclitaxel, 8) Radiation+Paclitaxel.

Results:

As shown pictorially in FIG. 34, the following histological results were observed with each treatment.

| Treatment | Histology |
|---|---|
| Normal Liver | Normal Histology |
| CeO$_2$ nanoparticles | Minimal changes with very little mitosis |
| CeO$_2$ nanoparticles + Radiation (30 Gy) | Minimal changes with rare necrotic hepatocytes |
| Radiation (30 Gy) | Diffuse ballooning degeneration of the hepatocytes with scattered individual hepatocyte necrosis/apoptosis |
| CeO$_2$ nanoparticles + Paclitaxel | Minimal changes, limited mitosis |
| CeO$_2$ nanoparticles + Paclitaxel + Radiation (30 Gy) | Minimal changes, rare necrotic hepatocytes |
| Paclitaxel | Focal extramedullary hematopoiesis, rare necrotic hepatocytes |
| +Paclitaxel + Radiation (30 Gy) | Extensive extramedullary hematopoiesis, increases nuclear/cytoplasm ratio, increased eosinophilia in cytoplasm, increase in binucleated hepatocytes, rare necrotic hepatocytes |

Example 7

Figure 35:
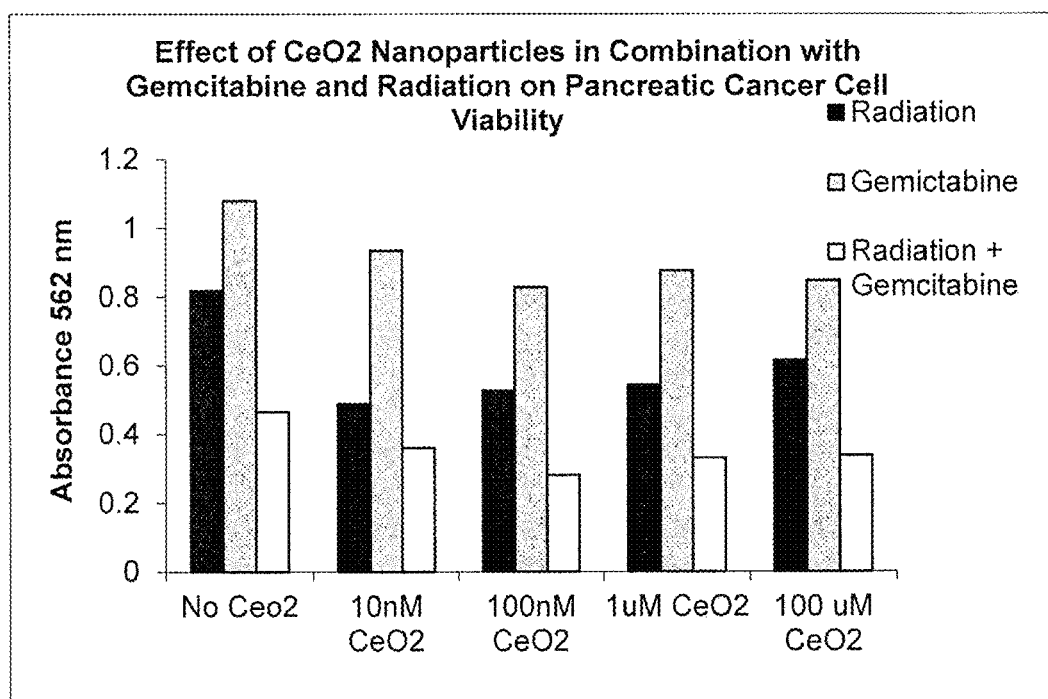
FIG. 35 provides a graph showing the effect of CONPs in combination with gemcitabine and radiation on pancreatic cancer cell viability. Legend: black bars–Radiation; Gray bars–Gemcitabine, white bars–radiation and gemcitabine

Effect of Cerium Oxide Nanoparticles in Combination with Radiation+Gemcitabine on Pancreatic Cancer L3.6PL Cells The combination therapy of Cerium Oxide Nanoparticles with Radiation and chemotherapeutic agent Gemcitabine was assayed in a pancreatic cancer cell line.
Experimental Design
Pancreatic cancer L3.6PL cells were plated in a 96 well plate for 24 hours. (density ~2000 cells/well). At time=0, culture media was changed and cells exposed to the following treatment conditions.
Control
5Gy Radiation
50 ng/ml Gemcitabine
Varying concentrations of Cerium Oxide nanoparticles (0, 10 nM, 100 nM, 1 µM, and 100 µM) were assayed in combination with radiation and Gemcitabine
At 96 h after treatment, cell viability was measured using the Cell-Titer Glo Luminescent Cell Viability Assay and plates were read using an Optima microplate reader.
The results shown in FIG. 35 show the effectiveness of the combination therapy on pancreatic cancer cell viability as measured by relative light units (absorbance 562 nm) on Optima. Black bars depict radiation with nanoparticles. Gray bars depict Gemcitabine with nanoparticles. White bars depict combination of radiation+Gemcitabine with nanoparticles.

Example 8

Effect of Cerium Oxide Nanoparticles in Combination with Radiation+Gemcitabine on Breast Cancer MDA-231 Cells The combination therapy of Cerium Oxide Nanoparticles with Radiation and chemotherapeutic agent paclitaxel is assayed in a breast cancer cell line MDA-231. Other cell lines MDA-431, MDA-435, A431 may also be used. These cell lines are human in origin and are used in cell based studies to determine the efficacy of cerium oxide nanoparticles with and without chemotherapy and radiation.
Experimental Design
Breast cancer MDA-231 cells are plated in a 96 well plate for 24 hours. (density ~2000 cells/well). At time=0, culture media is changed and cells exposed to the following treatment conditions.
Control
5Gy Radiation
100 µg Paclitaxel
Varying concentrations of Cerium Oxide nanoparticles (0, 10 nM, 100 nM, 1 µM, and 100 µM) are assayed in combination with radiation and Paclitaxel
At 96 h after treatment, cell viability is measured using the Cell-Titer Glo Luminescent Cell Viability Assay and plates are read using an Optima microplate reader.
Orthotopic animal models such as athymic nude mice that tolerate the implantation or injection of the human cells are used to confirm cell culture results. Once the cell lines are injected into the organ in the mice, in which they originated from the human (i.e. breast mammary fat pad or lung tissue), the mice are then treated similarly. Tumor growth/tumor volume/tumor weight (to determine efficacy of the agents on the growth of the tumor), body weight (to determine toxicity) and survival (to determine tolerability) are measured. Histology and pathology examination is performed on the orthotopic cancer tissue and surrounding normal tissue to determine changes in cell death, cell proliferation, protection by way of skin burns for external tissue, fibrosis for lung tissue, changes in proteins and changes in cell death or survival pathways using established methods.

Example 9

Effect of Cerium Oxide Nanoparticles is Combination with Radiation+Gemcitabine on Lung Cancer H226 Cells The combination therapy of Cerium Oxide Nanoparticles with Radiation and chemotherapeutic agent Paclitaxel is assayed in a lung cancer cell line H226. Other cell lines PC14/PE6, A549, or H441 may also be used. These cell lines are human in origin and are used in cell based studies to determine the efficacy of cerium oxide nanoparticles with and without chemotherapy and radiation.
Experimental Design
Lung cancer H226 cells are plated in a 96 well plate for 24 hours. (density ~2000 cells/well). At time=0, culture media is changed and cells exposed to the following treatment conditions.
Control
5Gy Radiation
100 µg Paclitaxel
Varying concentrations of Cerium Oxide nanoparticles (0, 10 nM, 100 nM, 1 µM, and 100 µM) are assayed in combination with radiation and Gemcitabine
At 96 h after treatment, cell viability is measured using the Cell-Titer Glo Luminescent Cell Viability Assay and plates are read using an Optima microplate reader.
Orthotopic animal models such as athymic nude mice that tolerate the implantation or injection of the human cells are used to confirm cell culture results. Once the cell lines are injected into the organ in the mice, in which they originated from the human (i.e. breast mammary fat pad or lung tissue), the mice are then treated similarly. Tumor growth/tumor volume/tumor weight (to determine efficacy of the agents on the growth of the tumor), body weight (to determine toxicity) and survival (to determine tolerability) are measured. Histology and pathology examination is performed on the orthotopic cancer tissue and surrounding normal tissue to determine changes in cell death, cell proliferation, protection by way of skin burns for external tissue, fibrosis for lung tissue, changes in proteins and changes in cell death or survival pathways using established methods.

Example 10

Effect of Cerium Oxide Nanoparticles in Combination with Radiation+Gemcitabine on Colon Cancer Colo 320 Cells The combination therapy of Cerium Oxide Nanoparticles with Radiation and chemotherapeutic agent Paclitaxel is assayed in a colon cancer cell line COLO 320. Other cell lines such as Caco-2, DLD-1, HCT-15, HCT-116, HT-29, SW620, WiDr, and LS174T and TC71 may also be used. These cell lines are human in origin and are used in cell based studies to determine the efficacy of cerium oxide nanoparticles with and without chemotherapy and radiation.

Experimental Design

Colon cancer COLO 320 cells are plated in a 96 well plate for 24 hours. (density ~2000 cells/well). At time=0, culture media is changed and cells exposed to the following treatment conditions.

Control
5Gy Radiation
100 μM Irinotecan
Varying concentrations of Cerium Oxide nanoparticles (0, 10 nM, 100 nM, 1 μM, and 100 μM) are assayed in combination with radiation and Gemcitabine At 96 h after treatment, cell viability is measured using the Cell-Titer Glo Luminescent Cell Viability Assay and plates are read using an Optima microplate reader.

Orthotopic animal models such as athymic nude mice that tolerate the implantation or injection of the human cells are used to confirm cell culture results. Once the cell lines are injected into the organ in the mice, in which they originated from the human (i.e. breast mammary fat pad or lung tissue), the mice are then treated similarly. Tumor growth/tumor volume/tumor weight (to determine efficacy of the agents on the growth of the tumor), body weight (to determine toxicity) and survival (to determine tolerability) are measured. Histology and pathology examination is performed on the orthotopic cancer tissue and surrounding normal tissue to determine changes in cell death, cell proliferation, protection by way of skin burns for external tissue, fibrosis for lung tissue, changes in proteins and changes in cell death or survival pathways using established methods.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods, constructs and materials are now described. All publications mentioned herein are incorporated herein by reference in their entirety. Where there are discrepancies in terms and definitions used in references that are incorporated by reference, the terms used in this application shall have the definitions given herein.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A method of treating treating pancreatic cancer or lung cancer in a patient in need thereof, comprising:
    administering an effective dose of cerium oxide nanoparticles (CONP) to the patient;
    administering a therapeutically effective dose of ionizing radiation to the patient; and
    administering a therapeutically effective dose of a chemotherapeutic agent to the patient,
wherein the chemotherapeutic agent is not linked to the CONP and wherein the chemotherapeutic agent is paclitaxel or gemcitabine; thereby treating the cancer.

2. The method of claim 1, wherein the effective dose of cerium oxide nanoparticles is a dose that lowers the therapeutically effective dose of ionizing radiation and/or the chemotherapeutic agent compared to the therapeutically effective dose of ionizing radiation and/or the chemotherapeutic agent in the absence of the nanoparticles.

3. The method of claim 1, wherein the dose of ionizing radiation and/or the chemotherapeutic agent is between about 1% and 90%, or between about 1% and 80%, or between about or 1% and 70%, or between about 1% and 60%, or between about 1% and 50%, or between about 1% and 40%, or between about 1% and 30%, or between about 1% and 20%, or between about 1% and 10% of either (i) the dose used in the current treatment standard in the absence of CONPs or (ii) the effective amount to treat the tumor in the absence of CONPs.

4. The method of claim 1, wherein the ionizing radiation is administered after at least one of the cerium oxide nanoparticles and chemotherapeutic agent are administered.

5. The method of claim 1, wherein the ionizing radiation is administered before at least one of the cerium oxide nanoparticles and chemotherapeutic agent are administered.

6. The method of claim 1, wherein the chemotherapeutic agent is administered before at least one of the cerium oxide nanoparticles and ionizing radiation.

7. The method of claim 1, wherein the chemotherapeutic agent is administered at the same time as at least one of the cerium oxide nanoparticles and ionizing radiation.

8. The method of claim 1, wherein the chemotherapeutic agent is administered after at least one of the cerium oxide nanoparticles and ionizing radiation.

9. The method of claim 1, wherein the cerium oxide nanoparticles have a particle size between about 1 nanometer to about 20 nanometers; or between about 3 nanometers to about 15 nanometers; or between about 3 nanometers to about 10 nanometers; or between about 3 nanometers to about 5 nanometers.

10. The method of claim 1, wherein the effective dose of the cerium oxide nanoparticles is between about 1 nanogram per kilogram patient body weight to about 50 milligrams per kilogram patient body weight; or between about 1 nanogram per kilogram patient body weight to about 5 milligrams per kilogram patient body weight; or between about 1 nanogram per kilogram patient body weight to about 0.5 milligrams per kilogram patient body weight; or between about 10 nanogram per kilogram patient body weight to about 0.5 milligrams per kilogram patient body weight; or between about 20 nanogram per kilogram patient body weight to about 100 micrograms per kilogram patient body weight; or between about 10 nanogram per kilogram patient body weight to about 10 micrograms per kilogram patient body weight.

11. The method of claim 1, wherein the cerium oxide nanoparticles are provided in the form of a composition comprising cerium oxide nanoparticles and a pharmaceutically acceptable carrier; wherein the cerium oxide nanoparticle composition may be administered by topical, oral, parenteral, buccal, sublingual, nasal, rectal, patch, pump or transdermal administration.

12. The method of claim 1, wherein the cerium oxide nanoparticle composition is a topical composition.

13. The method of claim 12, wherein the topical composition comprises CONPs, a surfactant, an oil and water.

14. The method of claim 1, wherein the cerium oxide nanoparticle composition is a micro-emulsion.

15. The method of claim 1, wherein the total concentration of cerium oxide nanoparticles in the blood plasma of the patient following administration is between about 5 nanomolar to about 200 micromolar; or between about 10 nanomolar to about 100 micromolar; or between about 20 nanomolar to about 10 micromolar.

16. The method of claim 1, wherein the chemotherapeutic agent is a prodrug.

17. A method for reducing toxicity of at least one of ionizing radiation and at least one chemotherapeutic agent administered to a patient undergoing pancreatic cancer or lung cancer treatment, comprising
    (i) administering an effective dose of CONPs to the patient,
    (ii) administering a dose of at least one of ionizing radiation and at least one chemotherapeutic agent, wherein the chemotherapeutic agent is not linked to the CONP and administering an effective dose of CONPs reduces the toxicity of at least one of ionizing radiation and at least one chemotherapeutic agent administered to the patient, and wherein the chemotherapeutic agent is paclitaxel or gemcitabine.

18. A method for decreasing a dose of at least one of ionizing radiation and at least one chemotherapeutic agent administered to a patient required to effectively treat pancreatic cancer or lung cancer, comprising
    (i) administering an effective amount of CONPs to the patient,
    (ii) administering a dose of at least one of ionizing radiation and at least one chemotherapeutic agent, wherein the chemotherapeutic agent is not linked to the CONP and administering an effective dose of CONPs reduces the dose of ionizing radiation and/or at least one chemotherapeutic agent required to effectively treat pancreatic cancer or lung cancer, and wherein the chemotherapeutic agent is paclitaxel or gemcitabine.

19. A method for increasing the effectiveness of a dose of at least one of ionizing radiation and the last one chemotherapeutic agent administered to a patient required to effectively treat pancreatic cancer or lung cancer, comprising
    (i) administering an effective amount of CONPs to the patient,
    (ii) administering a dose of at least one of ionizing radiation and at least one chemotherapeutic agent, wherein the chemotherapeutic agent is not linked to the CONP, and wherein the chemotherapeutic agent is paclitaxel or gemcitabine.

20. A composition comprising an effective dose of cerium oxide nanoparticles for the treatment of pancreatic cancer or lung cancer in a patient, wherein the patient is receiving a therapeutically effective dose of ionizing radiation and a therapeutically effective dose of a chemotherapeutic agent for the treatment of the cancer, wherein the chemotherapeutic agent is not linked to the CONP, and wherein the chemotherapeutic agent is paclitaxel or gemcitabine.

* * * * *